(12) United States Patent
Broyles

(10) Patent No.: US 9,089,521 B2
(45) Date of Patent: Jul. 28, 2015

(54) METHOD FOR REGULATING PRODUCTION OF HEMOGLOBIN BETA CHAINS

(76) Inventor: Robert H. Broyles, Oklahoma City, OK (US)

(*) Notice: Subject to any disclaimer, the term of this patent is extended or adjusted under 35 U.S.C. 154(b) by 940 days.

(21) Appl. No.: 12/388,440

(22) Filed: Feb. 18, 2009

(65) Prior Publication Data

US 2011/0171179 A9    Jul. 14, 2011

Related U.S. Application Data

(63) Continuation-in-part of application No. 10/003,669, filed on Nov. 1, 2001, now Pat. No. 7,517,669, and a continuation-in-part of application No. 11/369,179, filed on Mar. 6, 2006, now Pat. No. 7,718,699.

(60) Provisional application No. 60/658,803, filed on Mar. 4, 2005.

(51) Int. Cl.

| | |
|---|---|
| *A61K 38/00* | (2006.01) |
| *A61K 38/17* | (2006.01) |
| *C07K 14/47* | (2006.01) |
| *C12N 5/09* | (2010.01) |
| *A61K 48/00* | (2006.01) |
| *A61K 35/12* | (2015.01) |

(52) U.S. Cl.
CPC ............ *A61K 38/1709* (2013.01); *C07K 14/47* (2013.01); *C12N 5/0694* (2013.01); *A61K 48/00* (2013.01); *A61K 2035/124* (2013.01); *C12N 2501/385* (2013.01)

(58) Field of Classification Search
CPC . A61K 35/15; A61K 38/1709; C12N 5/0641; C12N 2502/1128; C07K 14/47; C07K 14/4702
USPC .................... 514/5.4, 21.2; 530/350
See application file for complete search history.

(56) References Cited

U.S. PATENT DOCUMENTS

| | | | |
|---|---|---|---|
| 4,582,820 | A | 4/1986 | Teng |
| 5,283,323 | A | 2/1994 | Berzofsky et al. |
| 7,097,841 | B2 | 8/2006 | Carter et al. |
| 2002/0128183 | A1 | 9/2002 | Broyles et al. |

OTHER PUBLICATIONS

Broyles et al. Free Radical Biol Med 2007;43:Suppl1,S67.*
Okada et al. Brit J Cancer 2001;84:1564-70.*
Fargion et al. Blood 1988;71:753-7.*
Broxmeyer et al. Blood 1986;68:1257-63.*
Abruzzese et al., Molecular Therapy, 2(3):276-287, 2000.
Adams et al., New Eng J Med, 339:5-11, 1998.
Ammendola et al., J Biol Chem, 267(25): 17944-17948, 1992.
Andrews et al., Nature, 362:722-8, 1993.
Applegate et al., J Invest Dermatol, 111(1): 159-163, 1998.
Armstrong et al., Cell, 95:93-104, 1998.
Arosio et al., Cancer Res, 36: 1735-1739, 1976.
Atkinson et al., Biochem Cell Biol, 67:52-7, 1989.
Aziz et al., Proc Natl Acad Sci USA, 84:8478-82, 1987.
Barker-Harrel et al., Exp Cell Res, 178:435-448, 1988.
Bartzokis et al., Arch Neurol, 56:569-574, 1999.
Berg et al., Nucleic Acids Res, 17:8833-52, 1989.
Bettan et al., Molecular Therapy, 2 (3):204-210, 2000.
Bhanu et al., Blood, 105(1):387-393, 2005.
Bieker, Curr Opin Hematol, 5(2):145-50, 1998, Abstract.
Bieker et al., Ann NY Acad Sci, 850:64-69, 1998.
Blau et al., Curr Opin Hematol, 1(2):136-42, 1994.
Bodine, Molecular Therapy, 2 (2): 101-102, 2000.
Bowie et al., Science, 247:1306-10, 1990.
Bristol et al., Molecular Therapy, 2 (3): 223-232, 2000.
Brown et al., J Biol Chem, 253(8):2673-8, 1978.
Broxmeyer et al., PNAS, 88:770-4, 1991.
Broyles et al., Developmental Genetics, 15:347-355, 1994.
Broyles et al., FASEB J, 9(6):A1328, 1995, Abstract.
Broyles et al., Colloque INSERM, 234:43-51, 1995.
Broyles, Sem Cell Develo Biol, 10:259-265. 1999.
Broyles et al., PNAS, 98(16):9145-9150, 2001.
Broyles et al., IBIS 2005 Meeting, 2005, Abstract.
Broyles et al., 48th ASH Annual Meeting, 2006, Abstract.
Broyles et al., 29th Annual Meeting of the National Sickle Cell Disease Program, 2006, Abstract.
Broyles et al., Society for Free Radical Biology & Medicine Annual Meeting, 2007, Abstract and Oral Presentation.
Broyles et al., IBIS 2007 Meeting, 2007, Abstract.
Buckel, Trends Pharmacol Sci, 17:450-6, 1996.
Cai et al., J Biol Chem, 272(19): 12831-12839, 1997.
Cai et al., Mol Biol Cell, 9: 1037-51, 1998.
Casey et al., Science, 240:924-928, 1988.
Chang et al., DNA Cell Biol, 9(3):205-212, 1990.
Chase, "Binding of HMG-I(Y) elicits structural changes in a silencer of the human b-globin gene", 1999, XP008009648.
Cheepsunthorn et al., J Comb Neurol, 400:73-86, 1998.
Chen et al., Molecular Therapv, 2 (3):256-261, 2000.
Dean et al., Prog Clin Biol Res, 134:323-34, 1983.
Dean et al., PNAS USA, 80:5515-9, 1983.
Deboer et al. Embo J, 7(13):4203-4212, 1988.
Dickey et al., J Biol Chem, 262(16):7901-7907, 1987.
Dignam et al., Nucleic Acids Res, 11(5):1475-89, 1983.
Donze et al., J Biol Chem, 270(4): 1955-59, 1995.
Dover et al., Blood, 69(4): 1109-13, 1987.
Epner et al., Mol Cell, 2:447-55, 1998.
Ferreira et al., J Biol Chem, 275(5):3021-3024, 2000.
Files et al., J Pediatr Hematol/Oncol, 24:284-290, 2002.

(Continued)

*Primary Examiner* — Janice Li
(74) *Attorney, Agent, or Firm* — Denton Intellectual Property Law Firm, LLC; F. Russell Denton

(57) ABSTRACT

A method is described for repressing production of β-globin protein and increasing production of γ-globin protein in a human cell utilizing a ferritin-H protein, a vector encoding ferritin-H, or an exogenous ferritin-H inducer.

9 Claims, 28 Drawing Sheets
(5 of 28 Drawing Sheet(s) Filed in Color)

(56) References Cited

OTHER PUBLICATIONS

Fordis et al., Prog Clin Biol Res, 191:281-92, 1985.
Fordis et al., Biochem Biophys Res Commun, 134(1):128-33, 1986.
Fried et al., Nucleic Acids Res, 9(23):6505-25, 1981.
Gao et al., Molecular Therapy, 2(2):233-244, 2000.
Gribnau et al., Mol Cell, 5:377-86, 2000.
Griffiths et al., Brain, 122:667-673, 1999.
Gumucio et al., Proc Natl Acad Sci USA, 90:6018-22, 1993.
Haile et al., Proc Natl Acad Sci USA, 89: 11735-39, 1992.
Harrison et al., Biochim Biophys Acta, 1275: 161-203,1996.
Hengge et al., Molecular Therapy, 2 (3): 188-194, 2000.
Hentze et al., Proc Natl Acad Sci USA, 83:7226-30, 1986.
Hentze et al., Science, 238: 1570-3, 1987.
Herzog et al., Expert Rev Cardiovascular Ther, 1:215-32, 2003.
Higgs, Cell, 95: 299-302, 1998.
Jane et al., Mol Cell Biol, 13(6): 3272-81, 1993.
Kennedy et al., Proc Natl Acad Sci USA, 89:11730-34, 1992.
Kirkali et al., Urol Int, 62:21-25, 1999.
Kreisberg et al., Infect Immun, 62(7):2991-94, 1994.
Kurien et al., Anal Biochem, 245:123-126, 1997.
Leimberg et al., Am J Hematol, 73:211-12, 2003.
Li et al., Proc Natl Acad Sci USA, 94: 2444-48, 1997.
Lin et al., Arch Biochem Biophys, 352(1):51-58, 1998.
Lohr et al., Molecular Therapy, 2(3):195-203, 2000.
Macleod et al., Mol Cell Biol, 11(9):4324-32, 1991.
Mandishona et al., Hepatology, 27(6): 1563-1566, 1998.
Maniatis et al., Molecular Cloning: A Laboratory Manual, Cold Spring Harbor Laboratory, Cold Spring Harbor, New York, 1982.
Mankad, Pediatric Pathlol Mol Med, 20:1-13, 2001.
Matsumoto et al., Methods in Enzv, Academic Press, New York, 316(330):492-511, 2000.
McCune et al., PNAS USA, 91:9852-56, 1994.
Meyron-Holtz et al., Blood, 94:3205-11, 1999.
Miller et al., Mol Cell Biol, 13(5); 2776-86, 1993.
Orkin, Eur J Biochem, 231: 271-81, 1995.
Papyannopoulou et al., Cell, 46: 469-76, 1986.
Picard et al., Blood, 87(5):2057-64, 1996.
Picard et al., J Biol Chem, 273(25):15382-86, 1998.
Pountney et al., J Cell Sci, 112:825-31, 1999.
Puthenveetil et al., Curr Hematology Reports, 3:298-305, 2004.
Reik et al., Mol Cell Biol, 18(10): 5992-6000, 1998.
Rodgers et al., Prog Clin Biol Res, 316B:281-93, 1989.
Rodgers et al., New Eng J Med, 322(15):1037-1045, 1990, Abstract.
Rudinger, J. "Characteristics of the amino acids as components of a peptide hormone sequence" in "Peptide Hormones" Parsons, J.A., Ed., University Park Press, Jun. 1976.
Schwarze et al., Trends Cell Biol, 10:290-95, 2000.
Sheridan et al., Molecular Therapy, 2(3):262-275, 2000.
Shterman et al., Cancer Res, 49: 5033-36, 1989.
Somiari et al., Molecular Therapy, 2 (3): 178-187, 2000.
Sowemimo-Coker, Transfus Med Rev, 16:46-60, 2002.
Theil, Ann Rev Biochem, 56:289-315, 1987.
Thompson et al., J Cell Sci, 115:2165-77, 2002.
Thomson, FEBS Lett, 285(2), 1991.
Tsai et al., Nature, 339:446-51, 1989.
Welch et al., Free Radic Biol Med, 33:399-408, 2002.
Wu et al., J Biol Chem, 266(26): 17566-72, 1991.
Wu et al, Molecular Therapy, 2 (3):288-297, 2000.
Conclusions from the NIH consensus statement "newborn screening for Sickle cell disease and other hemoglobinopathies", NIH Consensus Statement Online, 1987.
Insulin and Diabetes, Pubmed 2005.
"Turning off the sickle cell gene", OU Health Sciences Magazine, 1982.
Lin, H.J., et al., "Activation of the human β-globin promoter in K562 cells by DNA sequences 5' to the fetal γ- or embryonic ζ-globin genes," *J. Clin. Invest.* 80:374-380 (1987).
Young, K., et al., "*Trans* acting regulation of β globin gene expression in erythroleukemia (K562) cells," *Nucl. Ac. Res.*, 13(14):5203-5213 (1985).
Anonymous, Entry at "Produce," *American Heritage Dictionary of the English Language*, 5$^{th}$ Edition (2012), Houghton-Mifflin, Boston, MA, U.S., posted as of Oct. 18, 2012 at http://ahdictionary.com/word/search.html?q=produce.
Anonymous, "Legislative Initiatives," posted as of Oct. 18, 2012 by the Sickle Cell Disease Association of America at www.sicklecelldisease.org/index.cfm?page=legislative-initiatives.
Anonymous, "Sickle Cell Research for Treatment and Cure," posted as of Oct. 18, 2012 by the National Heart, Lung and Blood Institute (U.S. National Institutes of Health), at www.nhlbi.nih.gov/resources/docs/scd30/index.htm.
Anonymous, "Diseases and Conditons: Sickle Cell Disease," posted as of Oct. 18, 2012 by the Cleveland Clinic (U.S.) at /my.clevelandclinic.org/disorders/Sickle_Cell_Anernia/hic_Sickle_Cell_Disease.aspx.
Anonymous, "Genes and Human Disease," posted as of Oct. 18, 2012 by the World Health Organization, at www.who.int/genomics/public/geneticdiseases/en/index2.html.
Kauf, T.L. et al., "The cost of health care for children and adults with sickle cell disease," *Am. J. Hematol.*, 2009: 84:323-327.
Kutlar, A., et al., "A phase 1/2 trial of HQK-1001, an oral fetal globin inducer, in sickle cell disease," *Am J Hematol*, Jul. 9, 2012, 00-000 (p. 1-5) doi: 10.1002/ajh.23306. [Epub ahead of print].
Schultz, R.D., et al., "Occurence of blood cells and serum proteins in bovine fetuses and calves," *Can. J. Comp. Med.*, Apr. 1971; 35(2):93-96.
Winter, W.P., "A Brief History of Sickle Cell Disease," (Howard University, U.S.) posted at www.sicklecell.howard.edu/ABriefHistoryofSickleCellDisease.htm.

* cited by examiner

WT and Mutant Oligonucleotides of -164/-128, 5' β-Globin

WT sequence:           5' AACTCCTAAGCCAGTGCCAGAAGAGCCAAGGACAGGT 3'

Mutant #1 (-162/-157): 5' AAGGGGGGAGCCAGTGCCAGAAGAGCCAAGGACAGGT 3'

Mutant #2 (-144/-139): 5' AACTCCTAAGCCAGTGCCAGAAAAAAACAAGGACAGGT 3'

Mutant #3 (-135/-130): 5' AACTCCTAAGCCAGTGCCAGAAGAGCCAACCCCCCGT 3'

Mutant #4 (-153/-148): 5' AACTCCTAAGCAAAAAACAGAAGAGCCAAGGACAGGT 3'

| Competitor Oligonucleotide | Molar Excess producing 50 % Inhibition |
|---|---|
| Wild type (WT) | 42x |
| Mutant #1 | 30x |
| Mutant #2 | 38x |
| Mutant #3 | 35x |
| Mutant #4 | 850x |

FIG. 5

|  | | -162 | -153 -148 | -142 |
|---|---|---|---|---|
| Human | | TCCTAAGC | CAGTGC | CAGAAG |
| Gorilla | | TCCTAAGC | CAGTGC | CAGGAG |
| Macaca | | TCCTAAGC | CAGTGC | CAGAAG |
| Bovine | | TCTAAAGT | CAGTGC | CAGGAA |
| Goat | | TCTAAAGT | CAGTGC | CAGGAA |
| Sheep | | TCTAAAGT | CAGTGC | CAGGAA |
| Galago | | TCCTAAGT | GAGTGC | CAGAAC |
| Tarsius | | CTCTAAGC | CAGTAC | CAGAAC |
| Lepus | | TCCTAAGC | CATTGC | CAGAAC |
| Rabbit | | TCCTAAGC | CATTGC | CATAAC |
| Rat | | CCTGAGGC | CAGTGG | CCCAGC |
| Mouse | | TCTTAAGC | CTGTGC | CATAGC |

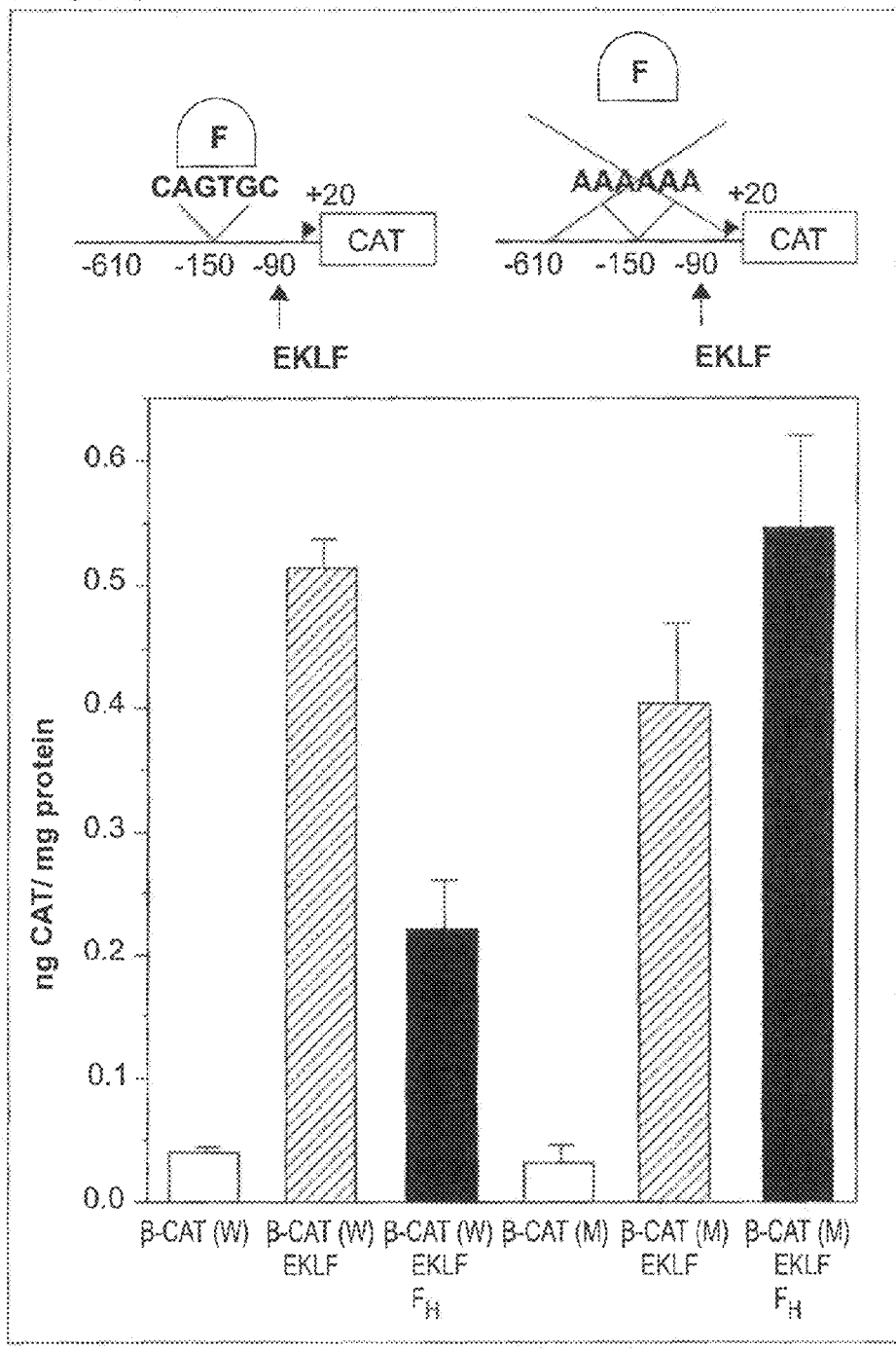

Excitation Maxima 488nm   Excitation Wavelength 485nm
Emission Maxima 507 nm    Emission Wavelength 538 nm Transfection of K562 cells with Antisense-hFtH-Alexa488

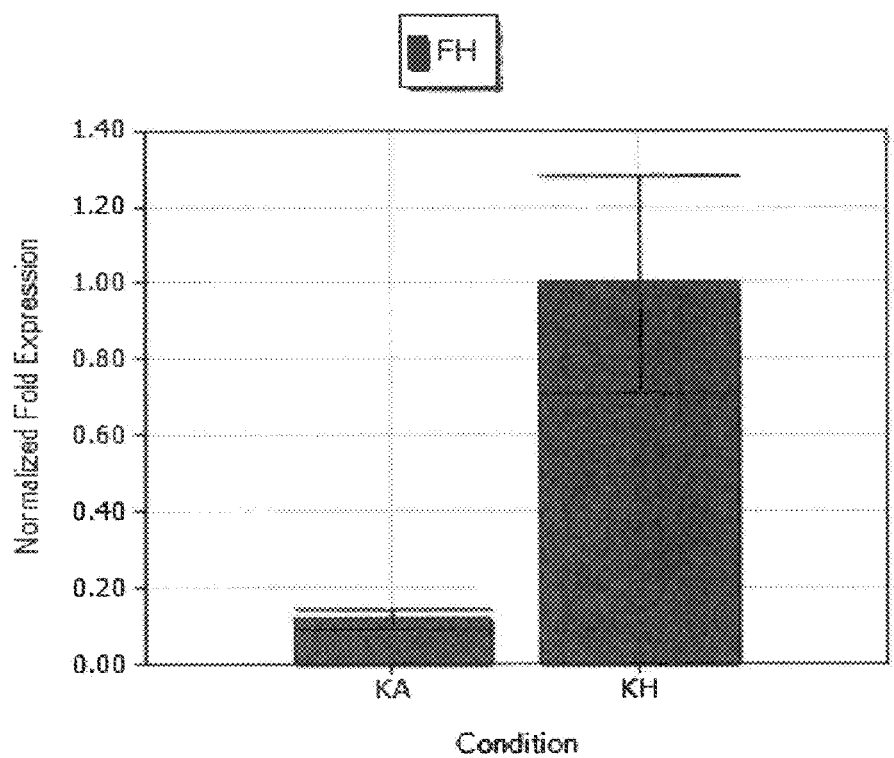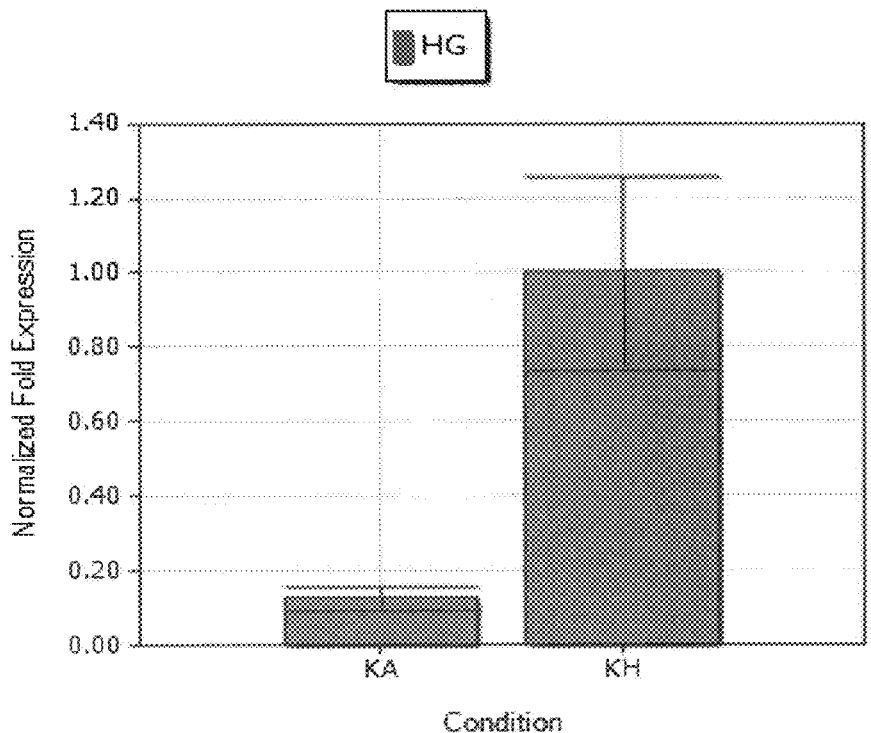
Figure 16 (B)

(a)
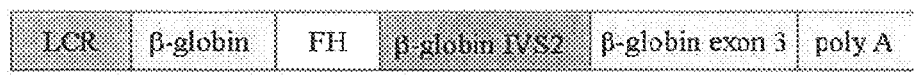
(b) $\beta^{Maj}/\beta^{Min}$: 1.37  1.56
  1    2    3
α4 globin
$\beta^{maj}$ globin
$\beta^{min}$ globin
α1 globin
(c)
wt
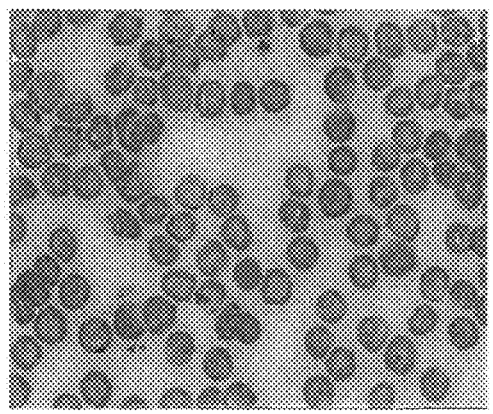
FH transgenic
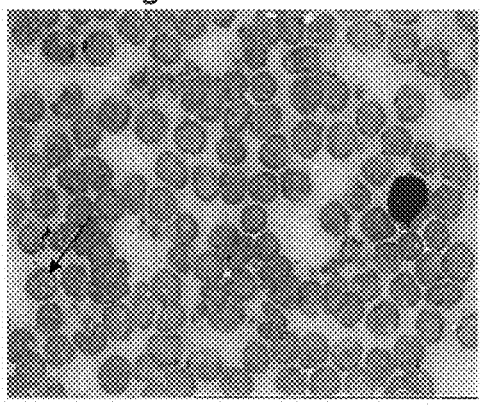
% Target Cells:   6.5%                    22.6%
Figure 18

Fluorescence microscopy of human erythroid cells taking up FtH-FITC protein from the medium in 1 hour @ 37° C, with the aid of SAINT MIX transfection reagent

SEQUENCE LISTING

<160> NUMBER OF SEQ ID NOS: 27

<210> SEQ ID NO 1
<211> LENGTH: 37
<212> TYPE: DNA
<213> ORGANISM: Homo sapiens

<400> SEQUENCE: 1
aactcctaag ccagtgccag aagagccaag gacaggt                37

<210> SEQ ID NO 2
<211> LENGTH: 37
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(37)
<223> OTHER INFORMATION: Synthetic primer

<400> SEQUENCE: 2
aaggggggag ccagtgccag aagagccaag gacaggt                37

<210> SEQ ID NO 3
<211> LENGTH: 37
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(37)
<223> OTHER INFORMATION: Synthetic primer

<400> SEQUENCE: 3
aactcctaag ccagtgccag aaaaaacaag gacaggt                37

<210> SEQ ID NO 4
<211> LENGTH: 37
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(37)
<223> OTHER INFORMATION: Synthetic primer

<400> SEQUENCE: 4
aactcctaag ccagtgccag aacagccaac cccccgt                37

<210> SEQ ID NO 5
<211> LENGTH: 37
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(37)
<223> OTHER INFORMATION: Synthetic primer

<400> SEQUENCE: 5
aactcctaag caaaaaacag aagagccaag gacaggt                37

<210> SEQ ID NO 6
<211> LENGTH: 6

```
<212> TYPE: DNA
<213> ORGANISM: Homo sapiens

<400> SEQUENCE: 6 cagtgc                                                                  6

<210> SEQ ID NO 7
<211> LENGTH: 20
<212> TYPE: DNA
<213> ORGANISM: Homo sapiens

<400> SEQUENCE: 7
tcctaagcca gtgccagaag                                                  20

<210> SEQ ID NO 8
<211> LENGTH: 20
<212> TYPE: DNA
<213> ORGANISM: Gorilla gorilla

<400> SEQUENCE: 8
tcctaagcca gtgccaggag                                                  20

<210> SEQ ID NO 9
<211> LENGTH: 20
<212> TYPE: DNA
<213> ORGANISM: Macaca

<400> SEQUENCE: 9
tcctaagcca gtgccagaag                                                  20

<210> SEQ ID NO 10
<211> LENGTH: 20
<212> TYPE: DNA
<213> ORGANISM: Bos taurus

<400> SEQUENCE: 10
tctaaagtca gtgccaggaa                                                  20

<210> SEQ ID NO 11
<211> LENGTH: 20
<212> TYPE: DNA
<213> ORGANISM: Capra hircus

<400> SEQUENCE: 11
tctaaagtca gtgccaggaa                                                  20

<210> SEQ ID NO 12
<211> LENGTH: 20
<212> TYPE: DNA
<213> ORGANISM: Ovis sp.

<400> SEQUENCE: 12
tctaaagtca gtgccaggaa                                                  20

<210> SEQ ID NO 13
<211> LENGTH: 20
<212> TYPE: DNA
<213> ORGANISM: Galago sp.

<400> SEQUENCE: 13
tcctaagtga gtgccagaac                                                  20

<210> SEQ ID NO 14
```

```
<211> LENGTH: 20
<212> TYPE: DNA
<213> ORGANISM: Tarsus

<400> SEQUENCE: 14
ctctaagcca gtaccagaac                                                      20

<210> SEQ ID NO 15
<211> LENGTH: 20
<212> TYPE: DNA
<213> ORGANISM: Lepus

<400> SEQUENCE: 15
tcctaagcca ttgccagaac                                                      20

<210> SEQ ID NO 16
<211> LENGTH: 20
<212> TYPE: DNA
<213> ORGANISM: Cuniculus

<400> SEQUENCE: 16
tcctaagcca ttgccataac                                                      20

<210> SEQ ID NO 17
<211> LENGTH: 20
<212> TYPE: DNA
<213> ORGANISM: Rattus Norvegicus

<400> SEQUENCE: 17
cctgaggcca gtggcccagc                                                      20

<210> SEQ ID NO 18
<211> LENGTH: 20
<212> TYPE: DNA
<213> ORGANISM: Mus musculus

<400> SEQUENCE: 18
tcttaagcct gtgccatagc                                                      20

<210> SEQ ID NO 19
<211> LENGTH: 7398
<212> TYPE: DNA
<213> ORGANISM: Homo sapiens

<400> SEQUENCE: 19
gctaatgagg tgtctctatg ctgtctctag gatcaagttt aacctctttt tatggaacac          60
aaccctgccc gatcttgccc ctattctcca ccctaaccag catcccccaa cataaactgt         120
actttccagg ccaacattct ttcttttcttt cttttttttt ttttttttg agacggagtt         180
ttgttttgtc ttccaggctg gagtgcaaag gcgcgatctc ggctcactgc aacctccgcc         240
tcccaggttc aagcgattct cctgcctcag cctccagaat agctaggatt acaggcgcat         300
gccaccacgc ccggctaatt tttgtatttt cagtagagaa gggtttagcc atgttagtta         360
gccaggctga tctccaactc cgacctcaag tgatccgccc gcctcggcct cccaaaatgc         420
tgggattaca ggcatgagcc accgcgccca gccccaggca acatattttc ttaaggagct         480
ttaacaggcc atgcatttcc acatttccac acctttgcat atgctgttca ctctgctcca         540
aattcccttc cctgtttctc tcccgcactt caccttcctt ttaactttttt cttcaaactc       600
agctcacgtg tcttgcttag ggagggcttc cccgacctcc tcctatccca gactgggtaa         660
ggtactcctg gtctagcagc atccttctgt ttaccttatt cttgtagctc tagcaccact         720
```

-continued

```
aaaacgtttt tcctgtaaat aacataggtg catttttaaa tgaaaccgtg aacaagaaat      780
caccctaatt ccgtcggcaa tttattttag tatttcagta gagttgcttt tttaaactaa      840
ggtttggaag tctagcttcc agctgcaggt ttgtgagcat cctgaaattc agttcttcca      900
ccgatgcgtc aaaagacgcg acagaacagt ggacctcgaa gccaggacct aggtaagggc      960
agggcctagc tctagctctg ccacccataa attcacatcc accctgtgcc tgggactcag     1020
cttagccaca cacaccggcc ccaccctcc ggggtctctt tcacctgtca cccgccatta     1080
accccgtcag cttctctcca atgacacccc agggttgtcc tacagggcca ccgaagcctg     1140
aagctcctgt gagtggggcc gataagaggc cattttgaaa agtcctcagc atgggcttcg     1200
cctttagatc cacgtcgttt ctcctttcta acccgagatg tgtcccttgg gtgcgaagcg     1260
acaccagcga ttctctcgga ggccccggtg gctcacccccc acgactcccc ggggaggcgg     1320
tccccatccc tagggaaacc cggcccgccc agcctttgtt gcagaaaccg cacacggagc     1380
catatttgct ttcagccaaa ggcagacgtg gtcggaggag tcggaagggc aggggcggac     1440
ccgaaacccg ccgtgcgccc acttctcca tcgcgctcct tcctggactc tgaggaagag     1500
aaaatgcgct cgaccaccta aggaccgcgt ctccaccttc caccttccca atcatctgca     1560
gcttcccaat ctgcagcttc ccaatctgca gcaaggtgtc acaagggctt ctccgcagct     1620
atgatttcta acaccatgcc ccgggccagg agcctcaggg tgcccgttcg ggaaaatggg     1680
agccgaatca ggatcacccc atgcgccccc gcacccttcc ccgccggtt ccaacgcccg     1740 ggcgccccta accgggggg ggggttctga ggtggacttc ctgcgcctcc tcgcagcttc     1800
cctccaactc cactaaacgg gcacagagac gccaccgctg tcccagaggc agtcggctac     1860
cggtccccgc tcccgagctc cgccagagcg cgcgagggcc tccagcggcc gcccctcccc     1920
cacagcaggg gcgggtccc gcgcccaccg gaaggagcgg gctcggggcg ggcggcgctg     1980
attggccggg gcgggcctga cgccgacgcg gctataagag accacaagcg acccgcaggg     2040
ccagacgttc ttcgccgaga gtcgtcgggg tttcctgctt caacagtgct tggacggaac     2100
ccggcgctcg ttccccaccc cggccggccg cccatagcca gccctccgtc acctcttcac     2160
cgcaccctcg gactgcccca aggccccgc cgccgctcca gcgccgcgca gccaccgccg     2220
ccgccgccgc ctctccttag tcgccgccat gacgaccgcg tccacctcgc aggtgcgcca     2280
gaactaccac caggactcag aggccgccat caaccgccag atcaacctgg agctctacgc     2340
ctcctacgtt tacctgtcca tggtgagcgc gggcgggcct aagcggtggc ggggccggg     2400 cgcggttccc ggggcgcgcg ctgggcgggg ccggggggtgt ggccacccgc gggctctccc     2460
gcctccctgc gcccttctgg aaaatggagg ctgctcgagg tttccgagga cttctctggc     2520
gcagaaagtc ggggcagctg gttcttctcg gctgtaccct gagaatgctc cctcctaggc     2580
cagggccgcc tctgcacacc cttctttttt aaggagacct tggtgtcctg aaatcctggg     2640
gttgcaagac tgccagcctg tgtgatcaat cctgcggtta ggaaggtgga gttttgcttt     2700
cccatctttt cctctgcctc cggcatttgg ccctaaatgc cagcgttttt tgcttaggta     2760
tccagctccc gtccgcctgt gtgtggcgga gctgctgggt aacggtgtcg aatagcaaac     2820
cttgggggct ggcgggaggt ggcttatctt gtgggtagat ccctctcgag cagccgtatc     2880
cacctctcgg ctctgcttat ctctaagtcc cacttgcttt gaagcatatc tctaggaatc     2940
gccccttctg cagtcaccga agtgtcacct gaccttgcgc ctaggggacc taatttatct     3000
tttatgtatc ttactgtaag aggtgtggag tttggcctac taattgaacc cccagttctt     3060
```

-continued

```
ggataaagtc caccgacagt tactgggcaa gaaattttc agtgatcagt ggaatcaatt        3120
ttcccaaatc ttggtcttag gcagtgtcgt gggagtcttc cttagaattg ccttgtgatt        3180
gtccaaacta tcccaagaat aaatgtgttc caaatggatt tgaaaacagg cctgtatttc        3240
tgtgactgtc actgcctttc acaaacactt gactacatca aatgtctaaa actgaaaatc        3300
aaatttttgt gatataacta ttataaaagt atgtttacat caacatactg tccacatttg        3360
ccaccttgca tgggggtttt taatttgtgt gtgtgtgtga gagagacaga gtcttcgctc        3420
tgtcgcccag gctggagtgc agtggcgcga tctcggctca ctgcagcctc cgcctcctgg        3480
gttcaagtga ttctcttacc tcaggctcct gagtagctgg aattacaggc gcacgccacc        3540
acgcccagct attttttttt attttagta gagacggggt ttcaccatgt tgaccaggat        3600
ggtctcgatc tgctgacctc gtgatccgcc tgcctcggcc tcccaaagtg ctgggattac        3660
aggctgagcc accgcaccca gcaggggttt ttaattttat aaataaatat gtggtacagc        3720
tggcagactc ctgagctcag ttttaaccat gctttaacat ggttaataca ggagcaggga        3780
ggagaaaagg actaagtgca gggtcagtac tccagcgccc tctcatcaga caatgaattc        3840
tgacactggc tgtaagtttt ctgtgcagta atacagatcc ttaagacatt gccccaggca        3900
atgcccataa tatcctaaag gttccttgaa gttaagtttc aaggatcaag tttcagtttt        3960
ctattttaga atagaaacat tactcttggg ttcaatccag tagctcatct gcccccagt        4020 ctccttaggc actgattcct tcatgctgtg ctttgagaaa ggaagcctag gctgacgaga        4080
ccatcttgcc tccctgtaga tcgtcacagc tacctgtctc tggggatccc tagtataaca        4140
cattcagtgt tcccctttca gtcttactac tttgaccgcg atgatgtggc tttgaagaac        4200
tttgccaaat actttcttca ccaatctcat gaggagaggg aacatgctga gaaactgatg        4260
aagctgcaga accaacgagg tggccgaatc ttccttcagg atatcaaggt gaacaaaga        4320 tcctagggt gtcatacgtc atacttcatc atctggcagt gttcgggtat cagaaatcac         4380
ttaaactagc aattgccctt ataaagtgat gatacactgg gcttttgcct tttgtgcttt        4440
tttaggctta ccatctaaac taaattaggc aaatagtaat gtccctttg ccaaaacgtg         4500 gtggttagag atgatgggct tgctgacttc taggttagtt ggtagagatg cattaaccta        4560
ttctcattca gaaaccagac tgtgatgact gggagagcgg gctgaatgca atggagtgtg        4620
cattacattt ggaaaaaaat gtgaatcagt cactactgga actgcacaaa ctggccactg        4680
acaaaaatga ccccatgtg agtattggaa ccccaggaaa taaatggagg aaatcatttg         4740
ccttagggat tgggaaagct gcccactaac tgtcttcccc attgttttgc agttgtgtga        4800
cttcattgag acacattacc tgaatgagca ggtgaaagcc atcaaagaat tgggtgacca        4860
cgtgaccaac ttgcgcaaga tgggagcgcc cgaatctggc ttgcggaat atctctttga        4920 caagcacacc ctgggagaca gtgataatga aagctaagcc tcgggctaat ttccccatag        4980
ccgtggggtg acttccctgg tcaccaaggc agtgcatgca tgttggggtt tcctttacct        5040
tttctataag ttgtaccaaa acatccactt aagttctttg atttgtacca ttccttcaaa        5100
taaagaaatt tggtacccag gtgttgtctt tgaggtcttg ggatgaatca gaaatctatc       5160
caggctatct tccagattcc ttaagtgccg ttgttcagtt ctaatcacac taatcaaaaa        5220
gaaacgagta tttgtattta ttaaactcat tagtttgggc agtatactaa ggtgtggctg        5280
tcttggattc agatagaact aagggttccc gactctgaat ccagagtctg agttaaatgt        5340
ttccaatggt tcagtctagc tttcacagtt tttatgaata aaaggcatta aaggctgaag        5400
tagtctggga ttttttatcta ttaagctaac catttgattc aggctgttgt aggacatgtt        5460
```

```
cttcagtgtg dacagctgta tggctgtgac tggatcagtg tcctgctggt gtacacacag    5520 ggtgaggacct ggctggcgaa gcatccccat taggaagcag gttaggaatg tgcttcatcc   5580
ctagtgagaa tgaaagtatt aacagcataa gtatggaagg taccttcatt tcaaataccca   5640 aaatgttgca gtaggagggc aaaggttgag acgatccttt tttttttttt tttgagacag    5700
tctcactccg tcgcccaggc tggattgcag ttgctcaatc tcactgcaac caccacctcc    5760
tgggttcaag caattctccc ctcaacctcc tgcgttggga ctacaggcac caccgacgc     5820 ccagctgatt tttgtatttt ttttggtaga gatgggtttt catcatgttg gccaggttgg    5880
tctcaaactc ctgacctcct gtgatccact gcctccaca cccagcccaa gacaagattc     5940
ttaaatatta acatcctttg ctgaacaggc cacagatgtt tgccaagttc ctgtctagcc    6000
ctagaagcaa gactgaaatt gttgcccttt taagttttca atcataatag ctgcgtgttc    6060
tgaccgtgaa agtaactgct tgagaatcca gaaaagggaa gttacacttc ctcccacgtg    6120
attggggctg aagtggggtg tttataattg ggtgaaagtg tccaggaaat ctggaataaa    6180
gggaaatatc tgattttgtg acagctttgg gctgacccca aggaagcaag aagtattttg    6240
gtgaggttcc caggcagtga gaaaatgacc taagggcgct ggacaccctc aacctcacca    6300
tctaccagtt cctaggagtg aggcagttcc tgccacccctt tcctgtagtg cttgggtact   6360
accctaaata gttatggggg aagtgttcat ctgtcatcca gctgactgcc acctcatggt    6420
tttgggtcag ccacccttgc tcaaagtaag ttggggccag tgataacatc tgctcagcta    6480
agcctggcct gtcagccctg gggcagttct ccagcagcat tctggtcagc acaacctcat    6540
cttccttcac ctggtcccaa gaagtcttcc gggtgatacc agggtgaagt gagaaaaggt    6600
cccgaacact tccctaggat ccctgtgaag gtggccaagt atatacccca agccagtgct    6660
gggcgtaggt ccagtgtgct ctggcagtga tggaacccta ggaaattgtg gaggaagggt    6720
aggctcagag caagggaagc tggggtgggg cacaggcaa tgcagtgccc ctggttcagg     6780
tggaggacag acctgttttc caaggcccaa taaggatcca tgtgatcttt gagtgtagtg    6840
tgtatgttgg ttggtgattg ttccaaaggt tctttgaggt gattttcggg gatctctggc    6900
atatccgtca ggttaaactc cacggttttc ctcctcactt gagatacttc tgggtgctcc    6960
atcaaggccc catcgctctc tgagagcaat tcaaaacttt tcttggcccc agaactcaca    7020
gtctttaagc ttttgtcttt ggtgtctatg cctgtgacac tgtgaagctt tgacggcgct    7080
gatggttcta gggggaagaa catgggagtg gggctgaggg gcgtctgtgg ggcactgtag    7140
tagcctggcc tctgatacag tggggcagac ttgaaggcgt ccacagcctt aagcttccag    7200
gccttgttgt cttcctggcc cctaacgttc tgtttggctg ccttgtggtt tttgggcagg    7260
ccctcgtgga gaagggattc cctcttgggc cacagtagtt tggtccttga gtttgccctg    7320
ggaggatggt gatcatggga ctgcaggcct aggaagcggc caatgatgcc agcgtgagca    7380
tcctcctcgt cctcctga                                                  7398
```

<210> SEQ ID NO 20
<211> LENGTH: 4
<212> TYPE: DNA
<213> ORGANISM: Artificial sequence
<220> FEATURE:
<223> OTHER INFORMATION: Highly Conserved DNA Sequence

<400> SEQUENCE: 20 tata                                                                    4

```
<210> SEQ ID NO 21
<211> LENGTH: 5
<212> TYPE: DNA
<213> ORGANISM: Artificial sequence
<220> FEATURE:
<223> OTHER INFORMATION: Highly Conserved DNA Sequence

<400> SEQUENCE: 21 ccaat                                                                     5

<210> SEQ ID NO 22
<211> LENGTH: 4
<212> TYPE: DNA
<213> ORGANISM: Artificial sequence
<220> FEATURE:
<223> OTHER INFORMATION: Highly Conserved DNA Sequence

<400> SEQUENCE: 22 cacc                                                                      4

<210> SEQ ID NO 23
<211> LENGTH: 4
<212> TYPE: DNA
<213> ORGANISM: Artificial sequence
<220> FEATURE:
<223> OTHER INFORMATION: Highly Conserved DNA Sequence

<400> SEQUENCE: 23 cacc                                                                      4

<210> SEQ ID NO 24
<211> LENGTH: 6
<212> TYPE: RNA
<213> ORGANISM: Artificial sequence
<220> FEATURE:
<223> OTHER INFORMATION: RNA Regulating Translation and Stability of
      mRNAs Coding for Proteins Involved in Iron Metabolism
<220> FEATURE:
<221> NAME/KEY: misc_feature
<222> LOCATION: (6)..(6)
<223> OTHER INFORMATION: n is a, c, g, or u

<400> SEQUENCE: 24 cagugn                                                                    6

<210> SEQ ID NO 25
<211> LENGTH: 6
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n = a or g or c or t

<400> SEQUENCE: 25 cagtgn                                                                    6

<210> SEQ ID NO 26
<211> LENGTH: 5
<212> TYPE: DNA
<213> ORGANISM: Homo sapiens

<400> SEQUENCE: 26 cagtg                                                                     5

<210> SEQ ID NO 27
```

```
<211> LENGTH: 337
<212> TYPE: DNA
<213> ORGANISM: Homo sapiens

<400> SEQUENCE: 27
ctgtgattcc aaatattacg taaatacact tgcaaaggag gatgttttta gtagcaattt      60
gtactgatgg tatggggcca agagatatat cttagaggga gggctgaggg tttgaagtcc    120
aactcctaag ccagtgccag aagagccaag gacaggtacg gctgtcatca cttagacctc    180
accctgtgga gccacaccct agggttggcc aatctactcc caggagcagg gagggcagga    240
gccagggctg ggcataaaag tcagggcaga gccatctatt gcttacattt gcttctgaca    300
caactgtgtt cactagcaac ctcaaacaga caccatg                             337
```

METHOD FOR REGULATING PRODUCTION OF HEMOGLOBIN BETA CHAINS

CROSS REFERENCE TO RELATED APPLICATIONS

This application is a continuation-in-part of U.S. patent application Ser. No. 10/003,669 filed Nov. 1, 2001, now U.S. Pat. No. 7,517,699, the entire contents of which are hereby incorporated by reference. This application is also a continuation-in-part of U.S. Ser. No. 11/369,179 filed Mar. 6, 2006, now U.S. Pat. No. 7,718,699 issued May 18, 2010; which claims benefit under 35 U.S.C. 119(e) of provisional application U.S. Ser. No. 60/658,803, filed on Mar. 4, 2005.

STATEMENT REGARDING FEDERALLY SPONSORED RESEARCH OR DEVELOPMENT

Not applicable.

BACKGROUND

1. Field of Invention

The present invention relates generally to the fields of molecular biology, pharmacology and to gene therapy. More particularly, it concerns methods and compositions comprising ferritin-H for regulation of genes related to iron metabolism. and regulation, and for treatment of various diseases, including neurodegenerative diseases and neuromuscular diseases.

2. Background of the Invention

Hemoglobin comprises four protein chains, two alpha chains and two beta chains ($\alpha_2\beta_2$), interwoven together, each with its own molecule of iron and with a combined molecular weight of about 68 kD. The hemoglobin macromolecule is normally glycosylated and upon absorbing oxygen from the lungs transforms into oxyhemoglobin ($HbO_2$). There are at least six distinct forms of hemoglobin, each expressed at various times during development. Hemoglobin in the embryo is found in at least three forms, Hb-Gower 1 ($\zeta_2\epsilon_2$), Hb-Gower 2 ($\alpha_2\epsilon_2$), and Hb-Portand ($\zeta_2\gamma2$). Hemoglobin in the fetus comprises nearly totally HbF ($\alpha_2\gamma_2$), whereas hemoglobin in the adult contains about 96% HbA ($\alpha_2\beta_2$), about 3% $HbA_2$ ($\alpha_2\delta_2$) and about 1% fetal HbF ($\alpha_2\gamma_2$). The embryonic switch of globin expression from $\zeta$- to $\alpha$- and from $\epsilon$- to $\gamma$- begins in the yolk sac. However, chains of embryonic $\zeta$- and $\epsilon$- have been found in the fetal liver and complete transition to the fetal form does not occur until late in fetal development. The fetal switch from $\gamma$- to $\beta$- begins later in erythropoiesis with the amount of $\beta$-globin produced increasing throughout gestation. At birth, $\beta$-globin accounts for about 40% of non-$\alpha$-globin chain synthesis and thereafter continues to rapidly increase.

Defects or mutations in globin chain expression are common. Some of these genetic mutations pose no adverse or only minor consequences to the person; however, most mutations prevent the formation of an intact or normal hemoglobin molecule through a functional or structural inability to effectively bind iron, an inability of the chains or chain pairs to effectively or properly interact, an inability of the molecule to absorb or release oxygen, a failure to express sufficient quantities of one or more globin chains or a combination of these malfunctions. For example, substitution of valine for glutamic acid at the sixth position of the $\beta$ chain produces HbS hemoglobin and was found to occur in about 30% of black Americans. In the HbS heterozygote, only about 40% of total hemoglobin is HbS with the remainder being the more normal HbA.

In studies of hemoglobin, "Hb" refers to hemoglobin. HbA refers to normal adult hemoglobin, HbF refers to fetal hemoglobin, and HbS refers to sickling hemoglobin.

Background for Sickle Cell Disease:

Upon deoxygenation, HbS hemoglobin molecules undergo aggregation and polymerization ultimately leading to a morphological distortion of the red cells which acquire a sickle or holly-leaf shape. Sickling has two major consequences, a chronic hemolytic anemia and an occlusion of small blood vessels that result in ischemic damage to tissues. Further, when exposed to low oxygen tensions, polymerization converts HbS hemoglobin from a free-flowing liquid to a viscous gel. Consequently, the degree of pathology associated with sickle cell anemia can be correlated with the relative amount of HbS in the patient's system.

Individuals with severe sickle cell anemia develop no symptoms until about five to six months after birth. In these infants it was determined that fetal hemoglobin did not interact with HbS hemoglobin and, as long as sufficient quantities were present, could modulate the effects of HbS disease. This modulating effect of $\gamma$-globin is also observed with other $\beta$-globin disorders, such as HbC and HbD, and other mutations of the $\beta$ chain. HbS polymerization is also significantly affected by the hemoglobin concentration of the cell. The higher the HbS hemoglobin concentration, the greater the chances for contact between two or more HbS hemoglobin molecules. Dehydration increases hemoglobin concentration and greatly facilitates sickling.

The average sickled red blood cell survives for about 20 days or less in the body, as compared to the 120-day life span of a normal red blood cell. Individuals with HbS syndromes have frequent infections, chronic hemolysis with a striking reticulocytosis and hyperbilirubinemia. The course of the disease is typically punctuated with a variety of painful crises called vaso-occlusive crises. These crises represent episodes of hypoxic injury and infarction in the organs, abdomen, chest, extremities or joints. Leg ulcers are an additional manifestation of the vaso-occlusive tendency of this disease. Central nervous system involvement is common producing seizures and even strokes. Aplastic crises, also common, represent a temporary cessation of bone marrow activity and may be triggered by infections, folic acid deficiency or both. Crises are episodic and reversible, but may be fatal. Damage from crisis episodes tends to be cumulative and even in those individuals with milder forms of sickle cell disorder, lifespans can be greatly reduced.

Many current research and experimental treatment efforts are aimed at the processes that cause red blood cells to sickle. Hydroxyurea has been found to stimulate the production of fetal hemoglobin, a type of hemoglobin found in the fetus and small infants, which is able to block the sickling action of red blood cells. Human Genome Research Institute indicates that those treated with hydroxyurea need fewer blood transfusions and have fewer attacks of acute chest syndrome. The University of Maryland states that it is "currently the only agent in general use to prevent acute sickle-cell crises" but has no effect on 25 percent of patients and cannot be used during pregnancy.

Some current research efforts to treat sickle cell disease involve correcting the defective hemoglobin gene and inserting it into the bone marrow of those with sickle cell to stimulate production of normal hemoglobin. For example, researchers from Harvard Medical School and MIT, with support from the National Institutes of Health, were able to correct sickle cell disease in mice using this approach in 2001. Researchers used bioengineering to create mice with a human gene that produces the defective hemoglobin causing sickle cell disease. Bone marrow containing the defective hemoglobin gene was removed from the mice and genetically "corrected" by the addition of the anti-sickling human β-hemoglobin gene. The corrected marrow was then transplanted into other mice with sickle cell disease. The genetically corrected mice began producing high levels of normal red blood cells and showed a dramatic reduction in sickled cells. Scientists are hopeful that the techniques can be applied to human gene transplantation using autologous transplantation, in which some of the patient's own bone marrow cells would be removed and genetically corrected. However, additional research and development is required before this gene therapy approach is applicable in human. Furthermore, this approach can only reach a very small number of patients because of the high cost and that the technological complexities involved in gene therapy and stem cell (bone marrow cell, cord blood stem cell, etc) transplant require that these procedures are performed in a major health research center.

Background for Thalassemia:

The thalassemia syndromes are a heterogenous group of disorders all characterized by a lack of or a decreased synthesis of the globin chains of HbA. Deficiencies of β-globin expression are referred to as β-thalassemias and deficiencies of αZglobin, α-thalassemias. The hemolytic consequences of deficient globin chain synthesis result from decreased synthesis of one chain and also an excess of the complementary chain. Free chains tend to aggregate into insoluble inclusions within erythrocytes causing premature destruction of maturing erythrocytes and their precursors, ineffective erythropoiesis, and the hemolysis of mature red blood cells. The underlying defects of hemoglobin synthesis have been elucidated over the years and largely reside in the nucleic acid sequences which express or control the expression of α- or β-globin protein.

Mammalian globin gene expression is highly regulated during development. The human beta-globin gene cluster includes one embryonic gene, epsilon (ε), two adult beta globin genes, beta (β) and delta (δ), two fetal beta globin genes G-gamma (G-γ) and A-gamma (A-γ), which differ by only one amino acid, and at least one pseudo-beta gene, psi beta (ψβ). All are expressed from a single 43 kilobase segment of human chromosome 11. Fetal beta type globin, or γ-globin, is expressed in the earliest stages of mammalian development and persists until about 32 to 34 weeks of gestation. At this stage, the adult forms of β-globin begin to be expressed and substitute for the fetal proteins.

Each β-globin gene comprises three exons which encode about 146 amino acids, two introns and a 5'-untranslated region containing the promoter sequences. Biosynthesis of β-globin begins with transcription of the entire gene followed with RNA processing of the message, removal of the introns by splicing, poly-A addition, capping and post-transcriptional modifications. The mature mRNA molecule is exported from the nucleus and translated into β-globin. Defects in each of these functions have been found associated with specific thalassemias. Identified mutations include single-nucleotide deletions, insertions and substitutions, frame shift mutations, deletions of entire segments of coding or controlling regions, improper termination signals, aberrant splicing signals, and multiple mutations. β°-thalassemias are characterized by a complete absence of any β-globin chains; β⁺-thalassemias are characterized by a detectable presence of a reduced amount of β chains.

There are three principal categories of β-thalassemia, thalassemia major, thalassemia intermedia and thalassemia minor. Patients with thalassemia minor may be totally asymptomatic and are genotypically $\beta^+/\beta$ or $\beta^\circ/\beta$. Although red cell abnormalities can be detected, symptoms are mild. Thalassemia intermedia patients are most often genotypically $\beta^+/\beta^+$ or $\beta^\circ/\beta$ and present severe symptoms which can be alleviated with infrequent blood transfusions. In contrast, thalassemia major patients are genotypically $\beta^\circ/\beta^\circ$, $\beta^\circ/\beta^+$ or $\beta^+/\beta^+$, and require regular and frequent transfusions. Children suffer from severe growth retardation and die at an early age from the profound effects of anemia. Those that survive longer suffer from morphological changes. The face becomes distorted due to expansion of marrow within the bones of the skull, hepatosplenomegaly ensues, there is a delayed development of the endocrine organs including the sexual organs, and a progressive iron overload with secondary hemochromatosis.

There are two direct consequences of β-thalassemia. First, there is an inadequate formation of HbA and, therefore, an impaired ability to transport oxygen. There are also multiple effects attributable to an imbalance between α- and β-chain syntheses. Surprisingly, the pathological consequences of globin chain imbalance appear to be the more severe. Free α chains form unstable aggregates that precipitate within red cell precursors in the form of insoluble inclusions. These inclusions damage cellular membranes resulting in a loss of potassium. The cumulative effect of these inclusions on the red blood cells is an ineffective erythropoiesis. An estimated 70% to 85% of normoblasts in the marrow are eventually destroyed. Those that do escape immediate destruction are at increased risk of elimination by the spleen where macrophages remove abnormal cells. Further, hemolysis triggers an increased expression of erythropoietin which expands populations of erythroid precursors within bone marrow and leads to skeletal abnormalities. Another severe complication of β-thalassemia is that patients tend to have an increased ability to absorb dietary iron. As most treatments for thalassemia involve multiple transfusions of red blood cells, patients often have a severe state of iron overload damaging all of the organs and particularly the liver. To reduce the amount of iron in their systems, iron chelators are typically administered. Although helpful, patients succumb at an average of between about 17 to 35 years of age to the cumulative effects of the disease and iron overload.

Genotypic variations in healthy individuals have been identified wherein adult βZglobin is not formed, but severe complications are avoided. These patients constituitively express fetal or γ-globin protein in amounts sufficient to substitute for the missing β-globin protein. This hereditary persistence of fetal hemoglobin (HPFH) involves one or both of the fetal beta globin genes, A-γ and G-γ. Apparently, consistent production of either γ-globin protein accomplishes the necessary functions of the abnormal or missing β-globin protein.

Background for Skin Cancer and Other Cancers:

Ultraviolet (UV) light is known to be damaging to human skin and has been implicated in the etiology of skin cancers. Recent studies have revealed that ferritin is elevated in cultured skin cells exposed to UV light, and it has been postulated that the increased ferritin represents the skin cell's attempt to protect itself from free radical damage by binding and sequestering iron which could, in turn, cause oxidative and free radical-mediated damage.

The rationale for other cancers is similar. Iron has been implicated as an etiologic agent in skin cancer, hepatomas (liver cancer), renal cell carcinoma (kidney cancer), neuroblastomas, leukemias, and breast cancer. Ferritin-H, an iron chelator, is protective against carcinogenic events in cells that give rise to all of these cancers. When human skin is treated in such a way as to transfect them with a ferritin-H subfamily peptide or gene that expresses the peptide, protection from UV-induced damage is provided to the cells. Ferritin-H-subfamily peptides are thought to be superior in this regard since they can sequester iron and not release it readily and can do so without altering normal aspects of the cells iron metabolism and other functions. Ferritin-L-subfamily peptides, on the other hand, are likely to cause even more harm in that they readily give up iron which exacerbates the problem by increasing free iron and radical generation. Thus, delivering a ferritin-H-subfamily peptide or a gene (expression clone) for the peptide to the target cells is protective and/or corrective of events that lead to cancer. Similarly, agents that activate the endogenous ferritin-H-subfamily gene or genes are also beneficial.

It is realized that all human ferritins, even those highly enriched in ferritin-L, require a small amount of ferritin-H and its associated ferrooxidase activity to carry out the functions of iron storage and release. It is the balance between ferritins L and H that is critical. Increasing the balance in favor of ferritin-H, even to the point of great excess of ferritin-H, appears to mediate a cell's return to healthy iron management.

Background for Neurodegenerative Diseases:

The distribution of free iron and of ferritin both change during brain development in animals and humans. Increased iron is found in the basal ganglia, beginning early in the disease process, in both Parkinson's disease and Huntington's disease. There is an increase in iron in several areas of the brain in Alzheimer's disease, in other dementias, and in aging; and the distribution of isoferritins in a variety of brain areas is different and changes in the above diseases. Ferritin-H, but not ferritin-L, is present in the nucleus of neuronal cells in the cortex of developing rat brains and is protective against oxidative damage that is caused by free iron. Rationale: Ferritin-H decreases in critical brain cells during aging and neurodenerative diseases, whereas free iron and iron released from localized ferritin-L are implicated in oxidative damage in diseases and dementia. Ferritin-H or a related subfamily peptide is protective against a variety of neurodegenerative changes associated with aging, the above diseases and dementias. Likewise, an expression clone of a ferritin-H-subfamily gene and/or a regulator of ferritin-H-subfamily genes, if delivered to the appropriate brain area and to specific cells, is predicted to be protective.

Background for Friedreich's Ataxia and Related Neuromuscular Disorders:

Deletion of YDL120, the yeast homologue of the human gene responsible for Friedreich's ataxia, elicits decreased cellular respiration associated with decreased cytochrome c oxidase activity and, in certain nuclear backgrounds, mitochondrial DNA is lost. In the null mutants, the cellular growth is highly sensitive to oxidants, such as $H_2O_2$, iron and copper; and ferrous sulfate elicits loss of mitochondrial DNA. Mitochondria of the null mutants contain ten times more iron than wild-type. The neurodegeneration observed in Friedreich's ataxia can be well explained on the basis of a mitochondrial iron overload responsible for an increased production of highly toxic free radicals. Rationale: Since iron accumulation is implicated in the etiology of Friedreich's ataxia, both the initial appearance of symptoms and the progression of this disease are slowed or halted by sequestering the free iron. Transfection of ferritin-H-subfamily peptides or expression clones and/or treatment with agents that up-regulate expression of the endogenous ferritin-H-subfamily genes are ameliorative.

Background for Atherosclerosis:

Strong epidemiological evidence is available that iron (i.e., iron excess) is an important factor in the process of atherosclerosis and that iron depletion has cardiovascular benefits and protects against ischemic heart disease. Iron-catalyzed generation of free radicals contributes to vessel wall damage, to plaque formation and, by both mechanisms, to cardiac vessel damage. Once again, intracellular iron release from ferritin-L is implicated as a source of the iron contributing to this etiology; ferritin-H is protective by chelating and sequestering the free and released iron. Rationale: Transfecting the appropriate cell with a ferritin-H subfamily peptide or gene expression clone or with a gene regulator that activates the endogenous ferritin-H subfamily gene(s) in artery wall cells or cellular elements of atherosclerotic plaques prevents or reverses artery blockage.

What is needed is an elucidation of the mechanism of developmental hemoglobin (Hb) switching which allows the reactivation of fetal Hb in adult humans, a manipulation that alleviates the clinical manifestations of sickle cell disease, β-thalassemia, and related diseases. Inactivation of the mutated form of the adult β-globin gene that causes sickle cell disease is also of clinical value, since it results in a compensatory increase in fetal γ-globin expression.

SUMMARY OF THE INVENTION

The present invention is directed to a method for repressing production of βZglobin protein and increasing production of γ-globin protein in a human cell, the method having the following steps. At least one human β-globin producing cell is provided, and a ferritin-H protein is provided. The at least one human β-globin producing cell is contacted with the ferritin-H protein, whereby the ferritin-H protein is introduced into the at least one human β-globin producing cell to repress production of β-globin and increase production of γ-globin protein in the human β-globin producing cell.

An embodiment of the present invention for repressing production of β-globin protein and increasing production of γ-globin protein in a human cell includes the following steps. At least one human β-globin producing cell is provided. A nucleic acid segment encoding a ferritin-H protein is introduced into the at least one human β-globin producing cell, whereby the cell produces ferritin-H protein. The ferritin-H protein so produced represses production of βZglobin protein and increases production of γ-globin protein in the human β-globin producing cell.

Another embodiment of the present invention for repressing production of β-globin protein and increasing production of γ-globin protein in a human cell includes providing at least one human β-globin producing cell and providing an exogenous ferritin-H inducer. The at least one human β-globin producing cell is contacted with the exogenous ferritin-H inducer, whereby the exogenous ferritin-H inducer elevates production of ferritin-H in the at least one human βZglobin producing cell to repress production of β-globin and increase production of γZglobin protein in the human β-globin producing cell.

The present invention also includes a method for treating sickle cell disease, the method having the following steps. Blood is obtained from a sickle cell patient and cells in the blood are cultured to produce erythroid precursor cells wherein the hemoglobin phenotype of the erythroid precursor cell is HbS. A ferritin-H protein is provided and the erythroid precursor cells are contacted with the ferritin-H protein, whereby the ferritin-H protein is introduced into the erythroid precursor cells. The erythroid precursor cells are then cultured for a length of time sufficient to change the hemoglobin phenotype of at least a portion of the erythroid precursor cells from HbS to HbF as the erythroid precursor cells mature. The maturing erythroid precursor cells are reinfused back to the sickle cell patient.

Another method for treating sickle cell disease comprises the following steps. Blood is obtained from a sickle cell patient and cells in the blood are cultured to produce erythroid precursor cells wherein the hemoglobin phenotype of the erythroid precursor cell is HbS. A nucleic acid segment encoding a ferritin-H protein is introduced into the erythroid precursor cells, whereby ferritin-H protein is produced in the erythroid precursor cells. The erythroid precursor cells are then cultured for a length of time sufficient to change the hemoglobin phenotype of at least a portion of the erythroid precursor cells from HbS to HbF as the erythroid precursor cells mature. The maturing erythroid precursor cells are then reinfused back to the sickle cell patient.

Yet another method for treating sickle cell disease comprises the following steps. Blood is obtained from a sickle cell patient and cells in the blood are cultured to produce erythroid precursor cells wherein the hemoglobin phenotype of the erythroid precursor cell is HbS. An exogenous ferritin-H inducer is provided and the erythroid precursor cells are contacted with the exogenous ferritin-H inducer, whereby the exogenous ferritin-H inducer elevates production of ferritin-H protein in the erythroid precursor cells. The erythroid precursor cells are then cultured for a length of time sufficient to change the hemoglobin phenotype of at least a portion of the erythroid precursor cells from HbS to HbF as the erythroid precursor cells mature. The maturing erythroid precursor cells are then reinfused back to the sickle cell patient.

The present invention also provides a transgenic mouse whose genome comprises a gene encoding human ferritin-H operably linked to a human β-globin promoter, wherein the transgenic mouse exhibits a mild β-thalassemia phenotype when compared to a wild-type mouse.

Other features and advantages of the present invention will be readily apparent to those skilled in the art upon a reading of the description of preferred embodiments which follows.

BRIEF DESCRIPTION OF FIGURES

FIG. 3A shows the 95 bp Rsa fragment (−222/−128) and two ds-oligos that overlap this same region (−164/−128 and −232/−188), that were each end-labeled and used as substrates for binding, using the antibody super-shift assay and crude K562 cell nuclear extract.

FIG. 3B shows a mobility shift assay. The super-shift band (arrow) was observed with the Rsa fragment and with the −164/−128 oligo, but not with the −232/−188 oligo, indicating that the binding site for nuclear ferritin is between −164 and −128 of the β-globin promoter.

FIG. 4A shows sequences of wildtype [SEQ ID NO: 1] and mutant oligonucleotides no. 1-4 [SEQ ID NOs: 2-5, respectively] corresponding to the 5' binding region mapped in FIG. 3A. Mutated nucleotides and the original CAGTGC [SEQ ID NO: 6] sequence are underlined. These oligos, used in the competitive gel shifts in FIGS. 4B, 4C, and 4D, were double-stranded; only the top strands are shown.

FIG. 4B shows competition gel-shift assays using the end-labeled wt sequence versus unlabeled wt or mutant no. 4 oligonucleotides, with partially purified ferritin-protein from K562 nuclei. Unlabeled oligonucleotides in the fold excesses shown were present with the labeled wt sequence at the time binding was initiated. Whereas the wt sequence competes significantly with itself at 50-fold excess, the oligonucleotide mutated in the CAGTGC [SEQ ID NO: 6] sequence requires 1,000-fold excess to give the same level of competition. Labels: p, probe; sb, shift band; w, wells.

FIG. 4C shows the relative optical densities of the shift bands plotted versus molar excess of competitors, for the gel in FIG. 4B.

FIG. 4D illustrates that molar excesses of wildtype and mutant oligonucleotides were required to produce 50% inhibition of binding of the labeled probe. Each mutant oligonucleotide required about the same molar excess as the wt sequence to produce 50% inhibition except mutant no. 4 (mutated in the −153/−148 CAGTGC [SEQ ID NO: 6] sequence), which required a 20-fold greater concentration to compete to the same ex-tent, indicating that CAGTGC [SEQ ID NO: 6] is crucial for the DNA-protein interaction.

FIG. 5 shows a multiple sequence alignment of mammalian β-globin promoters, showing the high degree of conservation of the CAGTGC [SEQ ID NO: 6] motif. Promoter sequences (corresponding to −162/+1 of the human β-globin gene) were aligned for 12 mammalian species, namely human, gorilla, macaca, bovine, goat, sheep, galago, tarsius, lepus, rabbit, rat and mouse, corresponding to SEQ ID NOS. 7-18, respectively. GenBank accession nos. for the sequences are (from top down) V01317, X61109, X05665, X00376, M15387, X14727, M1740, J04429, Y00347, M11818, X15009, and X14061 [SEQ ID NOs: 7-18, respectively]. Alignments were generated by using the programs PILEUP and LINEUP.

FIG. 6 shows co-transfection experiments demonstrating that ferritin-H loses its ability to repress if the β-globin promoter contains a mutated ferritin binding site. Cotransfection experiments demonstrating ferritin-H repression of the β-globin promoter and loss of ability to repress when the ferritin binding site (CAGTGC [SEQ ID NO: 6]) is mutated. Transfections of CV-1 cells were performed with a constant amount (6 μg) of total plasmid DNAs mixed with 8 μl of DMRIE-C added to 2×10$^6$ CV-1 cells, such that each transfection had 2 μg of β-CAT plasmid (W=wt, or M=mutant), ±1 μg of EKLF, ±3 μg of ferritin-H expression plasmid (FH), with the difference made up to 6 μg with pEGFP. Reporter gene activity, expressed as ng of CAT per mg of cellular protein (measured by ELISA), is shown for the following combinations with either native (W) or mutant (M) β-CAT plasmids: the nonstimulated human β-globin promoter (open bars); the β-globin promoter stimulated by a cotransfected EKLF effector plasmid (hatched bars); and EKLF-stimulated β-globin promoter cotransfected with a ferritin-H expression plasmid (solid bars). (n=3 transfections per data set; bars=SEM). Construction of reporter plasmids is diagrammed above the histogram.

FIG. 14 illustrates that confocal microscopy reveals that transiently transfected GFP-FtH fusion protein localizes to the nucleus of CV-1 cells. (a) Confocal sections with filters for DAPI stain for DNA (red), GFP-FtH (green), and the merged images (yellow) (b) Quantitative micro-fluorescence spectroscopy across the length of a nucleus (white line) as shown by tracings of the fluorescence intensity at two specific wavelengths. The valley in the tracings represents the nucleolus which remained unstained.

FIG. 16A illustrates the transfection of K562 cells with an Alexa488-labeled anti-sense single-stranded DNA oligonucleotide to ferritin-H mRNA. Ninety percent of the cells show the yellow-green fluorescence in the nucleus.

FIG. 18 illustrates that ferritin-H represses the mouse β-major globin gene in transgenic mice. (a) Schematic diagram of the human ferritin-H construct used for creation of ferritin transgenics. (b) UT PAGE electrophoresis of globin chains from a ferritin-H transgenic mouse (lane 1), a non-transgenic mouse (lane 2), and globin standards (lane 3). The ratio of β-major to β-minor globin is decreased in the ferritin-H transgenic mouse because the human ferritin-H binds the CTGTGC sequence [SEQ ID NO: 6] in the β-major promoter but cannot bind the β-minor promoter which has no ferritin-H binding motif. (c) Blood smears from a non-transgenic mouse (wt) and a transgenic mouse (FtH-Tg). The FtH-Tg mice appear to have a mild β-thalassemia characterized by increased numbers of target cells (arrow) indicative of inclusions due to precipitated excess alpha-chains. There would be no excess alpha-chains in humans treated with ferritin-H because, unlike the mouse, humans respond to β-globin repression with increased γ-globin synthesis.

FIG. 23 illustrates HPLC spectra documenting ferritin-H induction of HbS-to-HbF switching in erythroid cell precursor cells from sickle cell disease patients by ferritin-H protein (F), ferritin-H vector (E), or ferritin-H inducer (C). HbF production induced by ferritin-H was pancellular as indicated in the microphotographic inserts of immuno-HbF fluorescence, whereas HbF production by erythropoietin (Epo) alone (H) was less and was expressed in a minority of erythrocytes. (G) TGFβ, a known inducer of ferritin-H, in combination with stem cell factor (SCF) produces a partial switch to HbF; the amount of HbF is not as great as with ferritin-H, and these agents (SCF and TGFβ) cannot be used in human patients because of side-effects including the possibility of tumorigenesis.

FIG. 24 illustrates that FITC-labeled ferritin-H is taken-up by human erythroid precursor cells, as revealed by fluorescence microscopy.

FIG. 25 illustrates fluorescence microscopy of human erythroblasts cells taking up FtH-FITC from the medium in 1 hour at 37 degrees C., without (B & C) or with the aid of a protein transfection reagent (D).

DETAILED DESCRIPTION OF THE INVENTION

Figure 1:
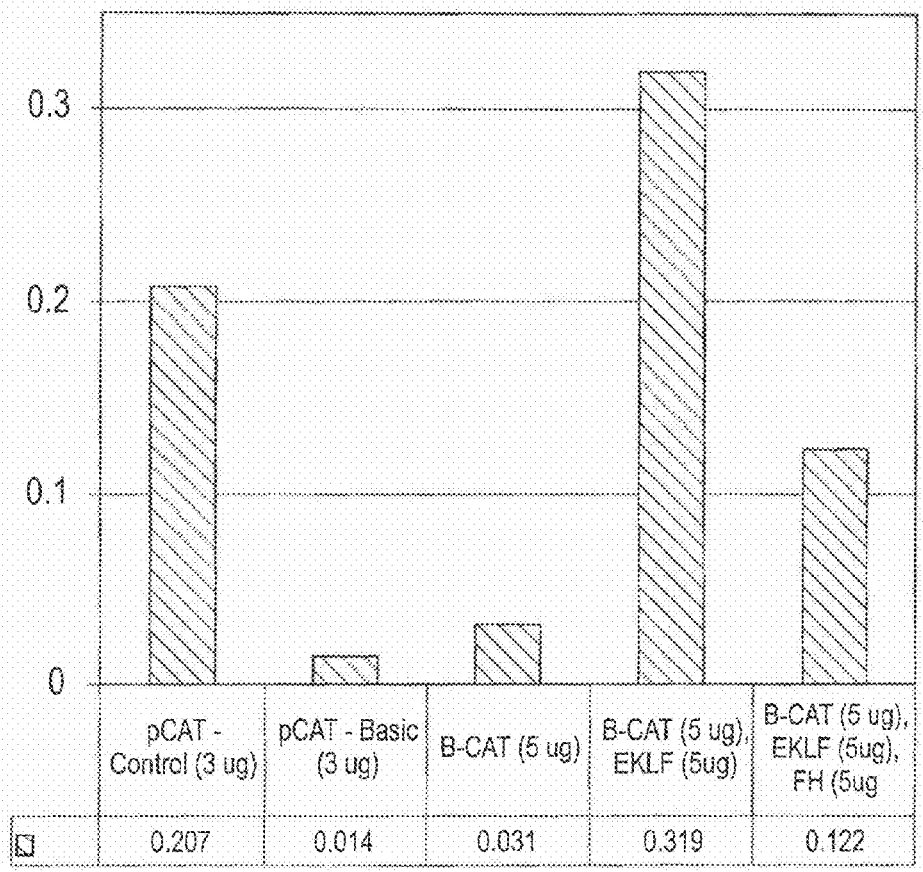
FIG. 1 shows ferritin-H repression of the β-globin promoter in co-transfected CV-1 cells. Transient expression of a reporter gene encoding chloramphenicol acetyl transferase (CAT), expressed as ng CAT/mg cellular protein measured by an ELISA as described under Materials and Methods, is shown for CV-1 cells transfected with the following CAT plasmids (from left to right): CAT driven by an activated SV40 promoter (pCAT-Control vector), CAT plasmid with no promoter (pCAT-Basic vector), the non-stimulated human β-globin promoter (B-CAT), the β-globin promoter stimulated by a co-transfected EKLF effector plasmid (B-CAT, EKLF), and EKLF-stimulated β-globin promoter co-transfected with a ferritin-H expression plasmid (B-CAT, EKLF, FH). The reporter gene expression was repressed 62% by the presence of the co-transfected ferritin-H expression vector.

Before explaining at least one embodiment of the invention in detail by way of exemplary drawings, laboratory procedures, experimentation, and results, it is to be understood that the invention is not limited in its application to the details of construction and the arrangement of the components set forth in the following description or illustrated in the drawings, laboratory procedures, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients. As utilized in accordance with the present disclosure, the following terms, unless otherwise indicated, shall be understood to have the following meanings: The terms "sickle cell anemia" or "sickle cell disease", as used herein, refer to any symptomatic anemic condition which results from sickling of red blood cells.

The term "thalassemia" as used herein refers to hereditary anemia that occurs due to mutations affecting the synthesis of hemoglobin. In "mild β-thalassemia", the lack of a normal β-globin is not great enough to cause problems in the normal functioning of the hemoglobin. An animal with mild β-thalassemia usually experiences no health problems other than a mild anemia.

The terms "treat", "treating" and "treatment", as used herein, are understood to include reduction or completely resolution of symptoms of a disease, and/or prevention of the onset or development of a disease.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The terms "nucleic acid" or "polynucleotide", as used herein, refer to two or more naturally occurring or non-naturally occurring deoxyribonucleotides or ribonucleotides linked by a phosphodiester linkage, or by a linkage that mimics a phosphodiester linkage to a therapeutically useful degree. A nucleic acid may be double stranded, single stranded, or contain portions of both double stranded or single stranded sequence.

The term "gene" as used herein refers to a nucleic acid segment involved in producing a polypeptide, that may or may not include regions preceding and following the coding region, e.g. 5' untranslated (5' UTR) and 3' UTR, as well as introns between exons.

A "functional derivative" of a polypeptide is a compound having a biological activity (either structural or functional) substantially similar to the polypeptide. The term "functional derivative" is intended to include the fragments, variants, analogs, or chemical derivatives of a molecule. Functional derivatives of a polypeptide include, but are not limited to, fragments of the polypeptides from any species, and covalent modifications of a native polypeptide, provided that they have a biological activity in common with a corresponding native polypeptide.

A "fragment" of a molecule is meant to refer to any subset of the molecule.

A "variant" of a molecule is meant to refer to a molecule substantially similar to either the entire molecule or a fragment thereof. Variants of a polypeptide include, but are not limited to, mutations of the polypeptide. Such mutations include, for example, but not by way of limitation, deletions, insertions or substitutions of residues within the polypeptide. Any combination of deletion(s), insertion(s), and substitution(s) may also be made to arrive at the final variant, provided that the final variant possesses the desired activity.

An "analog" of a molecule is meant to refer to a non-natural molecule substantially similar to either the entire molecule or a fragment thereof.

A "chemical derivative" of a molecule is meant to refer to a molecule including additional chemical moieties not in the native molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in Remington's Pharmaceutical Sciences (1980). Procedures for coupling such moieties to a molecule are well known in the art.

"Percentage of sequence identity" as used herein is determined by comparing two optimally aligned polynucleotide or polypeptide sequences, where the fragments of one sequence may comprises additions or deletions (e.g., gaps or overhangs) as compared to the other sequence (which does not comprise additions or deletions) for optimal alignment of the two sequences. The percentage is calculated by determining the number of positions at which the identical nucleotide or amino acid occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by manual inspection.

Typically, greater than 50% of sequence identity between two polypeptides is considered to be an indication of similarity in biological function. Variants of a polypeptide having a percentage of sequence identity greater than 50% are classified as functional derivatives of the polypeptide. Preferably, functional derivatives of a polypeptide have a percentage of sequence identity of greater than 60%, 70%, 80%, 90%, 95%, 98% or 99%, respectively.

The term "vector" as used herein refers to a nucleic acid construct designed for transfer between different host cells.

Vectors can be generated recombinantly or synthetically and can be, for example, but not by way of limitation, a plasmid, chromosome, mitochondrial DNA, plastid DNA, virus, or nucleic acid fragment.

An "expression vector" as used herein refers to a vector that has the ability to incorporate and transcribe a particular gene in a target cell. Typically, an expression vector includes, among other sequences, a gene to be transcribed and a promoter. Many prokaryotic and eukaryotic expression vectors are commercially available. Selection of appropriate expression vectors is within the knowledge of those having skill in the art.

The term "plasmid vector" as used herein refers to a circular double-stranded (ds) nucleic acid construct used as a vector, and said circular double-stranded nucleic acid construct containing a particular gene to be transcribed. A plasmid vector forms an extrachromosomal self-replicating genetic element in many bacteria and some eukaryotes.

The term "viral vector" as used herein refers to a recombinant virus that has some genes in the native virus genome removed such that the recombinant virus is replication-incompetent, and said recombinant virus containing a particular gene to be transcribed. Representative viral vectors include retroviruses, adenoviruses, herpes viruses and avipox viruses. Retroviral and adenoviral vectors are preferred. Lentiviral vectors and adenoviral vectors, especially type 2 and type 5 adenoviral vectors, are especially preferred.

The term "transfection reagent" as used herein refers to a compound or compounds that bind(s) to or complex(es) with polynucleotides or peptides and mediates their entry into cells. The transfection reagent also mediates the binding and internalization of polynucleotides or peptides into cells. Examples of polynucleotide transfection reagents include, but are not limited to, cationic liposomes and lipids, calcium phosphate precipitates, polylysine complexes and combinations thereof. The polynucleotide transfection reagent has a net positive charge that binds to the polynucleotide's negative charge. The transfection reagent mediates binding of polynucleotides to a cell via its positive charge (that binds to the cell membrane's negative charge) or via ligands that bind to receptors in the cell. For example, cationic liposomes or polylysine complexes have net positive charges that enable them to bind to polynucleotides. Examples of peptide transfection reagents include, but are not limited to, cationic liposomes, calcium phosphate precipitates and combinations thereof. For example, peptide-cationic liposome complex attaches to negatively charged cell surface and either can directly fuse with the membrane and deliver the captured protein into the cell or be endocytosed by the cell and then fuse with the endosome, releasing the captured peptide into the cytoplasm.

The term "inducer" as used herein refers to a molecule or a chemical capable of initiating or activating the expression of a particular gene, either directly by binding to a regulatory sequence, or indirectly via other cellular factors. It can also prevent the action of a repressor. In contrast, a "repressor" has the capacity to inhibit or block the expression of a particular gene, either directly or indirectly. The terms "ferritin-H inducer" or "inducer of Ferritin-H", refer to a molecule or a chemical capable of initiating or activating the expression of ferritin-H.

The term "endogenous" as used herein means originating within a cell.

The term "exogenous" as used herein means originating outside a cell. The term "exogenous ferritin-H inducer" as used herein refers to a ferritin-H inducer originating outside the cell to which the ferritin-H inducer is provided to initiate or activate the expression of ferritin-H.

"In vivo" is defined as performing actions inside a living human, mammal, animal, or organism.

"In vitro" is defined as performing actions outside a living human, mammal, animal, or organism.

"Ex vivo" is defined as performing actions on cells removed from a living human, mammal, animal, or organism and returning the cells back to the living human, mammal, animal, or organism.

Figure 7:
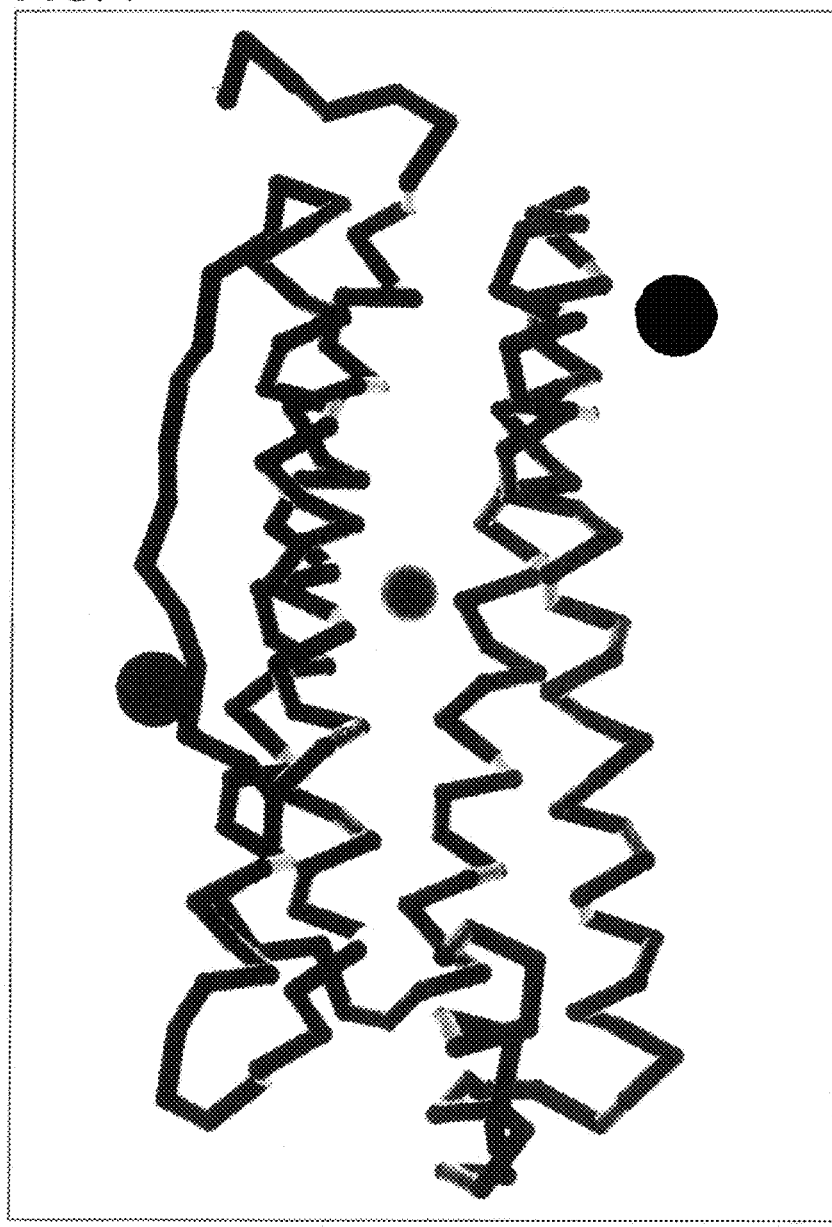
FIG. 7 shows a schematic representation of the ferritin-H protein monomer having an iron ion bound to the ferroxidase active site (center). The two dark/solid circles at the periphery represent calcium ions.

The term "operably linked" as used herein refers to functionally related nucleic acid sequences. A promoter is operably linked with a coding sequence if the promoter controls the transcription of the encoded polypeptide. Ferritin is a globular protein complex consisting of twenty-four protein subunits and is the main intracellular iron storage protein in both prokaryotes and eukaryotes, keeping iron in a soluble and non-toxic form. In vertebrates, these twenty-four protein subunits consist of two kinds: the light chain (L) and the heavy chain (H) type. The heavy chain to light chain ratio in the ferritin protein varies widely in a tissue-specific manner and may affect the rates of iron uptake and release in different tissues. FIG. 7 shows a schematic representation of ferritin-H protein having a bound iron ion. The active site responsible for ferroxidase activity has been elucidated. In the present invention, ferritin-H is shown to be also involved in regulation of gene expression of certain genes. However, the active site or sites of the ferritin-H protein responsible for transcription regulation has not been identified. In humans, a functional ferritin-H gene has been cloned, sequenced and designated as FTH1 (Hentze et al., PNAS 1986 83(19):7226-7230, incorporated herein in its entirety by reference). The DNA sequence of human FTH1 appears in the EMBL Gene Bank under the accession number DQ496108 (SEQ ID NO: 19) and is incorporated herein in its entirety by reference. Several alternatively spliced transcript variants of FTH1 have been observed (Percy et al., Analyst. 1998 123(1):41-50, incorporated herein in its entirety by reference). Mutational analysis has been performed on rat or human ferritin-H (Guo et al., Arch. Biochem. Biophys. 1998 352(1):71-77; Broxmeyer et al., PNAS 1991 88(3):770-774; both references are incorporated herein in their entirety). In humans, the ferritin-H gene also has multiple pseudogenes (Cragg et al., Hum. Genet. 1985 71(2):108-1; McGill et al., Hum. Genet. 1987 76(1):66-72; both references are incorporated herein in their entirety). Ferritin-H is only one member of the family of ferritin proteins. Ferritin-H and ferritin-L are the most studied. There are likely to be ferritin family proteins that have not yet been identified. Ferritin family proteins are generally involved in iron metabolism. Other ferritin family proteins, which are similar to ferritin-H, are also within the scope of the present invention. While certain embodiments of ferritin-H have been described herein, other embodiments of ferritin-H protein are widely known to a person of ordinary skill in the art, and therefore the present invention is not limited to the specific ferritin-H protein disclosed herein, but rather encompasses all forms of ferritin-H protein known in the art. As with all other gene regulation proteins, functional derivatives of ferritin-H regulate gene transcription as well as or better than ferritin-H itself. The term "functional derivative of ferritin-H" is defined herein as a compound which regulates gene transcription substantially similarly to ferritin-H. These functional derivatives of ferritin-H include, but are not limited to, fragments of ferritin-H proteins, any fusion proteins into which the active site or sites of ferritin-H responsible for transcription regulation has been spliced, larger transcription or translation products of a ferritin family protein, fragments of any of the ferritin family proteins, mutated ferritin-H protein with deletion(s), insertion(s), and/or substitution(s) while still retaining the ability of regulating gene expression as wildtype ferritin-H, and any mimetic proteins that repress DNA transcription by means of an active site that is substantially the same as the ferritin-H active site responsible for DNA binding and transcription regulation. The fact that the ferritin active site or sites responsible for repression of DNA transcription includes both DNA binding and protein binding sites is well known to those skilled in the art. A functional derivative of ferritin-H protein, which contains mutations when compared to the native ferritin-H protein, ordinarily is prepared by site-directed mutagenesis (as exemplified by Adelman et al., DNA 2:183 (1983)) of nucleotides in the DNA coding sequence, producing a modified coding sequence, thereafter expressing this recombinant DNA in a prokaryotic or eukaryotic host cell (see below). In another embodiment, a functional derivative of ferritin-H protein with mutations may be conveniently prepared by direct chemical synthesis, using methods well-known in the art. The inventor has previously demonstrated that ferritin-H is a repressor of the human β-globin gene (U.S. application Ser. No. 10/003,669, Publication No. US2002/0128183, incorporated herein by reference in its entirety without disclaimer), the same gene that is mutated in sickle cell disease and in some forms of β-thalassemia. The inventor has also previously demonstrated that ferritin-H is also an activator of the human fetal γ-globin gene. Thus, ferritin-H induces an HbS-to-HbF hemoglobin switch that is known from patient data to produce a phenotypic cure for sickle cell disease. The activator/repressor is a nuclear form of ferritin (Broyles et al., Colloque INSERM (1995) 234:43-51), of the ferritin H subfamily of ferritin peptides. The '669 patent application demonstrates that a ferritin family protein from human K562 erythroleukemia cell nuclear extracts (as well as pure human ferritin-H) binds to the promoter of the human β-globin gene (the promoter that drives the mutated form of the gene in sickle cell) at –150 bp from the transcription start site, in vitro. The binding is very specific to that DNA sequence. The '669 patent application also demonstrates that an expression clone of ferritin-H represses this β-globin promoter in transient co-transfection experiments. This is very reproducible in multiple experiments with two different reporter genes, with no repression seen by control/null plasmids. The '669 patent application further demonstrates that ferritin-H no longer represses if the promoter contains a mutated binding site. A β-globin promoter mutated only in the ferritin-H binding site and hooked to the same reporter gene (CAT, in this case) is used as a control plasmid. This is not only the perfect control for the transfections, but it also connects the in vitro DNA binding with in vivo function quite nicely. Since this decrease in β-globin expression is compensated by an increase in fetal γZglobin expression in human erythroids cells, and since a modest amount of this switching is known to totally ameliorate sickle cell and wholly or partially ameliorate β-thalassemias, this new finding makes ferritin useful for curing the phenotype of these classic genetic diseases.

Ferritin-H (FtH) is also a protein which can chelate iron. Thus, ferritin-H could be beneficial in treating diseases which are caused and/or characterized by increases in iron (e.g., Alzheimer's Disease, Parkinson's Disease). Reports in the scientific literature indicate that heavy chain ferritin (ferritin-H) is decreased by 50% in aged rat brains and in other neurodegenerative diseases such as Alzheimer's and show that ferritin-H is found in the neurodegenerative diseases where iron-mediated oxidative damage has been demonstrated, as in Parkinson's disease and Huntington's disease. There are also studies that indicate a protective role of ferritin against cancers, such as liver and skin cancers. It has been reported that UV light induces ferritin production in skin cells and that ferritin is protective against UV damage. Indeed, ferritin-H can be used to treat any disease in which cellular injury is caused by iron-mediated oxidative damage.

Delivering the ferritin-H peptide or a functional derivative thereof to erythroid precursor cells is a more effective, more natural form of therapy than the partial measures currently in use to treat sickle cell disease and β-thalassemias. Similar delivery of the ferritin-H peptide or a functional derivative thereof provides effective treatments and protection in Alzheimer's and other neurodegenerative diseases and cancers. The ferritin-H peptide can also be delivered as a fusion protein, with parts or all of the ferritin-H peptide fused to another protein such as transferrin or other ligand for which specific receptors exist on the surface of erythroid precursor cells, neurons, or other cell types for which protection is desired. The making of fusion proteins targeted to specific tissues is well known to those skilled in the art. Alternatively, an expression clone that encodes ferritin-H or a functional derivative thereof, delivered to at least one of erythroid precursor cells, hematopoietic stem cells, neurons and other tissue cells in an appropriate vector, either ex vivo or in vivo; and the protein expressed from such a vector also cures and protects against disease.

The ferritin-H described herein is distinct from other known trans-acting proteins in its physical properties and its proposed function as a repressor that binds primarily to CAGTGC [SEQ ID NO: 6] sequences in the β-globin and γ-globin promoters. The ferritin-H subfamily is represented by a larger number of genes than the ferritin-L subfamily and includes a cluster of genes/pseudogenes on the X chromosome. One of these, ferritin-X, appears to encode a peptide identical in size and very similar in predicted three-dimensional structure to ferritin-H.

The possibility remains that the actual DNA-binding of the globin promoter CAGTGC [SEQ ID NO: 6] motif is mediated in vivo by a ferritin-associated protein that is protected from proteinase K and heat treatments and reacts with anti-ferritin antisera because of its strong association with ferritin. However, if this is the case, it is a protein that is ubiquitous in human nuclear extract, and there is no need to upregulate it, thus it is ineffective in the absence of ferritin-H, and upregulation of ferritin-H is sufficient.

The transient expression assays demonstrated that ferritin-H represses the human β-globin gene and that this repression is mediated by binding of ferritin-H and/or a co-repressor to the –150 region of the promoter containing a highly conserved CAGTGC [SEQ ID NO: 6] motif (FIGS. 1 and 6). The binding site of ferritin-H is within an important sequence required for activation of transcription of the β-globin gene. Thus, the binding of this protein and displacement of other factors is important in the repression of the human β-globin gene, as the mouse BB1 protein (which recognizes the same sequence) is involved in the repression of the mouse β-major globin gene in uninduced MEL cells. Subsequent interaction of this binding site with upstream negative regulatory regions creates a tightly-bound complex that prevents binding of other positive factors such as GATA-1 as well as sterically hinder the formation of an active transcription complex on the proximal promoter, by DNA looping.

One method of increasing ferritin-H expression is to repress expression of ferritin-L or other ferritin family proteins. This can be accomplished by using antisense DNA oligonucleotides specific for the genes that encode ferritin family proteins other than ferritin-H. Reduction and expression of these ferritin proteins leads to a higher concentration and heightened expression of ferritin-H. By shifting the ratios between ferritin-H and other ferritin family proteins, β-globin is repressed and the deleterious effects of sickle cell anemia are reduced to acceptable levels.

Heightened expression of ferritin-H also cures intracellular iron mismanagement, resulting in lower levels of harmful ferrous ions. While ferritin-H ferroxidase activity plays a role in proper management of intracellular iron, higher concentrations of ferritin-H affect expression of a number of genes involved in iron metabolism. This genetic regulatory function of ferritin-H facilitates proper iron management in cells that have been adversely affected by a wide variety of diseases. As described in the background, cancer, neurodegenerative diseases, neuromuscular disorders and atherosclerosis all lead to improper iron management within the body's cells. Increasing the concentration of ferritin-H and the resulting genetic regulatory effects alleviate the deleterious effects of improper iron management.

Studies have shown that ferritin-H exhibits the most efficient ferroxidase activity when it is expressed at roughly the same levels as ferritin-L. Equal expression levels results in the highest number of ferritin-H/ferritin-L heteropolymers. The heteropolymeric form of the 24-mer ferritin complex is the most efficient at converting the ferrous ion to the ferric ion and at sequestering iron ions. Thus, maintaining equal concentrations of ferritin-H and ferritin-L will result in proper iron management. Increasing levels of ferritin-H results in the formation of ferritin-H homopolymers. Ferritin-H homopolymers exhibit low ferroxidase activity, resulting in higher levels of the more harmful ferrous ion and adverse effects on the cells. However, the gene regulatory function of ferritin-H causes just the opposite to occur.

It is well known to those skilled in the art that there are a number of ways in which to elevate levels of ferritin-H within a cell. Introduction of the ferritin-H protein itself by any number of pharmaceutically acceptable means is well known to those skilled in the art. This includes, but is not limited to, using liposomal constructs containing ferritin-H protein. These liposomal constructs may or may not have ligands or antibodies associated therewith.

An alternative method for increasing intracellular levels of ferritin-H is to regulate expression of ferritin family molecules. This can be done in a number of ways well known to those skilled in the art. For example, but not by way of limitation, antisense DNA oligonucleotides that target ferritin family genes other than ferritin-H results in decreased expression of the targeted gene and causes greater concentrations of ferritin-H within the cell. Introduction of proteins or other compounds can also increase transcription or translation of an endogenous ferritin-H gene or a related ferritin family gene. These activating compounds can be introduced to cells in methods similar to the introduction of the ferritin-H protein itself as discussed above.

Yet another method of increasing intracellular levels of ferritin-H is to introduce a ferritin-H expressing vector into the cells. It is well known to those skilled in the art that there are a number of methods to transfect cells with a number of different vectors, including plasmids, phagemids, and cosmids. The type of vector used, the promoter region within the vector, and any control sequences used with the vector vary depending on a variety of factors known to those skilled in the art. These factors include but are not limited to the cell tissue targeted, the level of desired expression and the level of ferritin family protein expression within the targeted cells.

Yet another method of increasing intracellular levels of ferritin-H is to increase levels of an inducer that can elevate expression of endogenous ferritin-H gene. The inducer can be a protein or other chemical compound. For example, but not by way of limitation, inducers may function by binding to activator proteins to allow the activator proteins to promote RNA transcription, or inducers may function by binding to repressor proteins to disable repressor proteins from preventing RNA transcription. Alternatively, inducers can also promote protein translation.

Non-limiting examples of methods of increasing intracellular ferritin-H include intracellular induction methods, where the cell creates its own ferritin-H, and extracellular introduction methods, where ferritin-H is added to the cell (for example, when liposomal constructs are used).

Transfection of cells with vectors coding for a ferritin family protein may be performed either ex vivo or in vivo. When performed in vivo, the vectors are introduced into the patient's body. When performed ex vivo, cells are transfected with a vector and then implanted into the patient's body tissue. Stem cells are especially well suited for this; however, other cells may also be used.

Delivery Systems and Cell-Targeting Mechanisms

For delivery of proteins or peptides into living cells ex vivo there are several approaches. Small peptides (about 20 kDa or smaller) are taken up by cells without a specialized delivery system. Larger proteins are delivered encapsulated into liposomes, liposomal constructs, or within a membrane such as a red cell ghost, and the vesicles are then made to fuse with the recipient cells by chemical means (e.g., polyethylene glycol [PEG] or calcium ions). Larger protein complexes can also be delivered encapsulated, by fusing the membranes of the capsule to the plasma membranes of the target cell. For in vivo delivery of proteins or peptides targeted to a specific cell type, the method of choice is often a liposomal-type of delivery with an antibody or ligand directed at a specific cell surface protein or receptor incorporated into the liposome and the peptide or protein encapsulated within the liposome. Alternatively, fusion proteins comprised of the desired peptide fused with a protein ligand specific for the target cell receptor have been injected directly. An example of a protein ligand that can be used to target hematopoietic stem cells is Stem Cell Factor (c-kit ligand) which binds to a receptor (c-kit) enriched on the surface of hematopoietic stem cells in the bone marrow. It is well known to those skilled in the art that there are a wide variety of pharmaceutical delivery mechanisms suitable for introducing proteins, protein fragments and genetic material into a cell.

For delivery of expression clones of genes encoding ferritin-H subfamily peptides or functional derivatives of ferritin-H subfamily peptides in vivo as well as ex vivo,—that is, gene therapy—, a number of vectors are available to transfect cells to generate either stable transformants or transiently transfected cells.

For ex vivo transfection of cells for reinfusion into the host animal or patient, the vector can be a plasmid vector or a viral vector. Good expression plasmid vectors are commercially available as are transfection reagents for the plasmid vectors, many of the latter being cationic liposomes of one type or another. The viral vectors available include retroviral vectors (good for dividing cells), adenoviral vectors (transfect many cell types, with very little cell specificity), adeno-associated viral vectors, lentiviral vectors, and electroporation systems. Any of these can be used in an ex vivo protocol where the target cells are obtained as a pure or highly enriched population, to be reinfused after gene transfer. According to the present invention, the reinfusion of treated cells back into the host animal or patient can be accomplished by any one of the conventional known transfusion processes, for example, but not by way of limitation, intravenous infusion.

For in vivo gene transfer, the choices are currently limited because of the difficulty of efficiently targeting specific cells with sufficient gene copies. A targeted liposome as described in the preceding paragraph is the present method of choice if a ligand for a high-affinity, plentiful but cell-specific receptor is incorporated.

Induction of Ferritin-H Gene Expression in Human Cells

Ferritin-H is among a group of genes that have been identified as being expressed during embryogeneis. The first major site of ferritin-H expression is in the embryonic red blood cell which is formed in the mammalian yolk sac before the blood circulation is established. This cell-specific expression of ferritin-H in early development corresponds to red cell's role as the iron storage site of the embryo. Adult red cells cease expression of ferritin before hemoglobin expression begins. "Knocking out" the ferritin-H gene in mice results in intrauterine death between days 3.5 and 9.5 of development. Thus, ferritin-H is a developmentally regulated gene, expression of which is restricted to certain cell and tissue types.

Expression of ferritin-H in differentiating adult erythroid cells reverses developmental hemoglobin switching, by repressing the adult β-globin gene, and by activating the fetal γ-globin gene. Activation of endogenous ferritin-H gene expression in adult erythroid cells also reverses a developmental switch in this one cell lineage. Accomplishing this switch, in turn, reverses another developmental switch, the hemoglobin switch, which has therapeutic benefits to people with sickle cell disease and other hemoglobinopathies. Activation of ferritin-H expression in other cell types has been found to alleviate and protect against certain cancers and neurodegenerative diseases.

Reinfusion of Blood Cells

To administer the ferritin-H treated (ferritin-H protein, ferritin-H vector, or ferritin-H inducer) erythroid precursor cells, standard blood transfusion procedure can be used. This blood transfusion procedure is routinely carried out in sickle-cell patients and hemophilia patients. Erythroid precursor cells are administered intravenously after the insertion of a cannula of suitable caliber.

Examples are provided hereinbelow. However, the present invention is to be understood to not be limited in its application to the specific experimentation, results and laboratory procedures disclosed hereinbelow. Rather, the examples are simply provided as one of various embodiments and are meant to be exemplary, not exhaustive.

The ability of ferritin family proteins to bind to the 5' promoter region of the β-globin gene was ascertained only after lengthy and rigorous experimentation as described below. The first example shows that ferritin-H binds to the CAGTGC [SEQ ID NO: 6] ferritin binding site, found at bases −148 to −153 of the 5' promoter region of the human β-globin gene. Example 2 shows that in addition to binding to the ferritin binding site, ferritin-H binds to another nuclear protein that binds to the β-globin 5' promoter region further upstream of the ferritin binding site. FIGS. 8 through 12 show the experiments directed toward elucidating the mechanism by which ferritin-H represses the human β-globin gene. These results show that human K562 cell nuclear ferritin interacts with other DNA-binding proteins to repress this promoter, especially upstream silencer-binding proteins, via DNA-looping. Example 3 confirms that ferritin-H is a nuclear protein since it localizes to the nucleus of primate cells. Example 4 shows that ferritin-H represses adult β-globin and activates fetal γ-globin expression. In Example 5, a human ferritin-H transgenic mouse model is used to demonstrate that human ferritin-H represses β-major globin but not β-minor globin in mouse. Example 6 shows that ferritin-H protein, ferritin-H vector, and abscissic acid all produce a switch from HbS-to-HbF production in human sickle cell erythroid precursor cells. Example 7 shows that retinoic acid treatment can induce neuronal differentiation in human carcinomal stem cells.

EXAMPLE 1

Materials and Methods

Cell lines. K562 (human erythroleukemia) cells were grown in suspension in RPMI 1640 medium with 10% or 15% fetal bovine serum (FBS) and antibiotics as described (Berg et al., (1989) *Nucleic Acids Res* 17, 8833-52) and harvested at a density of 10.sup.6 cells/ml for making nuclear extracts. CV-1 (African green monkey kidney epithelial) cells (adherent cells used for transfections/transient gene expression assays) were grown in DMEM with L-glutamine, 10% FBS and antibiotics (Miller & Bieker (1993) *Mol Cell Biol* 13, 2776-86).

Clones, transfections, and gene expression assays. The upstream region (−610/+20) of the human β-globin gene, previously cloned in pSV2CAT (Berg et al., (1989) *Nucleic Acids Res* 17, 8833-52), was subcloned through pGEM and pSELECT (now called pALTER) and recloned into pCAT-basic (all vectors from Promega). Mutants of the −153/−148 site of the β-globin promoter were generated by transcription from mutant oligonucleotides corresponding to the −164/−128 region using the pSELECT system. Transfections of CV-1 cells were carried out with DMRIE-C transfection reagent (GibCo/BRL) in OptiMEM serum-free medium and were optimized using the green fluorescent protein plasmid pEGFP-C1 (Clontech), fluorescence microscopy and quantitative fluorescence of cell lysates with a microtiter plate reader. The reporter gene chloramphenicol acetyl transferase (CAT) was quantified in lysates of transfected cells using an ELISA (Promega) standardized with purified CAT. The EKLF (erythroid Kruppel-like factor) expression plasmid has the EKLF gene cloned into pSG-5 (Stratagene; (Miller, I. J. & Bieker, J. J. (1993) *Mol Cell Biol* 13, 2776-86) and the ferritin-H expression clone is in the eucaryotic expression vector pcEXV-1 (Wu, Y. J. & Noguchi, C. T. (1991) *J Biol Chem* 266, 17566-72). Total cellular protein was determined with the BCA microtiter plate assay (Pierce) using bovine serum albumin as a standard.

Proteins and antibodies. Ferritins from human liver (enriched in L chains) and from human heart (enriched in H chains), human transferrin (iron saturated) and apotransferrin, polyclonal (rabbit) antiserum to human spleen ferritin and nonimmune rabbit serum were obtained from Sigma Chemical Company.

Restriction fragments and oligonucleotides. The 5' region of the human β-globin gene (from −610 to +20), previously cloned in pSV2CAT, was cut into three fragments by sequential digestions with Hind III and Rsa I. The three fragments, electroeluted from agarose (Maniatis, T., Fritsch, E. F. & Sambrook, J. (1989) *Molecular Cloning: A Laboratory Manual* (Cold Spring Harbor Laboratory, Cold Spring Harbor, N.Y.), were 416 bp (−638/−223), 147 bp (−127/+20, containing the proximal promoter region), and 95 bp (the Rsa fragment, −222/−128, containing mainly distal promoter sequences). The three fragments were phenol/chloroform treated, dephosphorylated, and end-labelled with 32-P as described (Maniatis, T., Fritsch, E. F. & Sambrook, J. (1989) *Molecular Cloning: A Laboratory Manual* (Cold Spring Harbor Laboratory, Cold Spring Harbor, N.Y.); Kurien, B. T., Scofield, R. H., & Broyles, R. H. (1997) *Anal Biochem* 245, 123-126). Synthetic oligonucleotides corresponding to −232/−188 and −164/−128 were purified and annealed as previously described (Berg et al., (1989) *Nucleic Acids Res* 17, 8833-52), and the double-stranded oligos were end-labeled as above and/or used as unlabeled competitors in gel mobility shift assays.

Preparation of nuclear extracts. Each nuclear extract preparation was made from two liters of K562 cells ($1 \times 10^6$ cells/ml) using the procedure of Dignam, Lebovitz, and Roeder (Dignam, J. D., Lebovitz, R. M. & Roeder, R. G. (1983) *Nucleic Acids Res* 11, 1475-89). Protein content of the extracts ranged from 3 to 6 mg/ml. Extracts enriched 80-90% in ferritin-like protein(s) were prepared by treating the crude extracts with proteinase K and/or heat at 75° C. (Atkinson, B. G., Dean, R. L., Tomlinson, J. & Blaker, T. W. (1989) *Biochem Cell Biol* 67, 52-7).

Gel mobility shift assays. Gel retardation assays (i.e., gel shifts) were used to determine DNA binding of the extract proteins to the Rsa I (95 bp) fragment and synthetic oligonucleotides (Berg et al., (1989) *Nucleic Acids Res* 17, 8833-52; Fried & Crothers (1981) *Nucleic Acids Res* 9, 6505-25). Each reaction contained 0.5-2 ng of DNA, 1.0-5.0 ug of extract protein, 1.0-5.0 ug of poly dI:poly dC, 100 mM KCl, and binding buffer (Berg et al., (1989) *Nucleic Acids Res* 17, 8833-52). Unlabeled competitor oligonucleotides ranged from 15- to 2000-fold molar excess and were included in the reaction mixture with the probe before adding protein. Gels used for retardation assays were 4%, 5%, or 6% acrylamide and the running buffer was low ionic strength TAE (Berg et al., (1989) *Nucleic Acids Res* 17, 8833-52).

Sequence alignments and homology searches. All mammalian β-globin promoter sequences (−200/+1) were obtained directly from GenBank and manipulated using the PILEUP program followed by the LINEUP program of the University of Wisconsin GCG Package.

Results

Ferritin-H repressed expression driven by the β-globin promoter in transient co-transfection assays. A transient expression assay was set up with CV-1 cells in which β-globin promoter-driven expression of a reporter gene is low unless the cells are co-transfected with an expression clone of EKLF, a developmentally-specific activator of transcription. Results with a β-CAT reporter plasmid are shown in FIG. 1. The expression level of β-CAT stimulated by EKLF was repressed by over 60 percent by co-transfection of an expression clone of human H-chain ferritin (i.e. ferritin-H).

Controls were a positive CAT-control plasmid (expresses CAT constituitively), a negative CAT-basic plasmid (contains no promoter), and β-CAT without EKLF stimulation. The experiment shown in FIG. 1 has been repeated five more times with β-CAT and three times with a β-Luc (β-promoter-luciferase) construct with very similar results. The repression was also evident (although reporter activity is lower) when EKLF is omitted (data not shown). Other controls included co-transfection of the "empty" carrier plasmids for all the expression clones (no effect on reporter gene expression) as well as keeping the total amount micrograms of transfected DNA constant (e.g., FIG. 6), to rule out the possibility of non-specific inhibition of gene expression due to excess DNA or to some aspect of the structure of a carrier plasmid. Co-transfection of an expression clone for ferritin-L sometimes resulted in some repression of reporter gene expression; but the effect was less dramatic and inconsistently observed.

Figure 2A:
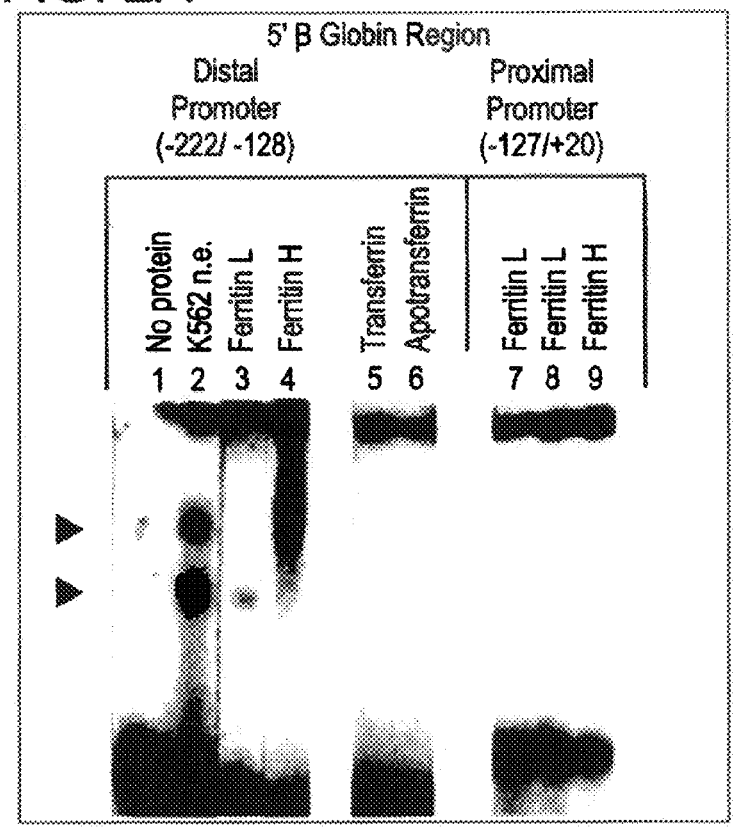
FIG. 2A shows the binding of ferritin chains to the distal promoter of the human β-globin gene. Restriction fragments of the 5' β-globin distal promoter (−222/−128), in the left side set of lanes 1 through 6, or proximal promoter (−127/+20), in the right side set of lanes 1 through 5, were end-labeled with $^{32}P$ and used as probes in gel mobility shift assays with K562 nuclear extract (left lane 2), purified human liver ferritin ($F_L$, lanes 3 [left] and 7 and 8 [right]), human heart ferritin ($F_H$, lanes 4 [left] and 9 [right]), human transferrin (T, lane 5[left]) and apotransferrin (aT, lane 6[left]), as described under Materials and Methods. Lane 1 [left] contained only DNA (no protein).
Figure 3A:
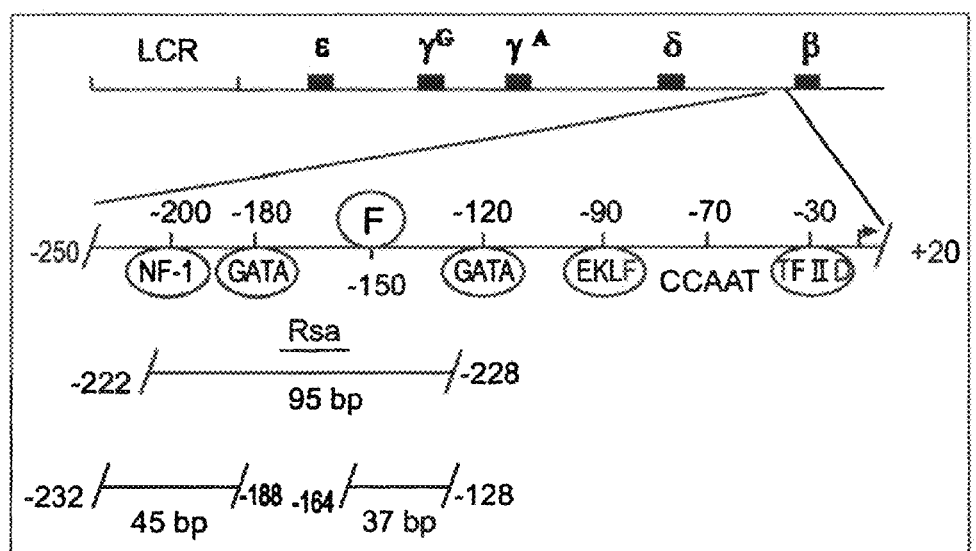
FIGS. 3A-3B illustrate the localization of the binding region of nuclear ferritin (F) to the −164/−128 region of the β-globin promoter, using the antibody super-shift assay.

Binding of ferritin to β-globin promoter DNA. A restriction fragment containing part of the distal promoter of the human β-globin gene, from −222/−128, was bound by human liver- or human heart-derived ferritin, as shown in gel retardation assays (FIG. 2a, left side, lanes 3 and 4). Ferritin from human heart (which is enriched in H-type (heavy) subunits) showed a higher degree of binding than liver ferritin (which is relatively enriched in L-type subunits), as indicated by the darker band in lane 3 (left). A restriction fragment containing the proximal promoter (−127/+20) did not show this binding (FIG. 2a, right side, lanes 2-5); and another iron-binding protein, transferrin (known to be primarily extracellular except when bound to its receptor) did not bind the distal fragment bound by ferritin (FIG. 2a, left side, lanes 5 and 6). The shift bands produced by the binding of human liver ferritin and by human heart ferritin corresponded to the lower and upper shift bands produced by K562 cell crude nuclear extracts, respectively (FIG. 2a, left side, lanes 2-4). Nuclear extract ferritin produced either shift band and that the higher molecular weight band yielded the lower band when eluted and reshifted. Since at least one of the multiple bands contained GATA-1, the multiple shift bands with crude extracts (e.g., FIG. 3) were the result of different sized aggregates of ferritin subunits or oligomers of the DNA-protein complex and/or complexes with other proteins in crude extracts.

Figure 2B:
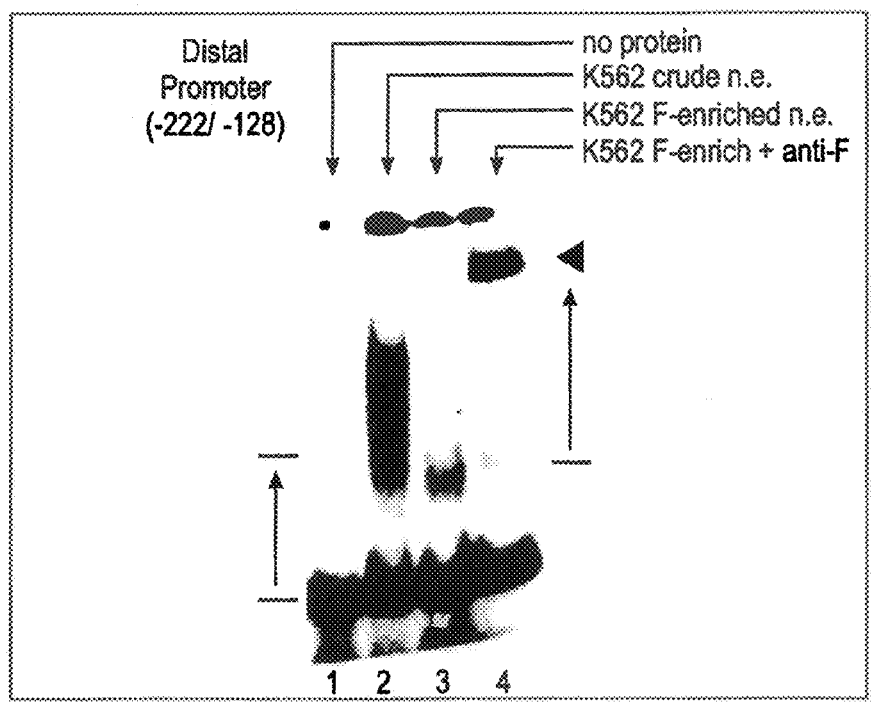
FIG. 2B shows the binding of a ferritin-like protein from K562 cell nuclear extracts to −222/−128 β-globin region. A procedure for obtaining ferritin 90% pure from embryonic red cells using proteinase K digestion followed by heat treatment at 75° C. (36) was applied to K562 cell nuclear extract; the clear supernatant fluid obtained after centrifugation gave a single shift band (third lane from left) which gave a "supershift" with anti-ferritin polyclonal antiserum (last lane), indicating that there is a protein in the nuclear extract with three properties of ferritin (proteinase K-resistance, heat stability, and reactivity with an antiferritin-specific antiserum).
Figure 2C:
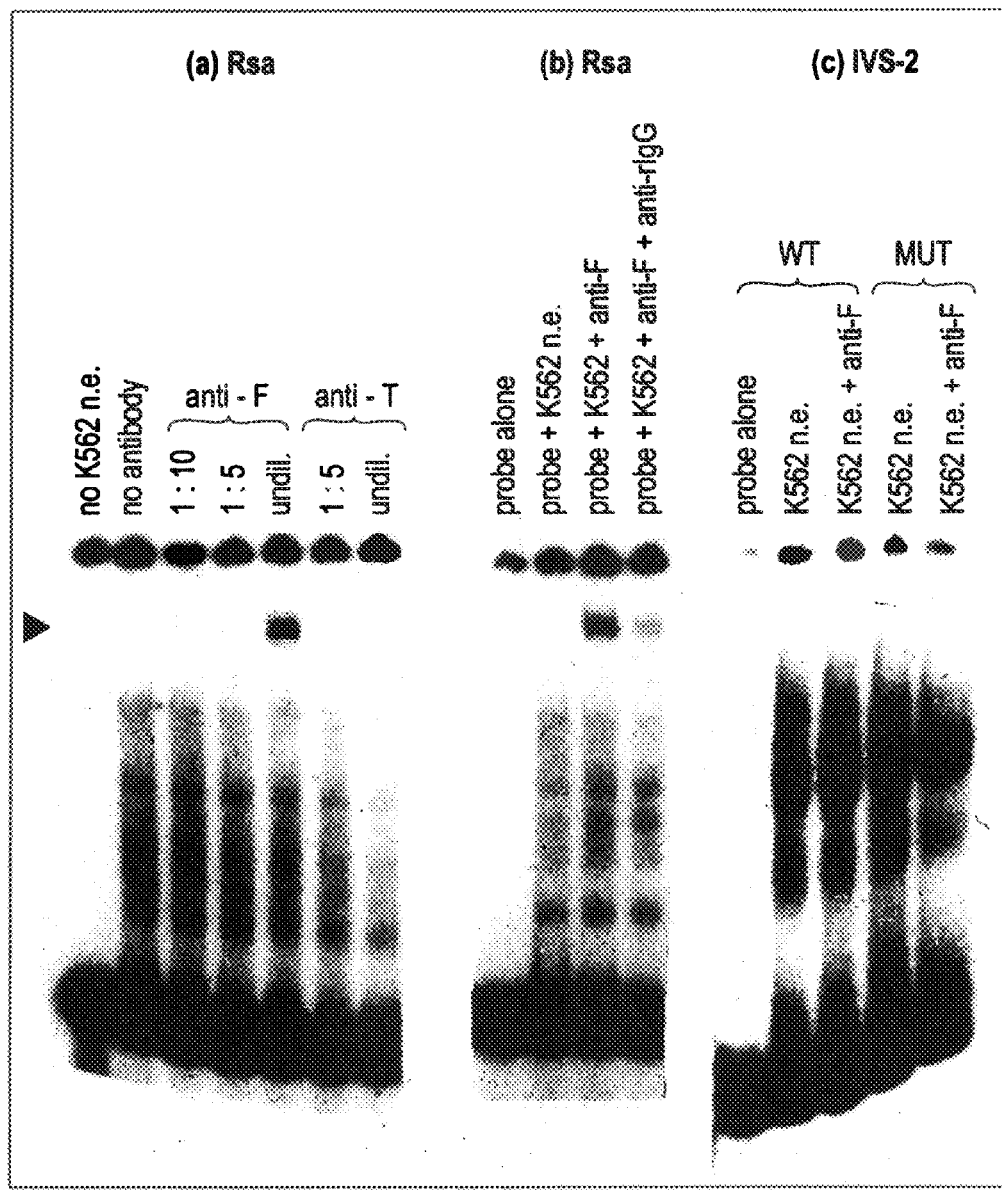
FIG. 2C shows control experiments demonstrating the specificity of the anti-ferritin supershift assay. Left set of lanes (a): anti-F (anti-ferritin) gives the supershift (arrow); anti-T (anti-transferrin) does not. Center set of lanes (b): anti-F supershift is inhibited by anti-rabbit-IgG. Right set of lanes (c): Using normal or mutant sequences from the 2nd intron (IVS-2) of the human β-globin gene as probes, primary shift bands with K562 nuclear extract were obtained; however, none were recognized by the anti-F (i.e., no supershift bands were obtained).

Enrichment of a ferritin-like protein from K562 cell nuclear extracts. A polyclonal antiserum to human spleen ferritin (which is composed of a mixture of heavy and light chains of ferritin) caused a supershift of part of the DNA-protein complexes formed from crude K562 nuclear extract and the −222/−128 restriction fragment, and the intensity of the super-shift band was proportional to the amount of antiserum added (FIG. 2b). The supershift with anti-ferritin antiserum was specific for this DNA-protein complex: very little-to-no DNA was shifted in the absence of nuclear extract, neither anti-transferrin antiserum nor nonimmune rabbit serum (not shown) shifted the complex, anti-rabbit IgG inhibited the supershift, and protein complexes with other DNAs such as β-IVS2 were not shifted by the anti-ferritin antiserum (FIG. 2C).

Ferritin, unlike most proteins, is resistant to proteinase K digestion and heat at 75° C., and can be obtained ninety percent pure from extracts of embryonic/larval erythroid cells using these two treatments. When this procedure was applied to K562 nuclear extracts, the remaining protein gave a single shift band with the −222/−128 restriction fragment (FIG. 2b, third lane from the left). Furthermore, when the anti-ferritin antiserum was added to the reaction mixture after incubation of the DNA and binding protein, a larger complex was formed, resulting in a supershift band (FIG. 2b, fourth lane). It should be noted that the primary shift band with nuclear extract treated with proteinase K did not shift as far as the gel bands obtained with untreated extract. When investigated in a series of timed digests, it was found that ferritin was subject to partial digestion by proteinase K; what remained after a 10-15 min digestion (e.g., FIG. 2c, third lane) was a proteinase K-resistant core that still binds DNA. Furthermore, increasing the amount of the enriched peptide preparation gave an increasing intensity to the shift band, and the band gradually moved up the gel as the complex builds in amount.

Figure 3B:
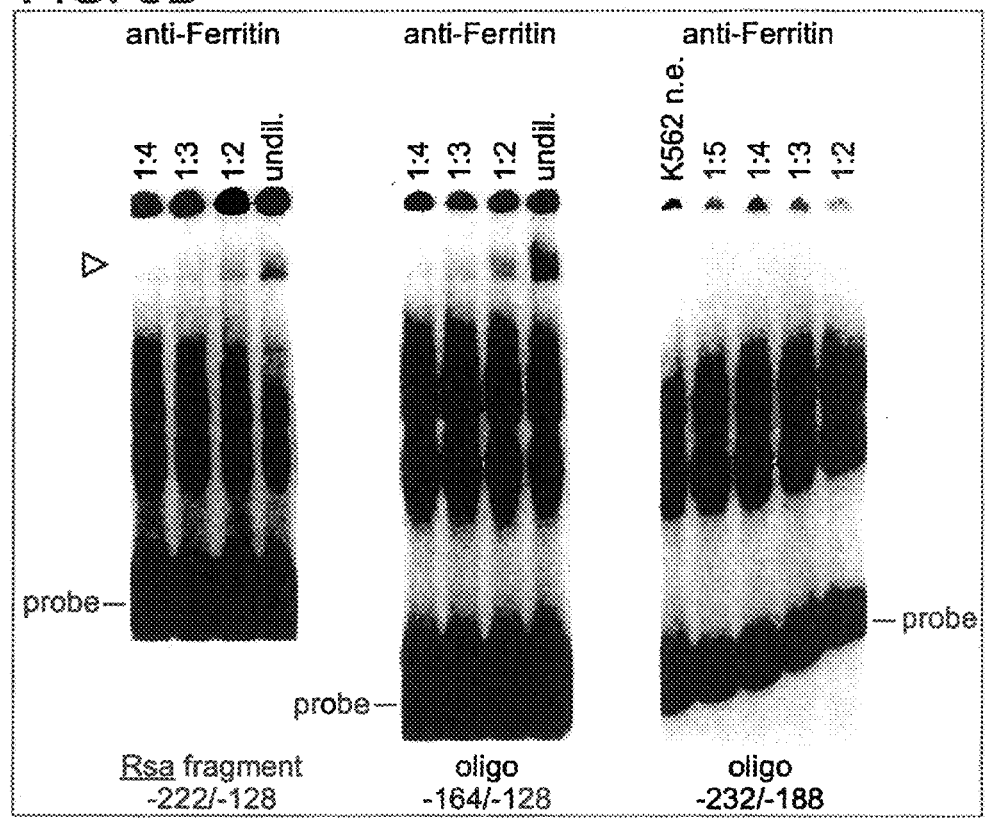

As shown in FIG. 3B, the left series of lanes, a single supershift band was obtained (arrow) with the 95-bp distal promoter that increased in intensity with increasing antiserum. To further localize the binding of the anti-ferritin reactive protein, the supershift was also performed with 32 P-labeled double-stranded oligonucleotides of the −232/−188 and −164/−128 sequences. The more 39 oligonucleotide gave a supershift band, whereas the more 59 oligonucleotide did not (FIG. 3B), indicating that the protein recognized by the antiserum bound to a 37-bp sequence between 31 164 and −128. The lack of a supershift with the −232/−188 oligonucleotide also served as a control for the specificity of the antibody.

Localization of the binding region with the antibody supershift assay. The antibody gel shift was also used with 32P-labeled double stranded oligonucleotides corresponding to the 3' and 5' ends of the 95 bp restriction fragment (FIG. 3A) and with crude K562 nuclear extracts to further localize the binding of ferritin. Thus only the 3' oligo gave the supershift band (FIG. 3B), indicating that the protein recognized by the antiserum bound to a 37 base pair (bp) sequence between −164 and −128.

Figures 4A, 4B:
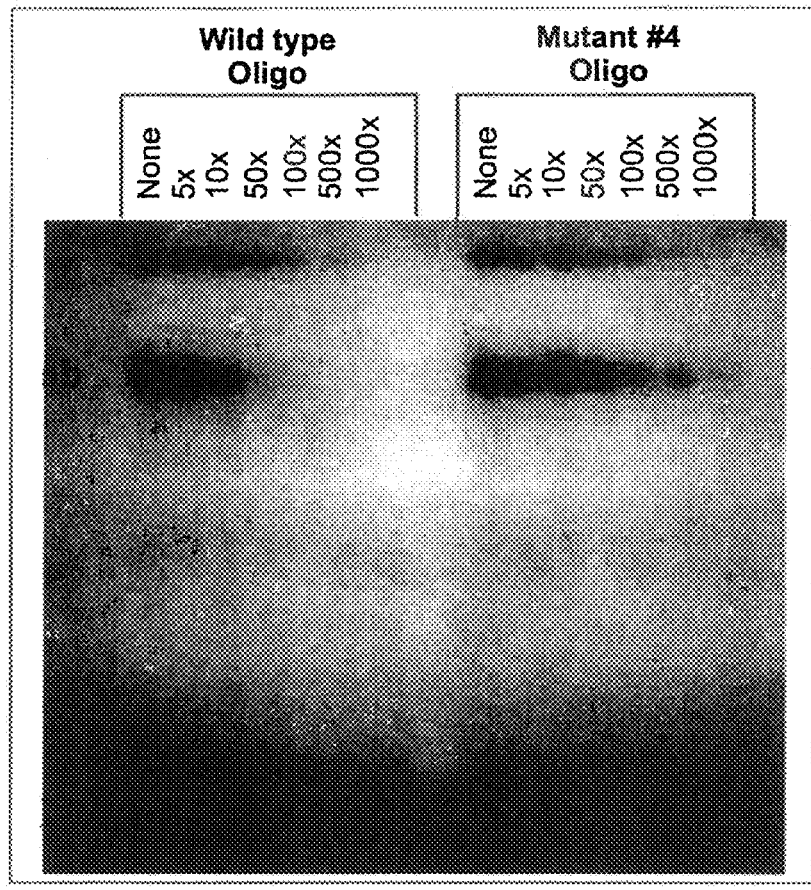
FIGS. 4A-4D illustrate the definition of the binding site of nuclear ferritin, using oligonucleotide competition assays.
Figures 4C, 4D:
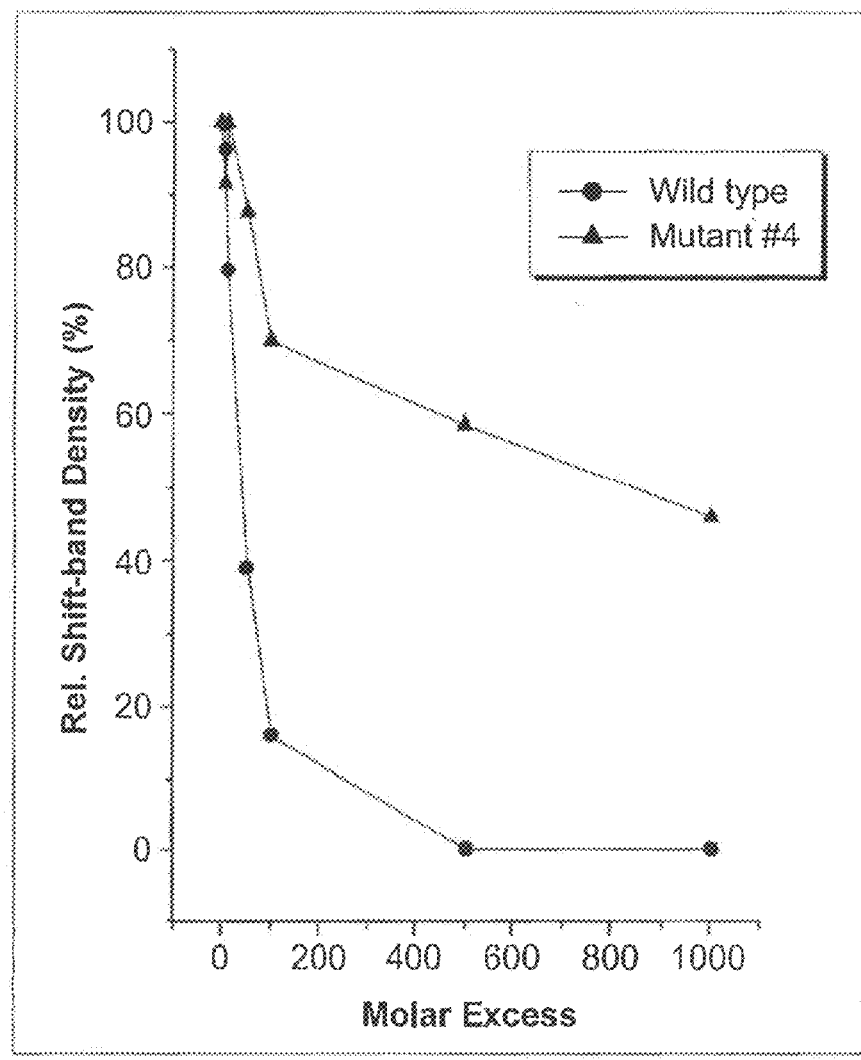

Definition of the binding site with competition gel shifts. To further localize the binding of ferritin, the 37 bp oligonucleotide was mutated in different places, replacing six nucleotides at a time with all A's, all C's, or all G's, with complementary nucleotide replacements in the opposing strand (FIG. 4A). A competition gel shift assay was done with the partially purified protein from heated K562 nuclear extract, in which each of the unlabeled mutant oligos as well as the native sequence was competed against the 32-P-labeled native sequence for binding. All mutants competed for binding as well as the native sequence except those mutated in the −153/−148 region, i.e., mutated in the sequence CAGTGC [SEQ ID NO: 6] (e.g., FIG. 4D). This demonstrated that these six base pairs in the −153/−148 region comprise the binding site of ferritin-H. In FIG. 4C, the specificity of this binding was titrated and quantified in oligo competitions with the unlabeled native sequence compared with the sequence mutated in all of the six nucleotides found to be important for binding, i.e., the sequence CAGTGC [SEQ ID NO: 6] (native) compared with mutant #4 (FIG. 4A). Whereas the binding to the labeled native sequence was significantly competed with 50-fold excess of unlabeled self, it took 1,000-fold excess of the unlabeled mutant oligo to begin to compete with the binding to the native sequence, a twenty-fold difference.

Sequence alignments of the promoters (−162/+1) from twelve mammalian adult β-globin genes showed that the −150 CAGTGC [SEQ ID NO: 6] of the human β-promoter is very highly conserved. In a phylogenetic comparison of twelve mammalian adult β-globin promoters from the cap site to −162 (FIG. 5, in which the sequences for human, gorilla, macaca, bovine, goat, sheep, galago, tarsius, lepus, rabbit, rat and mouse, correspond to SEQ ID NOS: 7-18, respectively), the CAGTGC [SEQ ID NO: 6] sequence in the −150 region is among the most conserved of the cis-acting elements, second only to the TATA [SEQ ID NO: 20] and CCAAT [SEQ ID NO: 21] boxes in its high degree of conservation, as highly conserved as the proximal CACC [SEQ ID NO: 22] motif and more highly conserved than the distal CACC [SEQ ID NO: 23].

In a co-transfection experiment, an EKLF effector plasmid alone or an EKLF effector plasmid plus a ferritin-H expression plasmid were co-transfected with either a native (W) β-globin promoter-CAT plasmid (with a wildtype CAGTGC [SEQ ID NO: 6] ferritin binding site at −153/−148) or a mutated (M) β-globin promoter-CAT plasmid (with a mutated −153/−148 site) (FIG. 6). As a positive control, EKLF-stimulation of CAT expression was not affected by mutations in the ferritin binding site. But the ability of ferritin-H to repress expression of CAT was abolished by mutations in the ferritin binding site.

Discussion

In CV-1 cells, an expression clone of human ferritin-H down-regulated expression of an EKLF-stimulated β-globin promoter-driven CAT reporter gene (FIG. 1). A protein in K562 cell nuclear extracts had unique properties, i.e., stability to proteinase K and heat (75° C.) and reactivity with anti-ferritin antisera. Ferritin-H bound to a 5' region of the β-globin gene that is required for activation of the β-globin gene in K562 and normal erythroid cells, i.e., the region between −128 and −222 from the cap site (FIG. 3). This DNA region has been shown to bind native human ferritin in gel shift experiments (FIG. 2). The specificity of the binding of the ferritin-like protein has been confirmed using different DNA segments and oligonucleotides in an antibody gel shift assay, and the oligos and antiferritin antiserum have been used to show that the binding site is between −128 and −165 (FIG. 3). Competition gel shift assays with mutated oligonucleotides have shown that the binding of ferritin requires the nucleotides CAGTGC [SEQ ID NO: 6], at −153/−148 of the human β-globin gene; and when this CAGTGC [SEQ ID NO: 6] motif was mutated, in vitro binding was reduced approximately twenty fold (FIG. 4). The ability of ferritin-H to repress in this system was abolished, but EKLF-stimulation was retained, when the −153/−148 ferritin binding site was mutated in the co-transfected β-globin-reporter plasmid (FIG. 6). These results show that ferritin-H can repress the human adult β-globin gene by binding the promoter in a sequence-specific manner. The biology of ferritin-H and its highly conserved binding site (FIG. 5), as well as its demonstrated function in transient assays, show that in K562 cells it is indeed functioning as a β-globin repressor. Such a repressor is useful in ameliorating sickle cell and other genetic diseases.

It is noteworthy that an RNA sequence CAGUGN [SEQ ID NO: 24] has previously been found to function in the regulation of translation and stability of mRNAs coding for proteins involved in iron metabolism, e.g., mRNAs for ferritin subunits and for the transferrin receptor. In this quite different context, the hexanucleotide is at the apex of a stem-loop structure referred to as an IRE (iron-responsive element), a stable secondary structure formed in the 5' or 3' untranslated regions of the single-stranded mRNAs. The regulatory protein which binds to the IRE (the IRE-BP) has been identified as the cytosolic form of aconitase, a cubane iron-sulfur cluster protein with a molecular mass close to 97 kDa. In contrast, the heat-stable, ferritin-H recognizes the CAGTGC [SEQ ID NO: 6] sequence in DNA and apparently has a molecular mass of about 20 kDa, or less if partially proteolyzed.

Globin gene regions are enriched in CAGTGC [SEQ ID NO: 6]/CAGTGN [SEQ ID NO: 25] sequences relative to the frequency one would expect for the sequence to occur at random. The human genome, as well as the 73,326 bp sequence of the β-like globin gene cluster on chromosome 11, is approximately forty percent G+C. Therefore, the frequency of occurrence of G and C nucleotides is 0.2 each, and the frequency of A and T is 0.3 each. The random frequency of occurrence of the sequence CAGTGC [SEQ ID NO: 6] is (0.2)(0.3)(0.2)(0.3)(0.2)(0.2)=0.000144. Therefore, the sequence would be expected to occur by chance ten-to-eleven times in the 73,326 bp of the β-like cluster. The actual occurrence is thirty-six times, three-to-four times the number expected by chance. Similarly, the pentamer CAGTG [SEQ ID NO: 26] (in the sequence CAGTGN [SEQ ID NO: 25]) occurs 205 times, again about four times the fifty-two/fifty-three occurrences expected by chance. The function of this sequence, like other cis-regulatory elements, is context-dependent. The sequence occurs in the 5' and 3' regions of the ε- and γ-globin genes, but these locations and their surrounding sequences are markedly different from the −153 location for the β-globin gene. Binding of ferritin-H to sites 5' and/or 3' to the ε- and γ-globin genes has a stimulatory rather than an inhibitory effect on transcription.

Phylogenetic footprinting is useful for identifying important binding sites for regulatory proteins. In this regard, it is interesting that the CAGTGC [SEQ ID NO: 6]/CAGTGN [SEQ ID NO: 25] sequence is very highly conserved in sequence and location within mammalian β-globin gene promoters (FIG. 5, in which the sequences for human, gorilla, macaca, bovine, goat, sheep, galago, tarsius, lepus, rabbit, rat and mouse, correspond to SEQ ID NOS. 7-18, respectively), and is found in the β-promoters of chickens and frogs as well. The high conservation of this sequence means that this binding site has an important function. The *Xenopus* adult major β-globin gene has the CAGTGC [SEQ ID NO: 6] sequence at −45 from the cap site, and an oligonucleotide containing this sequence binds the human ferritin-H from K562 nuclear extracts more strongly than the corresponding region of the human β-globin promoter. Consistent with the result that ferritin-H acts as a repressor of adult B-globin in human K562 cells, the −150 binding site for ferritin-H competes with the mouse n-major −160 site known to bind the repressor protein BB1.

EXAMPLE 2

Materials and Methods

Materials: Calf intestine alkaline phosphatase, T4 polynucleotide kinase, and Sau 96 I were obtained from Promega/Fisher. $^{32}$P-γ-ATP was from Dupont/NEN. Polyclonal (rabbit) antiserum to human spleen ferritin was obtained from Sigma Chemical Company. All other reagents were molecular biology grade.

Restriction fragments and oligonucleotides: The 5' region of the human β-globin gene (from −610 to +20), previously cloned in pSVOCAT, was cut from the purified plasmid by digestions with Hind III and Bam HI. The 630 bp fragment was phenol/chloroform treated, dephosphorylated, and end-labelled with $^{32}$P. Synthetic oligonucleotides corresponding to the core/BP-1 binding site of NCR1 (−584/−527), the more distal of the two 5'-β-globin silencers, and −164/−128 region of the promoter were purified and annealed, and the double-stranded oligos were end-labeled as above and/or used as unlabeled competitors in gel mobility shift assays.

Preparation of nuclear extracts: Nonadherent K562 cells were grown in suspension in a medium composed of RPMI 1640 and 15% fetal bovine serum as described and harvested at a density of 106 cells per ml. For each preparation, nuclear extract was prepared from two liters of cells. Protein content of the extracts ranged from 3 to 6 mg/ml. Extracts enriched approximately 80% in proteins which specifically bind the −150 promoter region and the −550 silencer region were prepared by treating the crude extracts with heat at 80° C.

Gel mobility shift assays: Gel retardation assays (i.e., gel shifts) were used to determine DNA binding of the partially purified extract proteins, first to the synthetic oligonucleotides corresponding to −550 silencer and to the −150 region of the promoter, and subsequently to the 630 bp fragment of the human β-globin gene containing both the promoter and upstream regulatory sequences with the modifications described in the legend to FIG. 11. Gels used for retardation assays were 4% acrylamide and the running buffer was low ionic strength TAE.

Experimental design: The DNA looping assay is performed by mixing an extract containing proteins specific for regulatory sites that are proposed to interact, with DNA containing the contiguous sites separated by intervening DNA; and the binding of the proteins is detected with a standard EMSA. If proteins bound to separate sites interact with each other in a stable way, the intervening DNA forms a loop which can be cut at a unique restriction site in the loop. The test for looping is whether the DNA-protein complex retains its EMSA migration as a single band after the cut. Controls include lanes with deproteinized aliquots of the reaction before and after the restriction digest, to prove that the loop was indeed cut. The conditions used for cutting the looped complex with Sau 96 I are given in the legend to FIG. 11.

Results

It has been shown that a restriction fragment containing part of the distal promoter of the human β-globin gene, from −222/−128 bp, is bound by ferritin-H protein in K562 cell nuclear extracts, and is specific for the −150 region. At least two proteins are specific for the functionally defined silencers that map upstream of the proximal and distal promoter of the human β-globin gene, in the regions of −300 (−338/−233) and −530 (−610/−490) from the cap site. To explore interactions between these silencers and the β-promoter, a DNA looping assay was designed for detecting DNA looping stabilized by interactions between proteins bound to sites separated by moderate lengths of intervening DNA. A partially purified K562 cell nuclear extract that contains proteins that bind these separate regions was used in the DNA looping assay.

Figure 8:
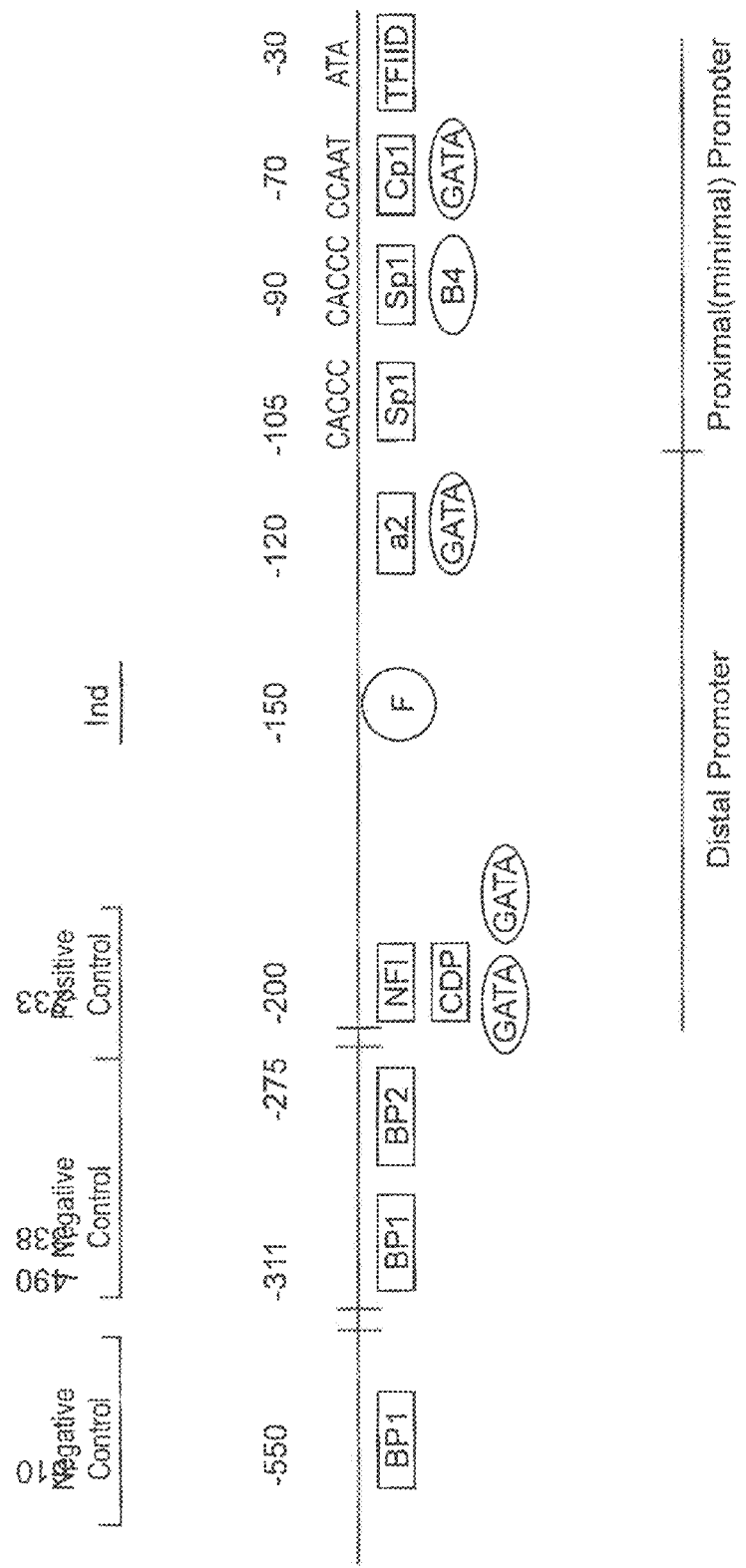
FIG. 8 shows the protein-binding sites 5′ to the human β-globin gene. General factors are shown in rectangles, erythroid-specific factors are shown in elipses, and the ferritin protein is shown as a circle.
Figure 9:
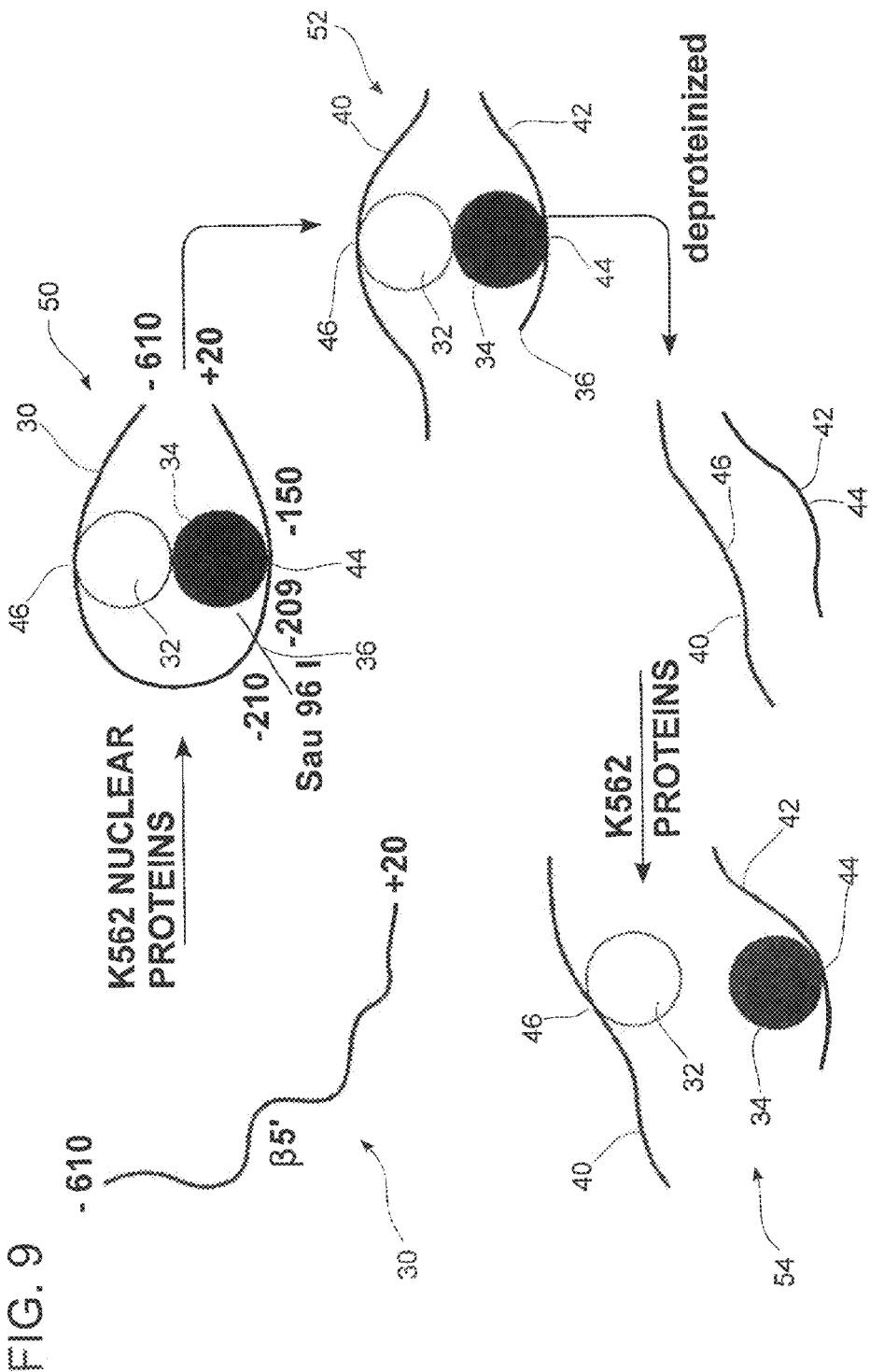
FIG. 9 shows a diagrammatic interpretation of the DNA looping experiment in example 2. 5′ promoter region 30 corresponds to lanes 1 and 4 in FIG. 10, protein/DNA complex 50 to lane 2 (before cutting with Sau 96I), protein/DNA complex 52 to lane 3 (after cutting), deproteinized fragments 40 and 42 to lanes 5 and 6, and protein/DNA mixture 54 to lane 7. In this explanation, a protein or proteins bound to the promoter, drawn as a dark circle (e.g., the protein bound at the −150 site) interacts with a protein or proteins (drawn as an open circle) bound upstream of the −210 restriction site (e.g., one or both of the two previously described silencer-binding proteins), resulting in a looping of the intervening DNA which can be cut with the restriction enzyme without disturbing the complex or its mobility as a single band in the gel shift assay.
Figure 10:
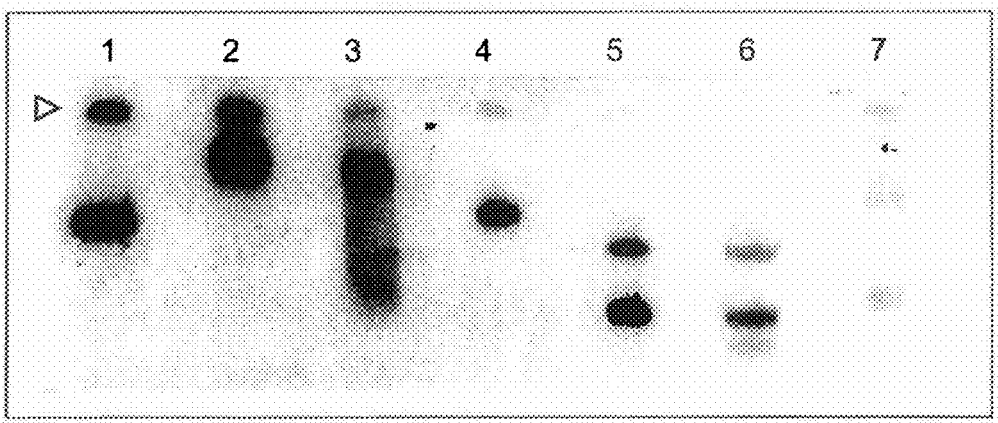
FIG. 10 illustrates DNA looping in vitro with the −610/+20 β-globin DNA and partially purified proteins from K562 nuclear extracts. Gel shift was performed to detect DNA looping before and after cutting the loop with restriction enzyme Sau 96I. The open arrowhead marks the origin. Lane 1—migration of the pure 630 bp (−610/+20) DNA. Lane 2—DNA plus heated K562 nuclear extract, i.e., shifted DNA (DNA+protein). Lane 3—DNA plus heated extract, cut with Sau 96I. Lane 4—lane 2 sample, deproteinized before electrophoresis. Lane 5—lane 3 sample, deproteinized after cutting but before electrophoresis. Lane 6—DNA alone, precut with Sau 96I. Lane 7—DNA precut with Sau 96I, then reacted with extract proteins. (Note: Half as much material was loaded onto the gel for lanes 6 and 7, although the reaction conditions and concentrations were the same as lanes 1-5.)
Figure 11:
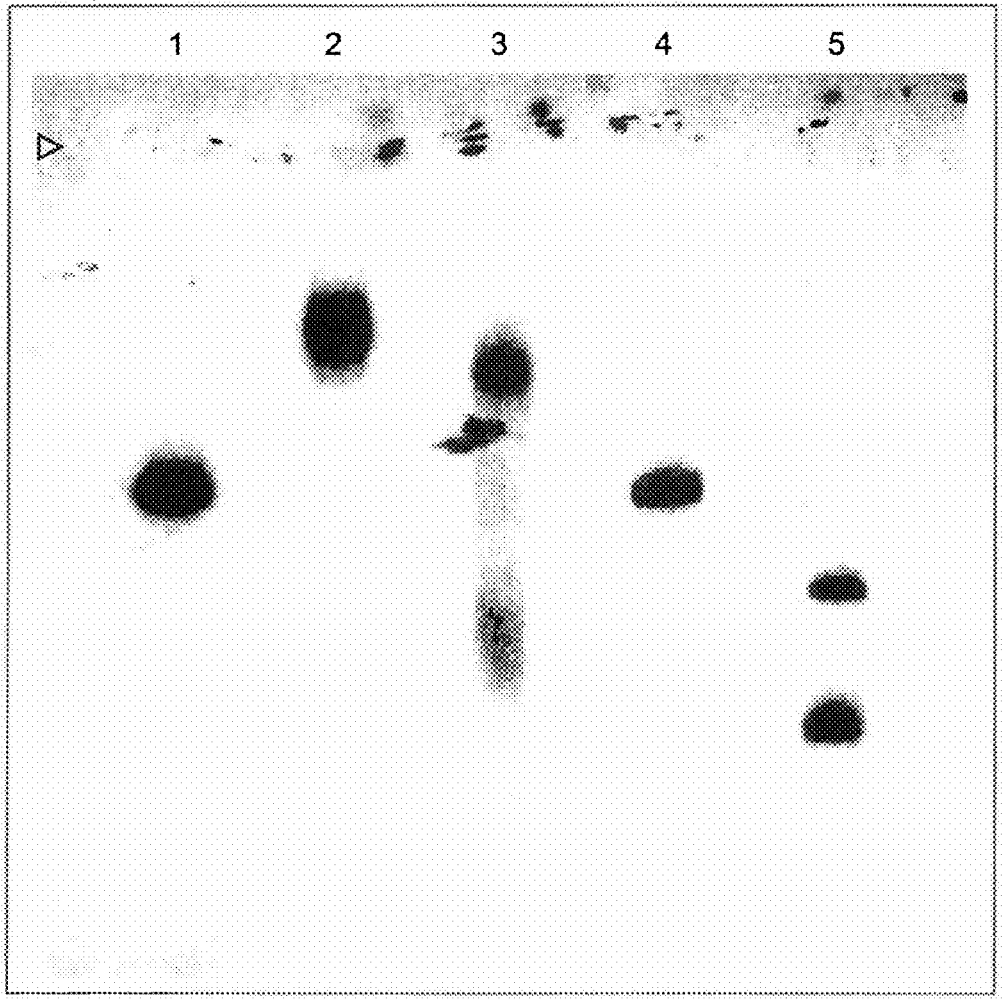
FIG. 11 illustrates the in vitro DNA looping assay based on the combined use of the electromotive mobility shift assay (EMSA) and a single-site cleavage with an appropriate restriction enzyme. Lane 1: Migration of the 630 bp of 5′ β-globin DNA alone (arrowhead marks the origin). Lanes 2 and 3: Gel shifts (EMSAs) were performed with a partially purified nuclear extract from uninduced K562 cells and the DNA, before (lane 2) and after (lane 3) cutting with Sau 96I. All the DNA was bound by protein in a single, shifted complex (lane 2) which retained its migration as a single band after the restriction cut (lane 3). Lanes 4 and 5: DNA samples recovered after deproteinization of the complexes in lanes 2 and 3, respectively. Preparation of nuclear extracts: Nuclear extracts of nonadherent K562 cells were prepared by the procedure as previously described (Dignam, J. D., Lebovitz, R. M. & Roeder, R. G. (1983) *Nucleic Acids Res* 11, 1475-89). Partially purified extracts, 80% enriched in binding proteins of interest, were prepared by heating the nuclear extracts at 80° C., centrifuging, and retaining the supernatant fluid as previously described (Atkinson, B. G., Dean, R. L., Tomlinson, J. & Blaker, T. W. (1989) *Biochem Cell Biol* 67, 52-7). The enriched extract contained proteins that bound the −150 (−164/−128) and the −530 (−584/−527) oligonucleotides in the standard EMSA. Gel mobility shift assays (EMSAs): The procedure of Fried and Crothers (Fried & Crothers (1981) *Nucleic Acids Res* 9, 6505-25; Berg et al., (1989) *Nucleic Acids Res* 17, 8833-52) was used, except that each reaction (which contained 2 ng [9,000 cpm] of 630 bp DNA, 2.5 ug of extract protein, 1.0 ug of poly dI:poly dC, 100 mM KCl, and binding buffer) was in a volume of 5 μl (instead of the usual 25 μl). The protein and DNA were allowed to interact at rm temp for 20 min. and the retardation assays were performed with four percent acrylamide gels at low ionic strength. Design of DNA looping experiments: To detect looping due to the interaction of promoter-bound protein with protein bound further upstream (ca. −300 to −600 bp), the DNA-protein complex was reacted with Sau 96I, which cleaves this DNA at −210/−209 bp as shown in FIG. 1, using the manufacturer's instructions, modified as follows: 2 μl of enzyme and 15 μl of enzyme buffer plus BSA were used in a total volume of 31 μl which included the contents (5 μl) of the protein-DNA binding reaction, at rm temp.

FIG. 8 is a diagram of the β-globin gene 5' region used as a probe in these experiments. FIGS. 11 and 10 show EMSAs using this 630 bp probe (−610/+20) combined with restriction digests to demonstrate looping, and FIG. 9 gives a diagrammatic interpretation of the results. The partially purified protein extract used for these experiments was found to contain both the −150 promoter-binding protein and silencer (−530)-binding activity by separate gel shift assays with their respective oligonucleotides (data not shown).

Figure 12:
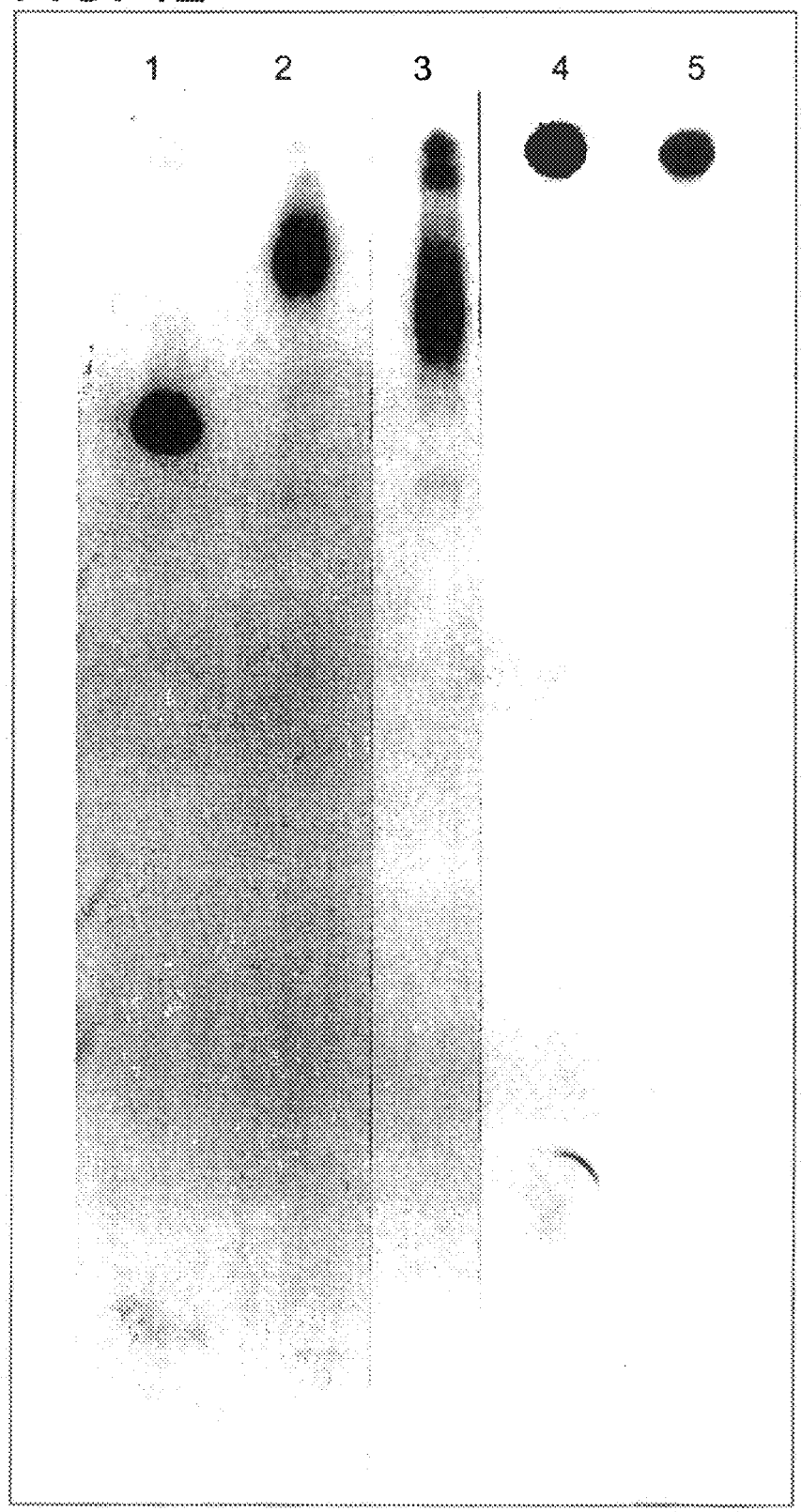
FIG. 12 shows a gel mobility shift assay demonstrating that the nuclear extract contains a DNA binding protein that binds upstream of the ferritin-H binding site and also binds to ferritin. Lane one shows the unshifted 630 bp segment of the β-globin 5′ promoter region. Lane 2 contains the 630 bp fragment with nuclear extract added. Because both the upstream binding protein and ferritin-H are present, the DNA is looped and the band has shifted. Lane 3 contains the 630 bp fragment and nuclear extract from which the ferritin-H has been removed. Because only the upstream binding protein is present, there is less of a band shift. However, the fact that there is a lesser shift shows that a protein is bound, and that the complex is not as great due to the absence of ferritin-H. Lanes 4 and 5 have the same sample as lane 2 with anti-ferritin antiserum added. Because the 630 bp fragment is bound to the ferritin which then binds to the antiserum, a supershift results.

Lane 1 in FIGS. 10-12 shows the migration of the DNA alone, which gave a single band. In lane 2 of FIGS. 10-12, DNA was retarded in its migration, due to the binding of proteins from the partially purified K562 nuclear extract.

In lane 3 of FIGS. 10 and 11, the material was reacted with the restriction enzyme Sau 96 I, after the DNA and proteins had formed a complex; the large majority of this material was retarded in its migration similar to that in lane 2. (As shown in FIG. 8, there is a single Sau 96 I site in the 5' β-globin sequence, at −210, which cuts the DNA between the promoter and the upstream regions.) In lanes 4 and 5 of FIGS. 10 and 11, the complexes in lanes 2 and 3, respectively, were deproteinized and run as the pure DNA, showing that one large piece of DNA was recovered from the complex in lane 2, whereas all the DNA from the complex in lane 3 was cut, giving two clean bands (lanes 5) identical in their migration to bands obtained when pure DNA was reacted with the restriction enzyme (lane 6, FIG. 10). The lengths of these fragments were 229 bp (+20/−209, containing the promoter) and 401 bp (containing the upstream sequences, including the silencers). When the mixture containing these fragments of pre-cut DNA was reacted with the partially purified proteins, the two fragments were shifted independently, but the large (looped) complex was not formed (lane 7, FIG. 10). The observed fact that the complex detected in lane 2 of both figures held together after the DNA has been cut completely with Sau 96 I indicates that a loop was initially formed between a site or sites downstream from −209 and a site or sites upstream from −210.

Compared to lane 2 of FIG. 12 (a shift in DNA migration was caused by ferritin-H binding to the ferritin-H binding site, and one or more upstream biding protein(s) binding to the site(s) upstream of the ferritin-H binding site and at the same time binding to ferritin-H), lane 3 of FIG. 12 showed a lesser shift (one or more upstream biding protein(s) bind to the site(s) upstream of the ferritin-H binding site; no ferritin-H binds to the DNA since ferritin-H is removed the nuclear extract). Compared to lane 2 of FIG. 12, lanes 4 and 5 of FIG. 12 showed a supershift since anti-ferritin antiserum was added to the same sample in lane 2 of FIG. 12 (ferritin-H, one or more upstream biding protein(s), and anti-ferritin antiserum binding to ferritin-H).

An interpretive drawing of these results is shown in FIG. 9, and the legend indicates which parts of the drawing correspond to which gel lanes in FIG. 10. FIG. 9 shows a schematic diagram of the β-globin gene 5' region 30 and the experiments used to elucidate protein binding to it. Ferritin 34 binds to promoter region 30 at ferritin binding site 44. Several DNA binding proteins 50 also bind to the β-globin promoter region. Binding proteins 50 all bind upstream of the ferritin binding site 44. Repression of the β-globin gene by ferritin is enhanced by a protein-protein interaction between ferritin and at least one of the promoter binding proteins 50. FIG. 9 illustrates the protein-protein-DNA complex ferritin 34 forms with at least one of binding proteins 32. Promoter region 30 has a ferritin binding site 44 and upstream of that a protein binding site 46. Binding protein 32 attaches to binding site 46, and ferritin 34 binds to ferritin binding site 44. Ferritin 34 and binding protein 32 then bind to one another, thereby creating a loop in the DNA. Promoter region 30 is cut into two smaller fragments 40 and 42 at restriction enzyme site 36 by restriction enzyme Sau96I. Because of the protein-protein interaction between binding protein 32 and ferritin 34, the complex remains intact. Thus, application of a restriction enzyme does not result in a mobility shift on a gel assay. This can be seen in lanes 2 and 3 of both FIG. 10 and FIG. 11. Removing proteins from the uncut DNA loop resulted in an intact promoter region 30 illustrated in lane 4 of FIG. 10 and land 4 of FIG. 11. Removing proteins from the DNA loop after being cut by a restriction enzyme resulted in two DNA fragments 40 and 42 shown in lane 5 of FIG. 10 and lane 5 of FIG. 11. Lane 7 of FIG. 10 shows the result of adding nuclear extract to fragments 40 and 42. The same complex found in lane 3 was formed by adding nuclear extract to DNA fragments 40 and 42.

When promoter fragments 40 and 42 were combined with a nuclear extract having ferritin 34 and binding protein 32, a gel shift resulted. This is shown in lane 7 of FIG. 10. This shows that the DNA loop is caused by ferritin binding to the promoter region.

Controls: Controls incorporated into the experiments described above, as depicted in FIGS. 10 and 11, included deproteinizing the complexes to show that the loop was cut by the restriction enzyme, and showing that unrelated DNA sequences (e.g., *P. putida* DNA) did not form a complex with this extract. As a further control, the single-band complex in lane 3 from gels identical to that in FIG. 11 was isolated, deproteinized, and also shown to contain equal amounts of the two restriction fragments resulting from Sau 96 I digestion. As shown in FIG. 10, lanes 6 and 7, the two Sau 96 I fragments of the β-globin 5' region shifted independently with this extract and did not form the large complex unless they were linked; furthermore, an approximately eight-fold greater protein concentration was required to begin to shift the separated restriction fragments than is required to initiate formation of the looped complex.

Discussion

Interpretations: The reported experiments show that DNA looping can be detected in vitro with an EMSA assay combined with digestion with a specific restriction enzyme. In these DNA looping experiments, the results show that sequences between −209 and +20 bp of the human β-globin gene interacted with upstream sequences between −210 and −610 bp. The looping was mediated by a partially purified extract containing a −150 promoter-binding protein and β-globin silencer-binding protein, confirmed by binding experiments with the extract and the separate binding sequences. When the single, large DNA-protein complex detected by our EMSAs was cut with Sau 96 I, the complex still migrated as a single, large complex high on the gels. (There was a small increase in migration of the cut complex which is to be expected since a single, double-stranded restriction cut changed the DNA conformation slightly.) It should also be noted that the binding of the proteins in this looped complex was very tight; it took a high excess of unlabeled −164/−128 and −584/−527 oligonucleotides to break up the complex (not shown). Furthermore, a comparison of the binding affinity of the full 630 bp DNA with the binding affinities of a mixture of the fragments generated by Sau 96 I, shows that it took approximately eight-fold less protein to form a shifted complex with the large, intact (630 bp) DNA than with a mixture of the separate fragments, showing that the binding to the larger 630 bp DNA was cooperative and that looping was occurring.

All of these results are consistent with known parameters and forces controlling DNA looping, which is mediated by two or more proteins showing cooperative (and, usually, tight) binding. The results of these experiments show that repression of the β-globin gene by upstream silencers can be mediated by DNA looping. This approach does not allow one to determine the identity of the proteins involved and may not work in cases where there is DNA supercoiling, as with certain plasmid contructs in vitro, or weak protein-protein interaction.

The presence of one or more upstream binding protein(s) which binds to the site(s) upstream of the ferritin-H binding site and at the same time binds to ferritin-H was further confirmed in the gel shift assay of FIG. 12. When ferritin-H is not present, one or more upstream binding protein(s) still binds to the 630 bp DNA fragment.

The loop in the promoter region formed by the interaction between ferritin and one or more upstream binding proteins enhances repression of the β-globin gene. Human cells generally have sufficient amounts of upstream binding proteins such that addition of ferritin alone to a human cell by the methods described herein is generally sufficient to cause repression of the β-globin gene and other genes regulated by this activity. In addition, binding of ferritin to the CAGTGC [SEQ ID NO: 6] ferritin binding site is generally sufficient to repress transcription of the β-globin gene.

EXAMPLE 3

Human Ferritin-H Localizes to the Nucleus of Primate Cells

Materials and Methods

Cell lines. CV-1 (African green monkey kidney epithelial) cells (adherent cells used for transfections/transient gene expression assays) were grown in DMEM with L-glutamine, 10% FBS and antibiotics (Miller, I. J. & Bieker, J. J. (1993) *Mol Cell Biol* 13, 2776-86).

Clones, transfections, and gene expression assays. Ferritin-H from the pcEXV-1 plasmid was PCR-amplified then cloned in the vector pCR4-TOPO. Ferritin-H was then digested using newly created restriction sites (Bse AI and BamHI), and cloned into the pEGFP-C1 vector to create a GFP-FtH fusion protein for expression in mammalian cells. Transfections of CV-1 cells were carried out with DMRIE-C transfection reagent, fluorescent protein plasmid pEGFP-C1 (Clontech), fluorescence microscopy and quantitative fluorescence of cell lysates with a microtiter plate reader.

Figure 13:
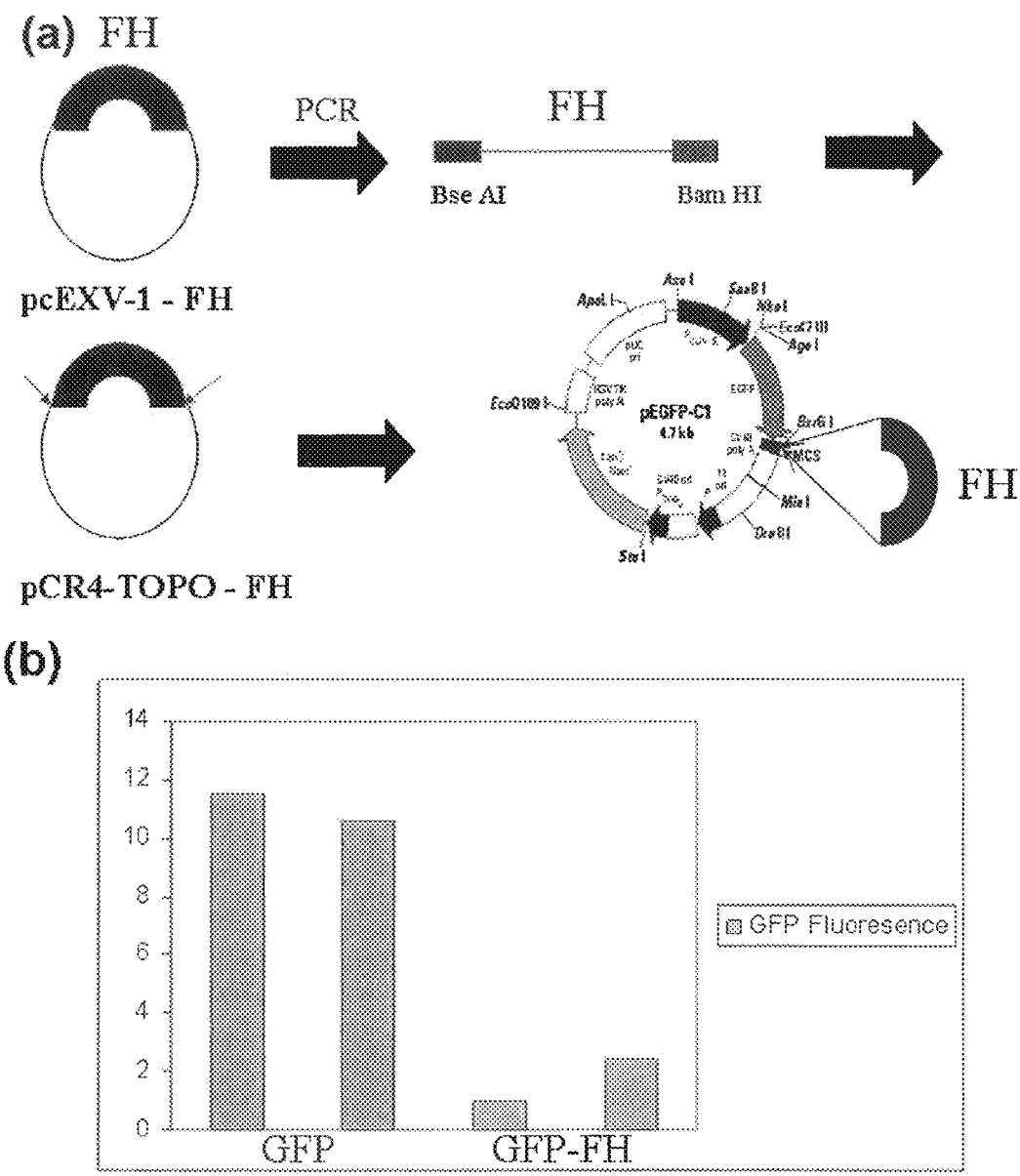
FIG. 13 illustrates cloning of the GFP-FtH fusion protein, and the expression of this fusion protein in CV-1 cells. (a) Diagram of the sub-cloning procedure. (b) Fluorescence measurements of GFP and GFP-FH fusion protein.
Figure 14:
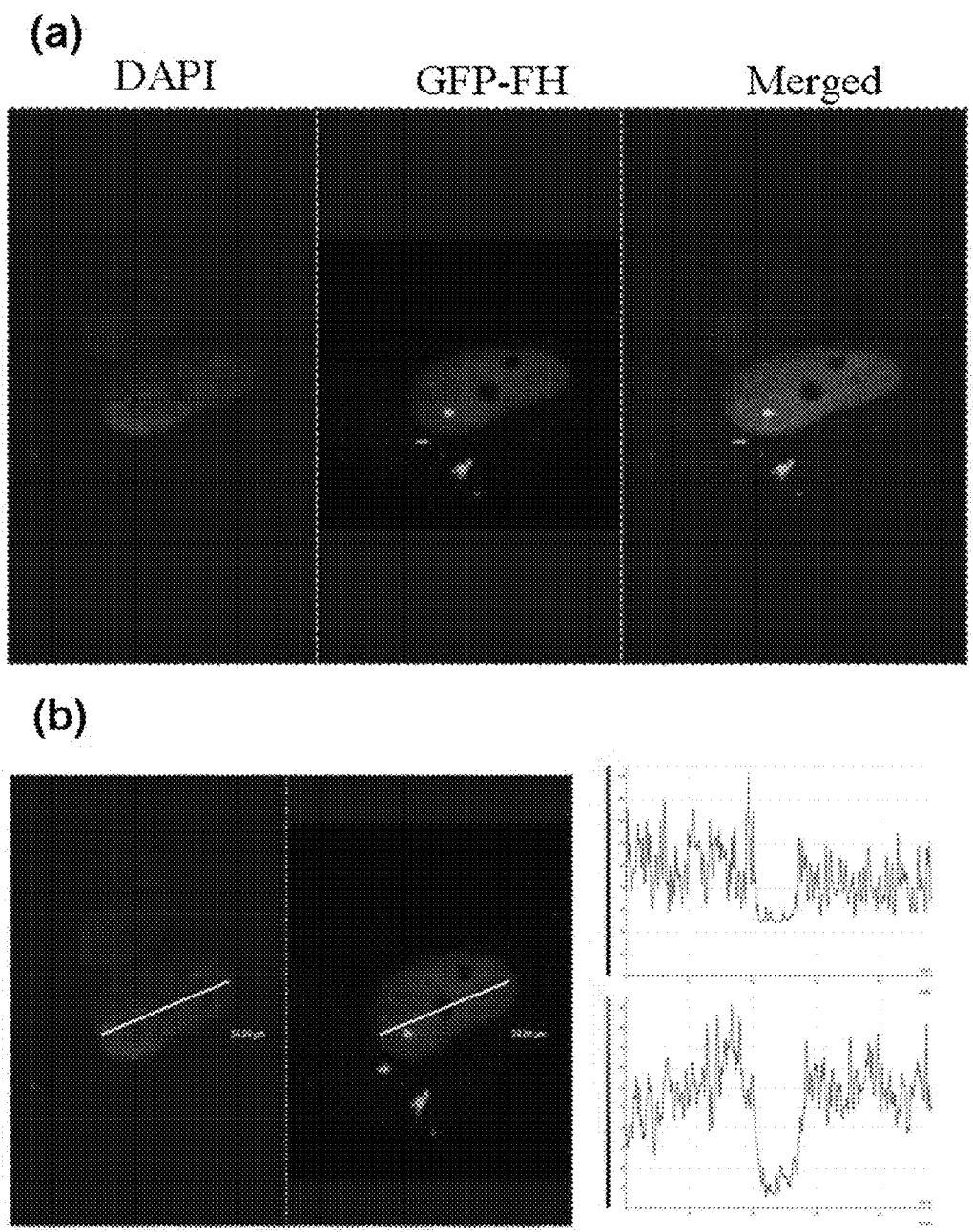
FIGS. 14, 16A, 23, 24 and 25 are executed in color. Copies of this patent or patent application publication with color drawing(s) will be provided by the Office upon request and payment of the necessary fee.

Microscopy. Cells transfected with EGFP (enhanced green fluorescent protein) vector (FIGS. 13 & 14) and cells transduced with FITC-labeled ferritin-H protein (FIGS. 24 & 25) were viewed with a Nikon Optiphot microscope with epifluorescence optics. For confocal microscopy, cells were fixed with 1% formaldehyde 48 hours after transfection, and stained with DAPI nuclear stain. Images were obtained using a Leica TCS NT laser-scanning confocal microscope and were analyzed with Leica TCS software.

Results and Discussion

To follow the intracellular translocation of human ferritin-H from the cytoplasm to the nucleus, ferritin-H gene was subcloned into an EGFP-C1 vector (FIG. 13), creating a fusion gene that was expressed as a GFP-FtH fusion protein. Thus, when this plasmid was transfected into primate (CV-1) cells, the fluorescence-tagged ferritin-H protein localized to the nucleus (FIG. 14(a)) and became evenly distributed in the nucleoplasm as determined by confocal microscopy and spectroscopy (FIG. 14(b)). These results confirmed that ferritin-H is a nuclear protein.

EXAMPLE 4

Ferritin-H Represses Adult β-Globin and Activates Fetal γ-Globin Expression

Materials and Methods

Cell lines. K562 (human erythroleukemia) cells were grown in suspension in RPMI 1640 medium with 10% or 15% fetal bovine serum (FBS) and antibiotics as described (Berg et al., (1989) *Nucleic Acids Res* 17, 8833-52) and harvested at a density of $10^6$ cells/ml for making nuclear extracts.

Proteins and antibodies. Purified recombinant ferritin-H and ferritin-L and polyclonal monospecific antibodies against ferritin-H and ferritin-L were obtained from Sonia Levi and Paolo Santambragio of the University of Milan and Paolo Arosio of Breschia University. Monospecific polyclonal antibodies to ferritin-H and ferritin-L were also obtained from Suzy Torti of Wake Forest University Medical Center, Winston-Salem, N.C.

Chromatin immunoprecipitation (ChIP) assays. ChIP analyses with anti-FtH antiserum were used to show that ferritin-H is bound to the –150 β-globin promoter site in vivo in K562 cells in which the β-globin gene is repressed. Chromatin immunoprecipitations using anti-FtH antiserum were performed with sonicated, formalin-fixed chromatin from K562 cells. PCR was performed on the Ab-precipitated DNA using primers flanking the ferritin-H binding (CAGTGC [SEQ ID NO: 6]) site. One set of β-globin promoter-specific primers gave a PCR product of 100 bp, whereas a second set of β-globin promoter-specific primers gave a 318 bp PCR product. The 100 and 318 bp PCR bands were sequenced to confirm the identity of the ferritin-H binding site.

Antisense-oligonucleotide and transfections. Single stranded antisense-oligonucleotide to ferritin-H mRNA was labeled by covalent attachment of Alex488 using chemistry and reagents specified by the manufacturer (Molecular Probes, Inc.). Transfections of K562 cells with the Alexa488-labeled antisense-oligonucleotide to ferritin-H mRNA were carried out with DMRIE-C and the Alexa488 tag was followed by fluorescence microscopy (FIG. 16(A)).

Total RNA isolation and RT-PCR. Total RNA was isolated from cells (e.g., K562 human erythroleukemia cells) using the Trizol procedure, and this RNA was used for quantitative RT-PCR. The quality of the isolated RNA was assessed by the quality and ratio of 18 & 28S RNA bands on gel electrophoresis, before performing RT-PCR.

Quantitative RT-PCR from the total RNA isolated from heme-treated K562 cells (KH) vs. FtH-antisense-treated cells (KA) was performed using gene-specific primers for β-globin, γ-globin, ferritin-H and ferritin-L, as outlined in the BioRad iCycler manual.

Results and Discussion

Figure 15:
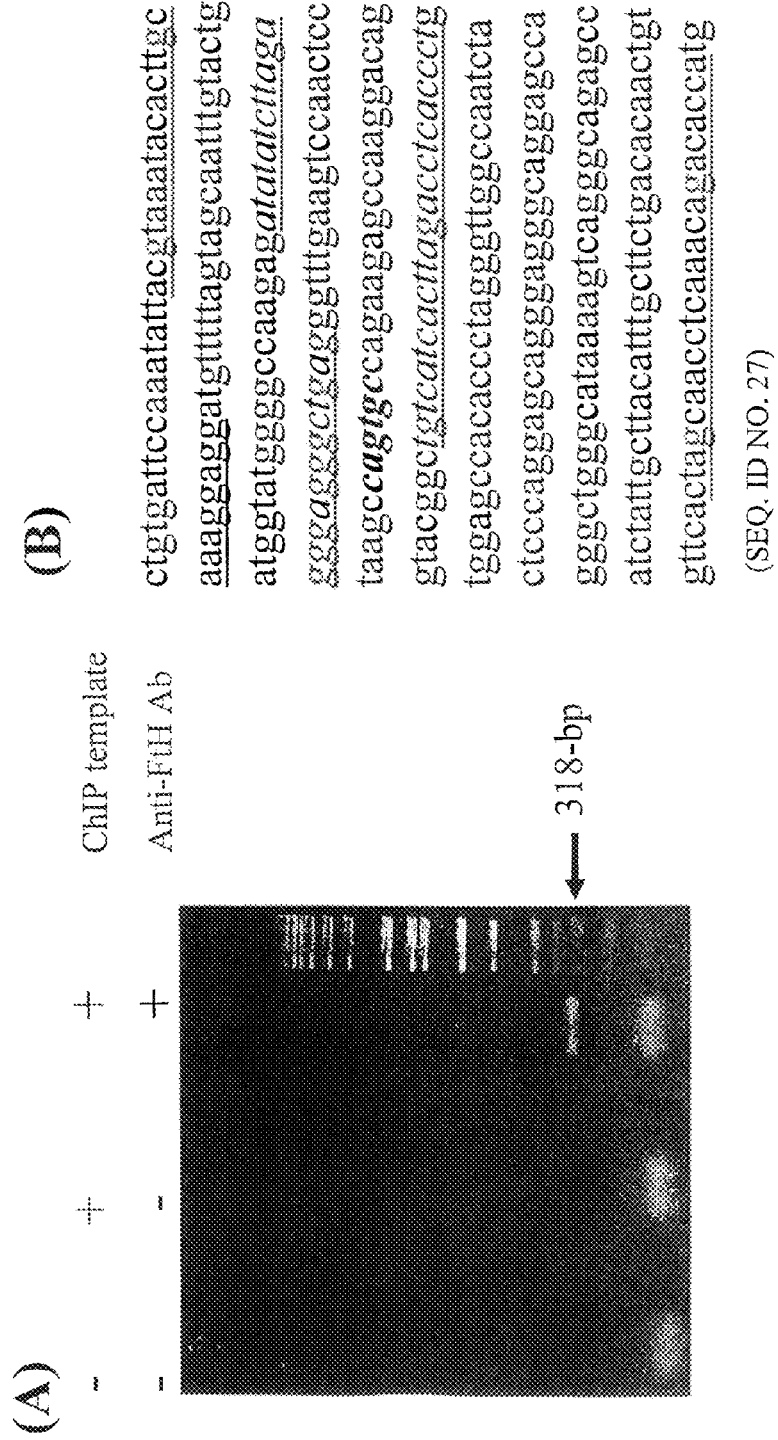
FIG. 15 illustrates CHIP analyses with anti-FtH antiserum showing that ferritin-H is bound to the −150 β-globin promoter site in vivo in K562 cells in which the β-globin gene is repressed. (A) Agarose gel of the DNA PCR product produced from chromatin immunoprecipitated with anti-FtH antiserum. (B) DNA sequence [SEQ ID NO. 27] of the PCR product of ChIP, produced with two sets of primers shown as underlined and italicized letters, with the sequence of the ferritin-H binding site shown in bold letters.

In human K562 erythroleukemia cells, the adult β-globin gene is repressed. Therefore, ferritin-H, which has been identified as a repressor of the β-globin gene (see FIGS. 1 and 6), would be expected to be bound to its identified binding sequence, the –150 CAGTGC [SEQ ID NO: 6] promoter sequence (FIGS. 2 through 5) in K562 cells. Chromatin immunoprecipitations using anti-FtH antiserum were performed with sonicated, formalin-fixed chromatin from K562 cells. PCR was performed on the Ab-precipitated DNA using sequences shown in FIG. 15 gave a PCR product of 100 bp, whereas primers to the underlined sequences gave a 318 bp PCR product (dark arrow, panel (15A)). The 100 and 318 bp PCR bands sequenced from the anti-FH precipitated DNA contained the –150 CAGTGC [SEQ ID NO: 6] FH-binding motif (bold), in panel (15B). The sequence in panel 15B corresponds to SEQ ID NO: 27. These results show that the β-globin repressor ferritin-H is bound to the β-globin promoter in human cells that have that gene repressed.

Figure 16:
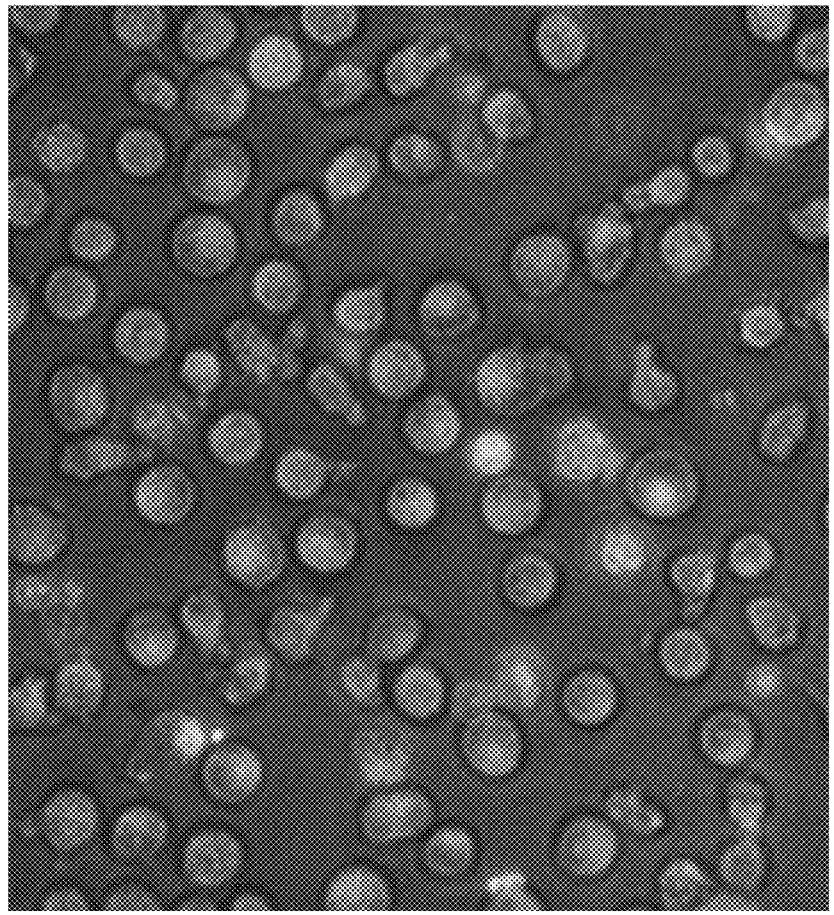
FIG. 16B illustrates quantitative RT-PCR (BioRad iCycler manual) from total RNA isolated from heme-treated K562 cells (KH) vs. FtH-antisense-treated cells (KA) showed that ferritin-H and γ-globin expression are decreased 90% by the FtH-antisense treatment.

In human K562 cells the adult β-globin gene is repressed, whereas the fetal γ-globin gene is expressed at high levels. It has been demonstrated in the '669 patent application that ferritin-H represses the β-globin gene. Ferritin-H is also expected to activate the γ-globin gene. Therefore, an antisense oligonucleotide directed at ferritin-H mRNA is expected to knock down ferritin-H and reverse this expression pattern in K562 cells. A ferritin-H antisense oligonucleotide was labeled with the bright fluorescent compound Alexa488 and transfected into K562 cells using DMRIE-C transfection reagent. As shown in FIG. 16(A), the fluorescently-tagged antisense oligo entered the nuclei of 90 percent of the K562 cells. Total RNA was isolated from the antisense-treated cells (KA) as well as from cells not treated with antisense (KH), and the RNA was used for quantitative RT-PCR with specific primers for β-globin, γ-globin, ferritin-H, and ferritin-L. Ferritin-H and γ-globin were both decreased 90 percent by antisense to ferritin-H mRNA (FIG. 16(B)), whereas, ferritin-L changed very little and β-globin expression increased relative to overall globin expression. These results show that ferritin-H is not only a repressor of the adult β-globin gene, but also that ferritin-H is required for high-level expression of fetal γ-globin. These results have been confirmed in differentiating erythroid cells from pediatric sickle cell patients where it was shown that ferritin-H represses adult HbS hemoglobin and induces fetal HbF hemoglobin (see FIG. 23 below).

EXAMPLE 5

Human Ferritin-H Represses β-Major Globin but not β-Minor Globin in Mouse

Materials and Methods

Preparation of nuclear extracts. Each nuclear extract preparation was made from two liters of K562 cells ($1 \times 10^6$ cells/ml) using the procedure of Dignam, Lebovitz, and Roeder (Dignam, J. D., Lebovitz, R. M. & Roeder, R. G. (1983) *Nucleic Acids Res* 11, 1475-89). Protein content of the extracts ranged from 3 to 6 mg/ml. Extracts enriched 80-90% in ferritin-like protein(s) were prepared by treating the crude extracts with proteinase K and/or heat at 75° C. (Atkinson, B. G., Dean, R. L., Tomlinson, J. & Blaker, T. W. (1989) *Biochem Cell Biol* 67, 52-7).

Oligonucleotides. Synthetic oligonucleotides and their complementary strands corresponding to −232/−188, −164/−128, and −127/−107 of the human β-globin promoter, to −183/−147 of the mouse β-major globin promoter, and to the mouse α-globin GATA-1 binding site were purified and annealed as previously described (Berg et al., (1989) *Nucleic Acids Res* 17, 8833-52), and the double-stranded oligos were end-labeled with $^{32}$P-γ-ATP and T4 kinase and/or used as unlabeled competitors in gel mobility shift assays.

Figure 17:
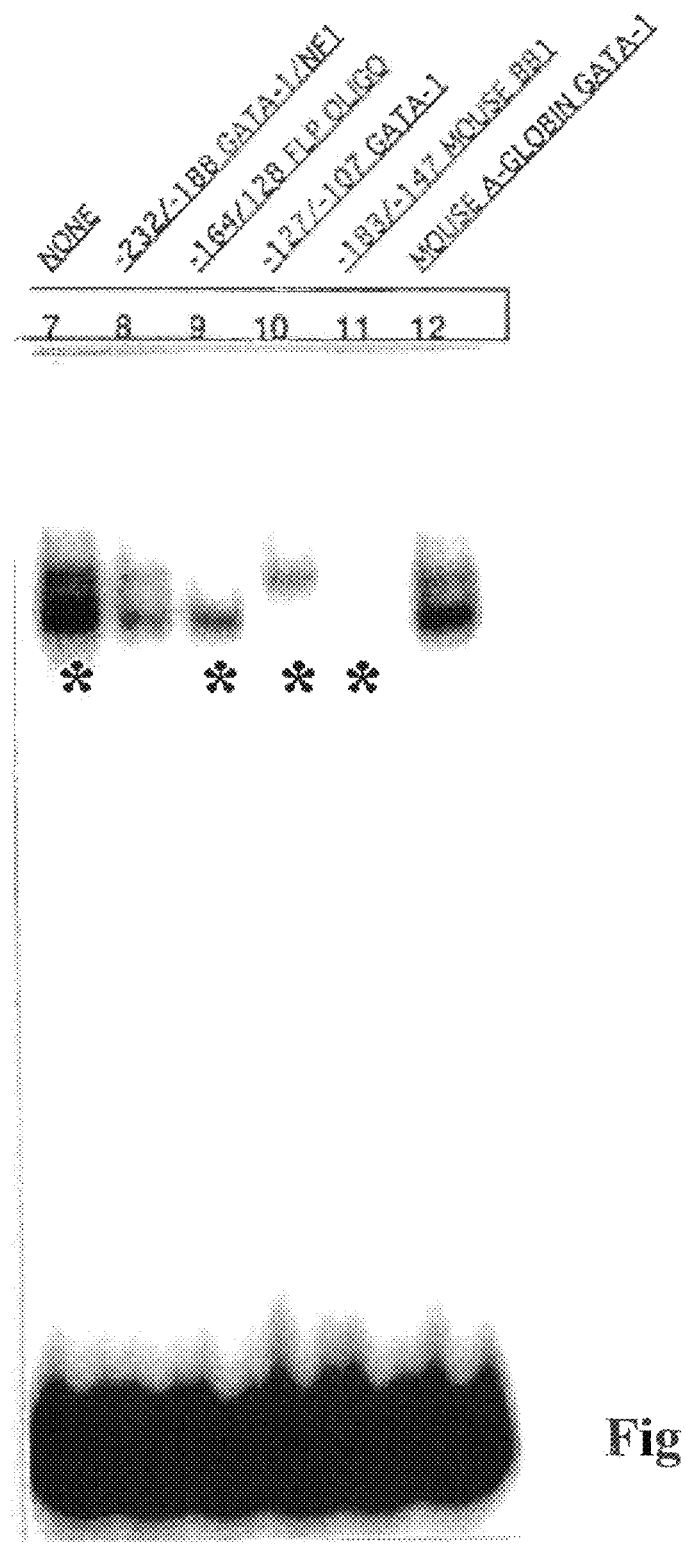
FIG. 17 illustrates that mouse β-major and human β promoter sequences cross-compete for nuclear ferritin-H binding in an EMSA (gel shift assay), using mouse β-major promoter sequence (FIG. 5) as the labeled probe and the unlabeled double-stranded oligonucleotide probes listed above the gel as competitors at 200× excess. The source of the nuclear proteins was human K562 cells. The star at left (lane 7) shows shift bands with no competition, and lanes marked by the 3 stars show bands selectively competed by the oligos (lanes 9 and 10) or completely competed by "self" (lane 11).
Figure 19:
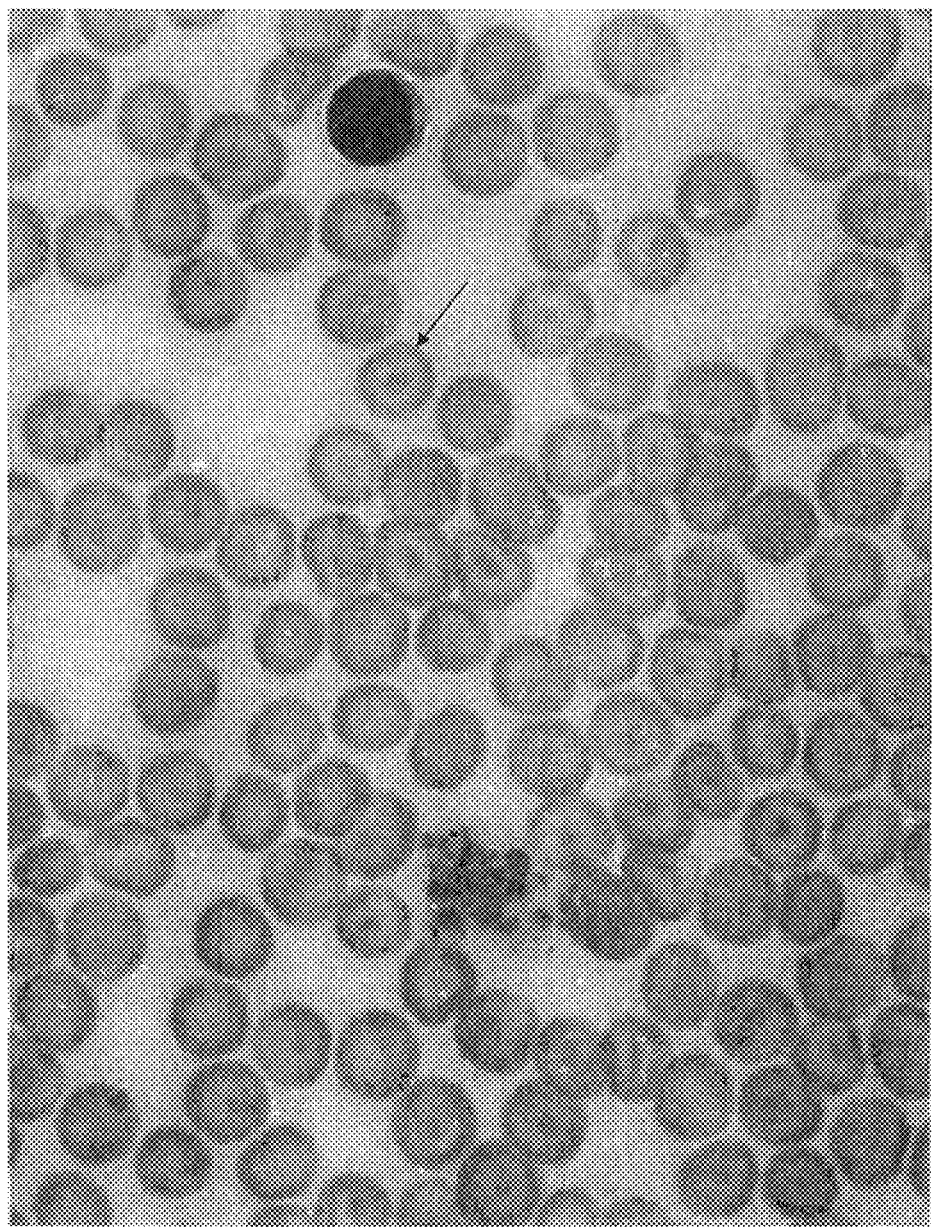
FIG. 19 illustrates that FtH-Tg mice appear to have a mild β-thalassemia characterized by increased numbers of target cells (arrow), indicative of inclusions due to precipitated excess alpha-chains and the mouse β-major globin gene repressed by the ferritin-H.

Gel mobility shift assays. Gel retardation assays (i.e., gel shifts) were used to determine DNA binding of K562 cell nuclear extract proteins to analogous β-globin promoter regions of the human adult β-globin gene versus the mouse β-major globin gene, using radioactively labeled and unlabeled double stranded oligonucleotides as subtrates and competitors, respectively, as described under Material and Methods for Example 1 and in the Brief Description for FIG. 17.

Transgenic mice: construction and analysis. Ferritin-H transgenic (Tg) mice designed to express human ferritin-H in mouse definitive/adult red blood cells was created by injection of a DNA construct containing the human ferritin-H cDNA sequence driven by a human β-globin promoter truncated at −135 bp (so that it did not contain the −150 ferritin-H binding site, to avoid the transgene being self-repressing) plus a micro LCR construct at the 5'-end to act as an enhancer, and 3' β-globin IVS 2, exon 3, and polyadenlylation sequences for proper message processing. The construct also had no 5'-UTR IRE sequences to avoid self-suppression at the translational level. This DNA construct (diagramed in FIG. 18(*a*)) was injected into fertilized mouse embryos to make FtH-Tg mice. Shortly after birth, a small amount of blood was obtained from founder Tg mice for globin chain identification and relative quantification by urea-gel electrophoresis (FIG. 18(*b*)), and for blood smears (FIG. 18(*c*)).

Results and Discussion

Competitive EMSAs (gel mobility shift assays) were performed between the conserved regions of the adult human β-globin promoter and the mouse β-major globin gene promoter (FIG. 17), using mouse β-major promoter sequence (FIG. 5) as the labeled probe and the unlabeled double-stranded oligonucleotide probes listed above the gel as competitors at 200× excess. The source of the nuclear proteins was human K562 cells. Lane 7 (no competitor) showed three shift bands, and the top two bands were competed away by the human β-globin promoter ferritin-H binding oligonucleotide (lane 9). The bottom of the three bands in lane 7 was competed away by a canonical GATA-1 binding oligonucleotide (lane 10). All three bands were competed away by the unlabeled version of the mouse β-major globin oligonucleotide ("self"), lane 11. Two other oligonucleotides containing unrelated DNA sequences, lanes 8 and 12, showed no specific competition. These results show that the human ferritin-H in nuclear extracts of K562 cells binds the analogous regions of the human beta promoter and the mouse β-major promoter, as predicted by the aligned, conserved DNA sequences shown in FIG. 5. The mouse β-minor globin promoter does not contain the ferritin-H binding motif at all.

Figure 20:
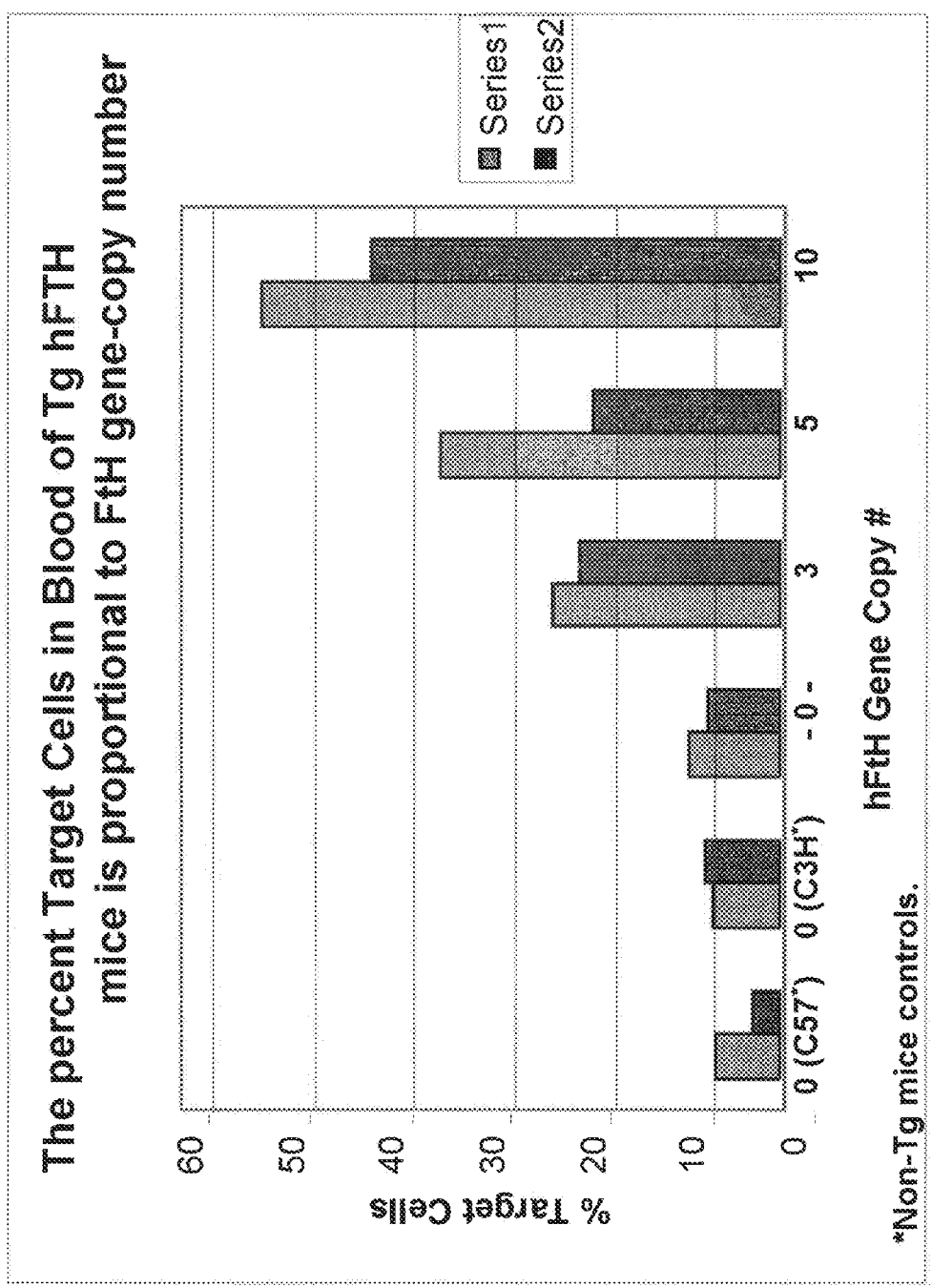
FIG. 20 illustrates percentage of cells indicative of inclusions due to precipitated excess α-chains in ferritin-H transgenic mice versus copy number of ferritin-H trans-gene.

Transgenic mice were constructed with a human ferritin-H construct engineered so the the transgene should be expressed mainly in the definitive/adult erythroid lineage but not in the primative/embryonic erythoid lineage (FIG. 18(*a*) and Materials & Methods, Example 5). As shown in FIG. 18(*b*), UT (urea) PAGE gel electrophoresis of globin chains from a ferritin-H transgenic mouse (lane 1), a non-transgenic mouse (lane 2), and globin standards (lane 3) was performed and the stained globin peptide bands were quantified. The ratio of β-major to β-minor globin was decreased in the ferritin-H transgenic mouse because the human ferritin-H binds the CTGTGC [SEQ ID NO: 6] sequence in the β-major promoter but cannot bind the β-minor promoter which has no ferritin-H binding motif. Blood smears from non-transgenic mice (wt) and transgenic mice (FtH-Tg) were also compared, as shown in FIG. 18(*c*). The FtH-Tg mice had a mild β-thalassemia characterized by increased numbers of target cells (arrow), indicative of inclusions due to precipitated excess α-chains (FIGS. 18(*c*) and 19). The percentage of target cells was found to be approximately proportional to the ferritin-H gene copy number in these transgenic mice (FIG. 20). There should be no excess alpha-chains in humans treated with ferritin-H and thus no β-thalassemia, because, unlike the mouse, humans respond to β-globin repression with increased γ-globin synthesis.

EXAMPLE 6

Ferritin-H Protein, Ferritin-H Vector, and Abscissic Acid Produce a Switch from HbS-to-HbF Production in Human Sickle Cell Erythroid Precursor Cells Materials and Methods Cell lines. Human NTERA-2 (NT-2) embryonal carcinoma stem cells (ATCC # CRL-1973) were cultured in DMEM medium with 10% FBS and antibiotics.

Western blots and quantification. Cell lysates (i.e., extracts of human NT-2 cells) were boiled for 3-5 minutes in SDS buffer, layered onto polyacrylamide gels and were run with SDS electrophoresis buffer at 90 volts for 30 minutes. Electrophoresed samples were then placed in 3% BSA buffer and transferred at 80 volts for 2 hours to blotting membranes. A blocking reaction was performed over night with blocking buffer from ECL advance kit (GE Healthcare Bio-Sciences, NJ), followed by incubation for 4 hours in BSA buffer with fluorescent secondary antibody (1:10000) and primary anti ferritin-H (anti-FtH) polyclonal antiserum (1:1000). Ferritin-H detection was achieved using the LI-COR apparatus to visualize the fuorescent bands and Odyssey software to quantify the stained bands of ferritin-H. Isolation and culture of human mononuclear cells and maturation of erythroid precursor cells are diagrammed in FIG. 22. Whole blood was obtained from pediatric sickle cell patients at the time of scheduled transfusion therapy under an approved IRB protocol. Mononuclear cells (monocytes) were obtained by low-speed centrifugation in Ficoll-Paque PLUS and cultured in a 2-phase liquid culture system as previously described (Meyron-Holtz, E.G., et al., *Blood* 94:3205-3211, 1999). Briefly, mononuclear cells were cultured in the presence of cytokines that expand myeloid precursor cells, and in the presence of cyclosporin A to inhibit lymphoid precursor cells for seven days. This part of the culture is referred to as phase I. Non-adherent myeloid precursor cells in suspension were harvested and recultured in the presence of human recombinant erythropoietin to stimulate maturation of the erythroid precursor cells. All the other precursor cells died because they did not have their corresponding hormone to keep them alive. This part of the culture is referred to as phase II.

During phase II, as the erythroid precursor cells differentiated into hemoglobin-containing normoblasts under the influence of recombinant human erythropoietin (rhEpo), ferritin-H was administered to the cultures in one of three delivery systems: (1) as the protein/peptide alone or with a protein transfection reagent (e.g., Chariot, supplied by Active Motif); (2) as the plasmid-encoded gene using DNA transfection reagents, e.g., DMRIE-C; or (3) as an inducer of the endogenous ferritin-H gene, e.g., abscissic acid according to established protocols for these procedures. Any user of this technology can easily determine the optimal amounts, frequency, and timing of addition of these agents for best clinical results, i.e., maximal HbF production. In the example described in FIG. 23, ferritin-H protein, ferritin-H vector, and ferritin-H inducer were administered to the cultures in day 1 of the phase II culture.

Figure 23:
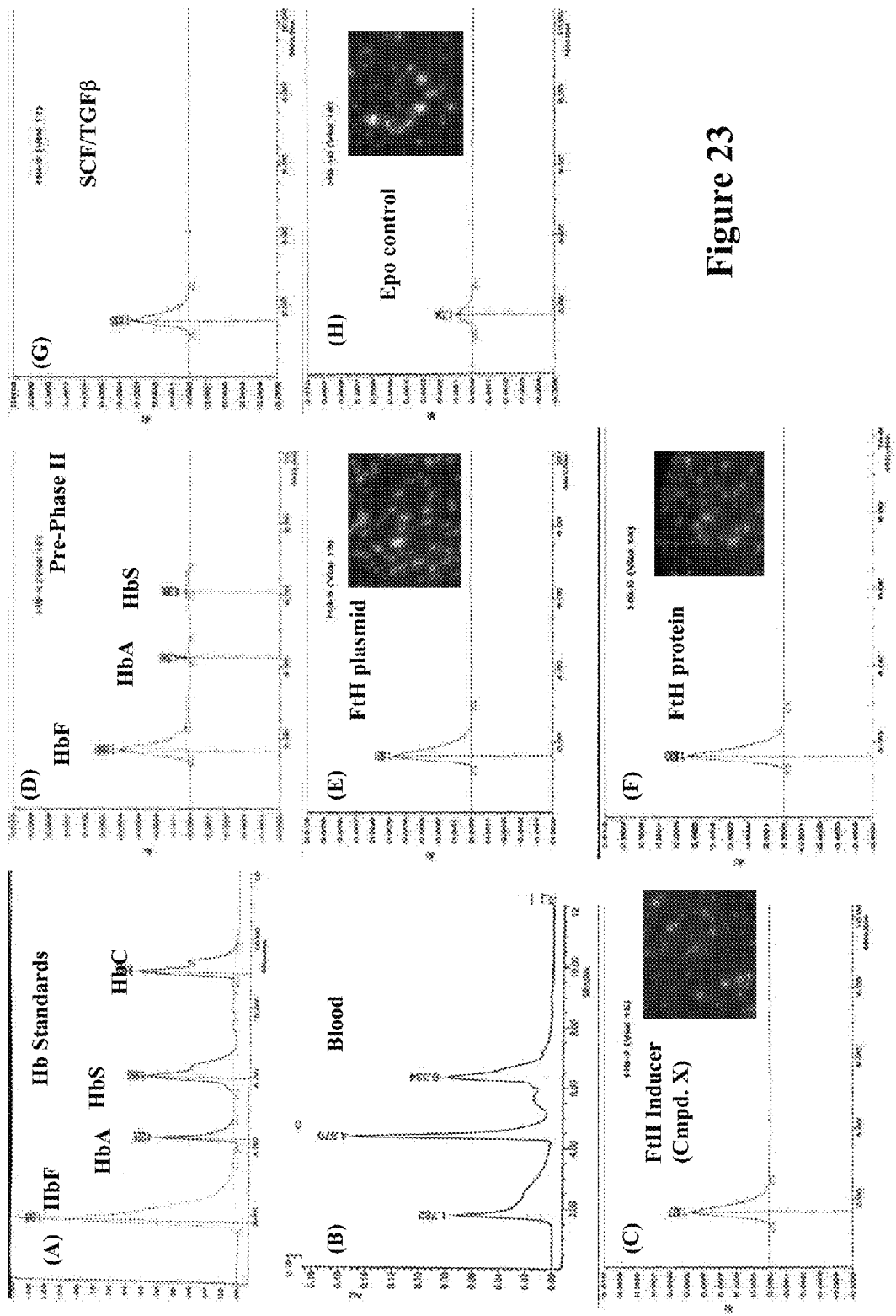

High-pressure liquid chromatography (HPLC) separation and quantitation of human hemoglobins (Hb's). As shown in FIG. 23, Human hemoglobin (Hb) types were separated (and quantified) by cation exchange high-performance liquid chromatography (HPLC) as previously described (Bhanu et al. (2005) *Blood*, 105(1):387-393, 2005; B. et al. (2002) *Journal of Pediatric Hematology/Oncology* 24:284-290). Transduction by ferritin-H protein (F), ferritin-H vector (E), or ferritin-H inducer (C) produced a total switch from HbS-to-HbF production, which was pancellular as indicated in the microphotographic inserts of immuno-HbF fluorescence, whereas HbF production by erythropoietin (Epo) alone (H) was less and was expressed in a minority of erythrocytes.

Results and Discussion

Figure 21:
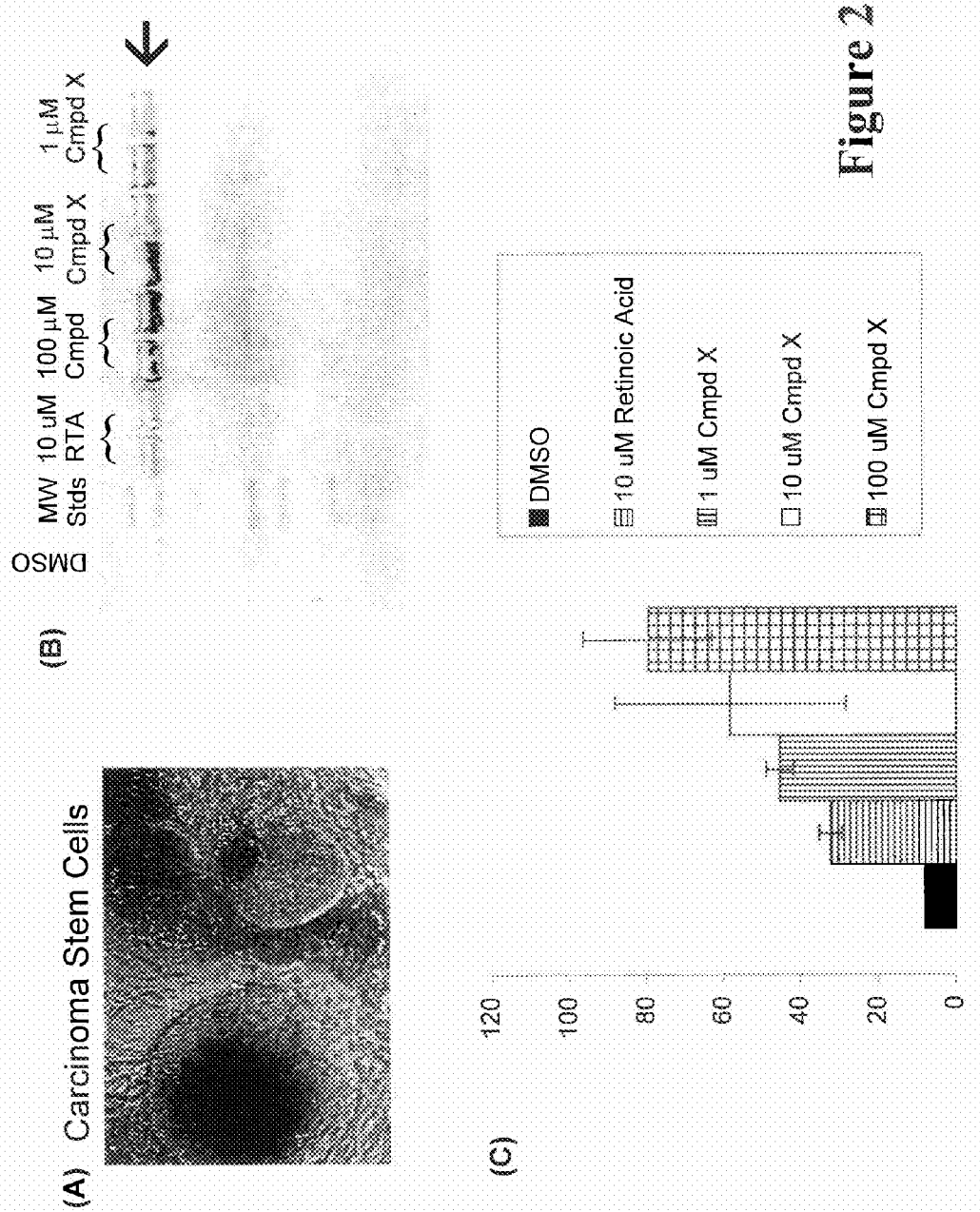
FIG. 21 illustrates the induction of endogenous ferritin-H gene expression in NT-2 (NTERA-2) stem cells by exogenously-applied retinoic acid and a related herbal compound (abscissic acid [ABA], labeled as "Cmpd X" in this figure), during the first 8 days of culture. (a) NT-2 cells cultured in the presence of 10 μM RTA for 8 weeks. Phase contrast photo at 100×. (b) Western blot for ferritin-H from DMSO-control, RTA-induced, and ABA-induced NT-2 cells after 8 days in the presence of the indicated compounds. The arrow indicates the main ferritin-H band. (c) Quantitation of the western blot in (b) using the LI-COR apparatus to visualize and Odyssey software to quantify the stained bands of ferritin-H. Bars=Std. Deviations.

The experiment in FIG. 21 shows that retinoic acid (RA), a known inducer of ferritin-H gene expression, and abscissic acid, a plant-derived compound structurally analogous to RA, both activated ferritin-H expression in NT-2 cells, a human embryonal carcinoma stem cell line. These compounds are thus candidate drugs for activating ferritin-H in diseases characterized by iron over-load, such as transfusion-dependent cases of sickle cell disease and β-thalassemias.

Figure 22:
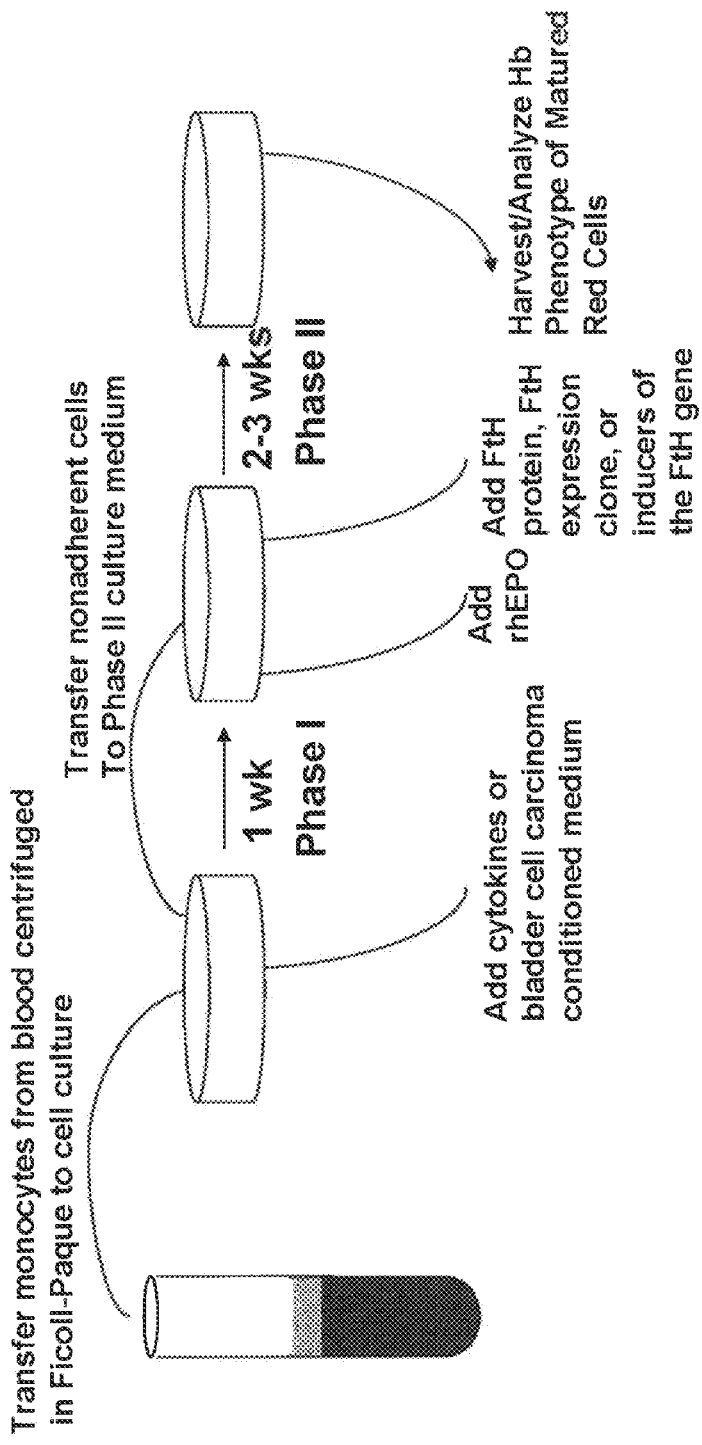
FIG. 22 illustrates the experimental design for changing the hemoglobin (Hb) phenotype of sickle cell erythroid precursor cells from HbS-to-HbF ex vivo by transduction with ferritin-H prior to re-implantation, as a treatment of sickle cell disease.
Figure 24:
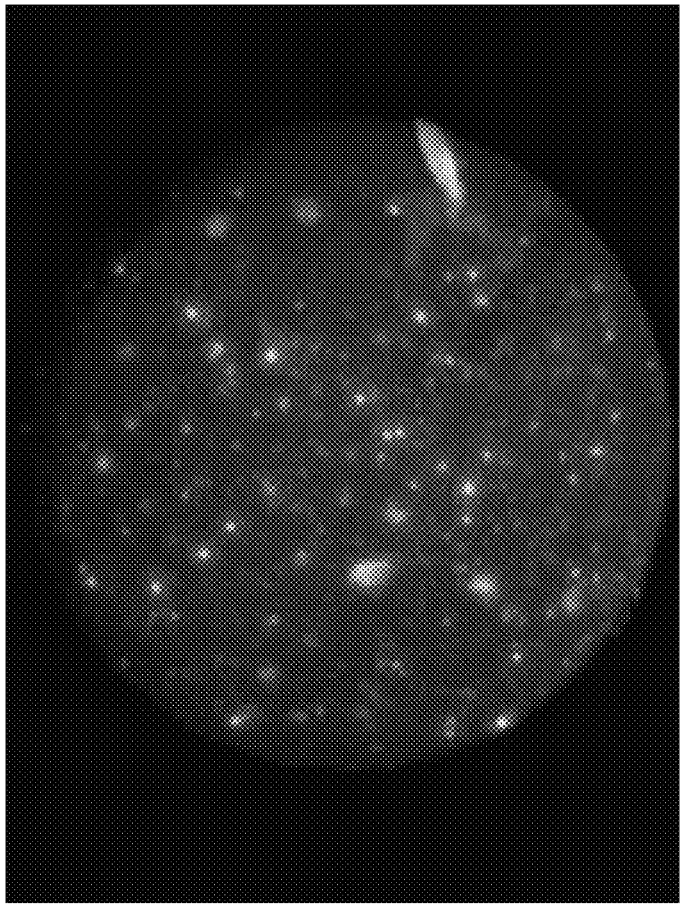
Figure 25:
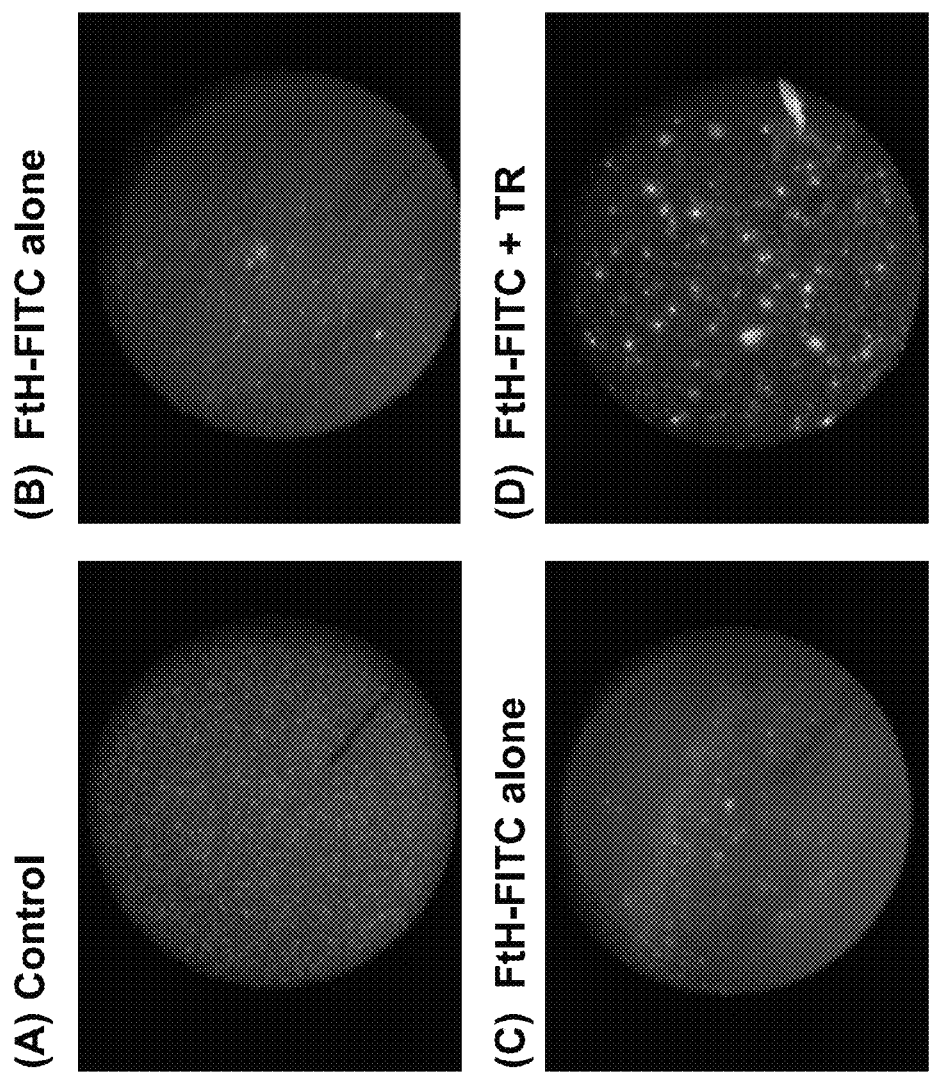

In FIG. 22, an experimental design for changing the hemoglobin (Hb) phenotype of sickle cell erythroid precursor cells from HbS-to-HbF ex vivo by transduction with ferritin-H prior to re-implantation, as a treatment of sickle cell disease is depicted. Differentiating human erythroid cells took up ferritin-H protein labeled with FITC florescent dye (FtH-FITC) directly from the surrounding milleau (FIGS. 24 and 25). Pre-incubating the FtH-FITC with a protein transfection reagent (TR; Chariot in this case) facilitated the rate of uptake, resulting in a more intense fluorescence in each of the erythroid cells. As shown in FIG. 23, in either case (with or without transfection reagent), enough ferritin-H entered the cells and their nuclei to result in repression of HbS and activation of HbF (fetal hemoglobin).

FIGS. 24 and 25 show that FtH-FITC protein can be taken up by human erythroid precursor cells. Six experiments like that in FIG. 23 have shown that ferritin-H protein administered by adding the soluble protein to the culture medium induces a complete HbS-to-HbF switch in these same cells.

Figure 26:
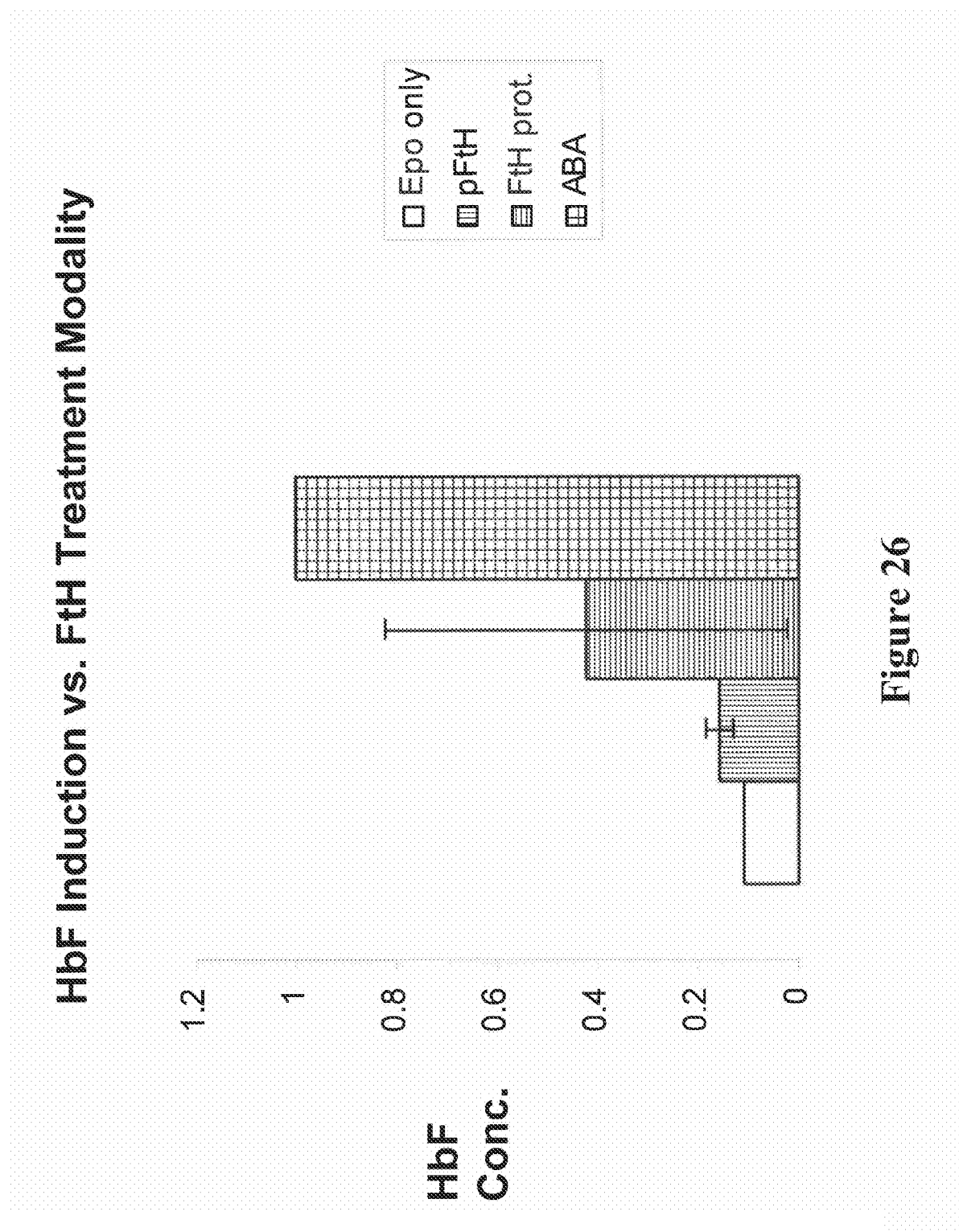
FIG. 26 illustrates the relative amounts of fetal hemoglobin (HbF) produced in adult human erythroid precursor cells in response to ferritin-H delivered as a gene (pFtH), as the protein (ferritin-H), or as an inducer of ferritin-H gene expression (ABA).

Therefore, putting ferritin-H in the vicinity of erythroid precursor cells, such as by an injection into bone marrow, or by administering ex vivo to erythroid precursor cells and reinfusing the erythroid precursor cells back to the sickle cell patients, should produce red blood cells with enough HbF to never sickle, i.e., produce a phenotypic cure. As shown by the bar graph in FIG. 26, all methods of delivering ferritin-H (as the gene, the protein itself, or via an inducer compound) resulted in production of HbF, although the protein or the inducer compound appeared to be more efficacious than the vector-born gene. However, all three modes of delivery of ferritin-H induced a complete HbS-to-HbF switch (FIG. 23, see below).

In FIG. 23 ferritin-H induction of HbS-to-HbF switching in erythroid precursor cells from pediatric sickle cell disease patients was shown. Human hemoglobin (Hb) types were separated (and quantified) by cation exchange high-performance liquid chromatography (HPLC) as previously described (Bhanu et al. (2005) *Blood*, 105(1):387-393, 2005; B. et al. (2002) *Journal of Pediatric Hematology/Oncology* 24:284-290). Transduction by ferritin-H protein (panel F), ferritin-H vector (panel E), or ferritin-H inducer (panel C) produced a total switch from HbF to HbF production, which was pancellular as indicated in the microphotographic inserts of immuno-HbF fluorescence, whereas HbF production by erythropoietin (Epo) alone (panel H) was less and was expressed in a minority of erythrocytes. While TGFβ is a known inducer of ferritin-H and, in combination with stem cell factor (SCF), produced a partial switch to HbF, the amount of HbF was not as great as with ferritin-H (panel G); and these agents (SCF and TGFβ) cannot be used in human patients because of side-effects including the possibility of tumorigenesis. This HbS-to-HbF switch was observed in erythroid precursor cells from 23 days to 4 weeks after administration of ferritin-H protein, ferritin-H vector, or ferritin-H inducer in phase II culture. The erythroid precursor cells can be reinfused back to the sickle cell patients after the HbS-to-HbF switch is induced. The erythroid precursor cells can also be reinfused back to the sickle cell patients before the HbS-to-HbF switch is induced and produce the HbS-to-HbF switch in the body of the patient. These results show that ferritin-H can be used clinically to induce a hemoglobin switch from HbS-to-HbF expression, which has been utilized as a phenotypic cure for this red blood cell malady.

EXAMPLE 7

Retinoic Acid Induces NT-2 Cells to Differentiate into Neurons

Results and Discussion

In the experiment of FIG. 21 as described in example 6, embryonal carcinoma stem cells in the NT-2 cell culture were also observed to differentiate into neurons in spheres when cultured with retinoic acid for 8 weeks. Retinoic acid, as inducer of ferritin-H gene expression, induced neuronal differentiation as a downstream event of ferritin-H expression activation. Therefore, in addition to its gene regulation role, ferritin-H is protective against oxidative damage that is caused by free iron, which is linked to aging and neurodegenerative diseases such as Parkinson's disease, Huntington's disease, and Alzheimer's disease, etc. These two compounds, retinoic acid and abscissic acid, are thus candidate drugs for activating ferritin-H in above mentioned neurodegenerative diseases and dementias. Likewise, an expression clone of a ferritin-H subfamily gene and/or a ferritin-H protein family member is predicted to achieve the same results.

Whereas, the present invention has been described in relation to the drawings attached hereto, it should be understood that other and further modifications, apart from those shown or suggested herein, may be made within the spirit and scope of this invention.

I claim:

1. A method for repressing production of β-globin protein and increasing production of γ-globin protein in a human cell, the method comprising the steps of:
    providing at least one cell that is a precursor of or that is differentiating to become a human β-globin producing cell;
    providing a ferritin-H protein; and
    contacting the provided cell or cells with the ferritin-H protein, whereby the ferritin-H protein is introduced into the provided cell or cells; and
    culturing the provided cell or cells with the ferritin-H protein for a length of time sufficient so that the production of β-globin is decreased and the production of γ-globin is increased in the provided cell or cells.

2. The method of claim 1, wherein the ferritin-H protein is human ferritin-H protein.

3. The method of claim 1, wherein the ferritin-H protein is a functional derivative of human ferritin-H protein.

4. The method of claim 1, wherein the step of contacting the provided cell or cells with the ferritin-H protein occurs in vitro.

5. The method of claim 1, wherein a polypeptide transfection agent is administered together with the ferritin-H protein.

6. A method for treating sickle cell disease, the method comprising the steps of:
    obtaining blood from a sickle cell patient;
    culturing cells in the blood to produce erythroid precursor cells wherein the hemoglobin phenotype of the erythroid precursor cells is HbS;
    providing a ferritin-H protein;
    contacting the erythroid precursor cells with the ferritin-H protein, whereby the ferritin-H protein is introduced into the erythroid precursor cells;
    culturing the erythroid precursor cells for a length of time sufficient to change hemoglobin phenotype of at least a portion of the erythroid precursor cells from HbS to HbF; and
    reinfusing the erythroid precursor cells back to the sickle cell patient.

7. The method of claim 6, wherein the ferritin-H protein is human ferritin-H protein.

8. The method of claim 6, wherein the ferritin-H protein is a functional derivative of human ferritin-H protein.

9. The method of claim 6, wherein a protein transfection agent is administered together with the ferritin-H protein.

* * * * *